US012325677B2

(12) United States Patent
Takeoka et al.

(10) Patent No.: US 12,325,677 B2
(45) Date of Patent: Jun. 10, 2025

(54) CARBOXYLIC ACID-TYPE LIPID, AND LIPID PARTICLE AND LIPID MEMBRANE EACH COMPRISING CARBOXYLIC ACID-TYPE LIPID

(71) Applicants: Toray Industries, Inc., Tokyo-to (JP); Nanotheta Co, Ltd., Tokyo-to (JP)

(72) Inventors: Shinji Takeoka, Tokyo-to (JP); Keiko Nakahara, Tokyo-to (JP); Mamoru Nishiura, Tokyo-to (JP); Shinya Otsubo, Tokyo-to (JP); Hajimu Kurumatani, Tokyo-to (JP); Toru Arakane, Tokyo-to (JP)

(73) Assignees: Toray Industries, Inc., Tokyo-to (JP); Nanotheta Co, Ltd., Tokyo-to (JP)

( * ) Notice: Subject to any disclaimer, the term of this patent is extended or adjusted under 35 U.S.C. 154(b) by 1056 days.

(21) Appl. No.: 17/286,448

(22) PCT Filed: Oct. 17, 2019

(86) PCT No.: PCT/JP2019/040984
§ 371 (c)(1),
(2) Date: Apr. 16, 2021

(87) PCT Pub. No.: WO2020/080495
PCT Pub. Date: Apr. 23, 2020

(65) Prior Publication Data
US 2021/0387943 A1     Dec. 16, 2021

(30) Foreign Application Priority Data
Oct. 17, 2018 (JP) ................... 2018-196222

(51) Int. Cl.
*C07C 233/47* (2006.01)
*A61K 47/54* (2017.01)
*A61K 47/64* (2017.01)

(52) U.S. Cl.
CPC .......... *C07C 233/47* (2013.01); *A61K 47/543* (2017.08); *A61K 47/64* (2017.08)

(58) Field of Classification Search
CPC ...... C07C 233/47; A61K 47/543; A61K 47/64
See application file for complete search history.

(56) References Cited

U.S. PATENT DOCUMENTS

| 2003/0113262 A1 | 6/2003 | Ikeda et al. |
| 2010/0291672 A1 | 11/2010 | Takeoka et al. |
| 2016/0244405 A1 | 8/2016 | Alapati |

FOREIGN PATENT DOCUMENTS

| CN | 104356196 A | 2/2015 |
| JP | 2005-239549 A | 9/2005 |

(Continued)

OTHER PUBLICATIONS

Extended European Search Report dated Jun. 15, 2022, of counterpart European Patent Application No. 19872471.8.

(Continued)

*Primary Examiner* — Lyle Alexander
*Assistant Examiner* — Dwan A Gerido
(74) *Attorney, Agent, or Firm* — DLA Piper LLP (US)

(57) ABSTRACT

A carboxylic acid-type lipid can accelerate adhesion or aggregation of platelets even if the carboxylic acid-type lipid does not carry a protein involved in adhesion or aggregation of platelets or a peptide corresponding to an active site of the protein; a lipid particle and a lipid membrane each include the carboxylic acid-type lipid; and a platelet aggregation accelerating agent, a platelet adhesion accelerating agent, a hemostatic agent and a platelet substitute each include the carboxylic acid-type lipid, the lipid particle or the lipid membrane. A carboxylic acid-type lipid is selected from carboxylic acid-type lipids represented by formulas (I) to (VI), a lipid particle includes the carboxylic acid-type lipid, a lipid membrane includes the carboxylic acid-type lipid, (Continued)

and a platelet aggregation accelerating agent, a platelet adhesion accelerating agent, a hemostatic agent and a platelet substitute each include the carboxylic acid-type lipid, the lipid particle or the lipid membrane.

12 Claims, 13 Drawing Sheets

(56) References Cited

FOREIGN PATENT DOCUMENTS

| | | |
|---|---|---|
| WO | 98/07752 A1 | 2/1998 |
| WO | 01/64743 A1 | 9/2001 |
| WO | 2008/008523 A1 | 1/2008 |
| WO | 2008/062911 A1 | 5/2008 |

OTHER PUBLICATIONS

Notice of Reasons for Refusal dated Oct. 3, 2023, of counterpart Japanese Patent Application No. 2019-557516, along with an English translation.
Official Action dated Feb. 23, 2023, of counterpart Chinese Patent Application No. 201980068462.8., along with an English translation.
First Notice of Review Observations dated May 18, 2023, of counterpart Chinese Patent Application No. 201980068462.8, along with an English translation.
Zhou et al, "pH-Responsive Shrinkage/Swelling of a Supramolecular Hydrogel Composed of Two Small Amphiphilic Molecules," Chemistry, A European Journal, 11, pp. 1130-1136, 2005.
Jia et al, "The Effect of Environmental on the Recognition and Binding of Vancomycin to Native and Resistant Forms of Lipid II," Biophysical Journal, vol. 101, pp. 2684-2692, 2011.
Arai, M. et al., "Study on Liposome Composition of Platelet Substitutes with Haemostatic Ability," *Proceedings of the 32nd Annual Meeting of the Japanese Society for Biomaterials*, 2010, p. 324 along with an English translation.
Arai, M. et al., "Study on Liposome Composition of Platelet Substitutes with Haemostatic Ability (2nd Report)," *Proceedings of the 33rd Annual Meeting of the Japanese Society for Biomaterials*, 2011, p. 319 along with an English translation.
Sun, Q. et al., "A Collaborative Assembly Strategy for Tumor-Targeted siRNA Delivery," *Journal of the American Chemical Society*, 2015, vol. 137, pp. 6000-6010.
Waybrant, B. et al., "Effect of Polyethylene Glycol, Alkyl, and Oligonucleotide Spacers on the Binding, Secondary Structure, and Self-Assembly of Fractalkine Binding FKN-S2 Aptamer-Amphiphiles," *Langmuir*, 2014, vol. 30, pp. 7465-7474.
Shroff, K. et al., "Enhanced Integrin Mediated Signaling and Cell Cycle Progression on Fibronectin Mimetic Peptide Amphiphile Monolayers," *Langmuir*, 2012, vol. 28, pp. 1858-1865.
Ananthanarayanan, B. et al., "Neural stem cell adhesion and proliferation on phospholipid bilayers functionalized with RGD peptides," *Biomaterials*, 2010, vol. 31, pp. 8706-8715.
Obata, Y. et al., "Plasmid DNA-encapsulating liposomes: Effect of a spacer between the cationic head group and hydrophobic moieties of the lipids on gene expression efficiency," *Biochimica et Biophysica Acta*, 2009, vol. 1788, pp. 1148-1158.
Garg, A. et al., "Targeting colon cancer cells using PEGylated liposomes modified with a fibronectin-mimetic peptide," *International Journal of Pharmaceutics*, 2009, vol. 366, pp. 201-210.
Craig, J. A. et al., "Effect of Linker and Spacer on the Design of a Fibronectin-Mimetic Peptide Evaluated via Cell Studies and AFM Adhesion Forces," *Langmuir*, 2008, vol. 24, pp. 10282-10292.
Wang, K. et al., "Synthesis and in vitro Behavior of Multivalent Cationic Lipopeptide for DNA Delivery and Release in HeLa Cells," *Bioconjugate Chem.*, 2007, vol. 18, pp. 1735-1738.
Ochsenhirt, S. E. et al., "Effect of RGD secondary structure and the synergy site PHSRN on cell adhesion, spreading and specific integrin engagement," *Biomaterials*, 2006, vol. 27, pp. 3863-3874.
Marques, B. F. et al., "Sequence-Specific Binding of DNA to Liposomes Containing Di-Alkyl Peptide Nucleic Acid (PNA) Amphiphiles," *Langmuir*, 2005, vol. 21, pp. 2488-2494.
Schneider, J. et al., "Surface Force Measurements of Electrostatic and Hydrogen-Bonding Interactions between Bilayers of Glycine Amphiphiles," *Langmuir*, 2002, vol. 18, pp. 3923-3931.
Gore, T. et al., "Self-Assembly of Model Collagen Peptide Amphiphiles," *Langmuir*, 2001, vol. 17, pp. 5352-5360.
Pakalns, T. et al., "Cellular recognition of synthetic peptide amphiphiles in self-assembled monolayer films," *Biomaterials*, 1999, vol. 20, pp. 2265-2279.
Habermann, J. et al., "Fragment Condensation on Solid-Phase in the Synthesis of an Amphiphilic Glycopeptide from the Homophilic Recognition Domain of Epithelial Cadherin 1," *Tetrahedron Letters*, 1998, vol. 39, pp. 4797-4800.
Berndt, P. et al., "Synthetic Lipidation of Peptides and Amino Acids: Monolayer Structure and Properties," *J. Am. Chem. Soc.*, 1995, vol. 117, pp. 9515-9522.
Haverstick, K. et al., "Targeted Cell Interactions with Surfaces Incorporating Synthetic Peptide Amphiphiles," *Polymeric Materials Science and Engineering*, 1997, vol. 77, pp. 584-585.
Office Action dated Nov. 29, 2022, of counterpart Chinese Patent Application No. 201980068462.8, along with an English translation.
J. Qu et al., "Synthesis and Properties of DNA Complexes Containing 2,2,6,6-Tetramethyl-1-piperindinoxy (TEMPO) Moieties as Organic Radical Battery Materials," Wiley-VCH Verlag GmbH & Co. KGaA, Weinheim, Chem. Eur. J, pp. 3250-3259, 2008, in English.

CARBOXYLIC ACID-TYPE LIPID, AND LIPID PARTICLE AND LIPID MEMBRANE EACH COMPRISING CARBOXYLIC ACID-TYPE LIPID

TECHNICAL FIELD

This disclosure relates to a carboxylic acid-type lipid; a lipid particle and a lipid membrane each comprising the carboxylic acid-type lipid; and a platelet aggregation accelerating agent, a platelet adhesion accelerating agent, a hemostatic agent and a platelet substitute each comprising the carboxylic acid-type lipid, the lipid particle or the lipid membrane.

BACKGROUND

Platelets play a central role in hemostasis, and adhesion of platelets in blood to blood vessels or aggregation of platelets in blood acts as an important trigger for hemostasis. To compensate for decreased platelet counts or platelet dysfunction, or prepare for massive bleeding, a pseudo-platelet (platelet substitute) is often attempted to be artificially produced. As such a platelet substitute, for example, a lipid microparticle carrying a protein involved in adhesion to blood vessel walls or platelet-platelet aggregation that exists on the platelet membrane surface, a protein that mediates platelet-platelet aggregation, or a peptide corresponding to an active site of such a protein has been attempted to be produced. Since the system of GPIb, which is a glycoprotein existing on a membrane surface, and von Willebrand factor (vWF), which is a plasma protein, or the system of GPIIb/III and fibrinogen plays a central role in adhesion or aggregation of platelets, it is known that a lipid particle having GPIb on the surface (WO 01/064743) and a lipid particle carrying a fibrinogen-derived dodecapeptide (H12) on the surface (JP 2005-239549 A, Proceedings of the 32nd Annual Meeting of the Japanese Society for Biomaterials, p. 324 and Proceedings of the 33rd Annual Meeting of the Japanese Society for Biomaterials, p. 319) can be used as a substitute for platelets.

It is also known that both of a lipid particle including a carboxylic acid-type lipid, a phospholipid and cholesterol and not having the H12 peptide on the surface and a lipid particle including a carboxylic acid-type lipid, a phospholipid and cholesterol and having the H12 peptide on the surface have a platelet aggregation accelerating effect, while the lipid particle not having the H12 peptide on the surface has a smaller platelet aggregation accelerating effect compared to the lipid particle having the H12 peptide on the surface (Proceedings of the 33rd Annual Meeting of the Japanese Society for Biomaterials, p. 319).

It could therefore be helpful to provide a carboxylic acid-type lipid that can accelerate adhesion or aggregation of platelets even if the carboxylic acid-type lipid does not carry a protein involved in adhesion or aggregation of platelets such as GPIb and H12, or a peptide corresponding to an active site of the protein; a lipid particle and a lipid membrane each comprising the carboxylic acid-type lipid; and a platelet aggregation accelerating agent, a platelet adhesion accelerating agent, a hemostatic agent and a platelet substitute each comprising the carboxylic acid-type lipid, the lipid particle or the lipid membrane.

SUMMARY

We thus provide:
[1] A carboxylic acid-type lipid selected from carboxylic acid-type lipids represented by formulas (I) to (VI):

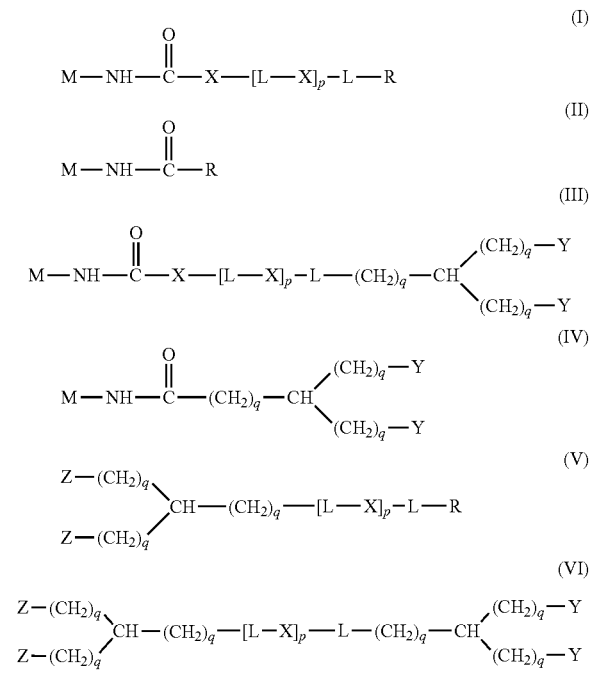

wherein, in formulas (I) to (VI),
M represents an amino acid residue, an amino acid derivative residue, a peptide residue or a salt thereof, wherein the amino acid residue, the amino acid derivative residue, the peptide residue and the salt thereof can be negatively charged at physiological pH,
R represents a hydrocarbon group,
L represents —CO—O—, —O—CO—, —CO—NH—, —NH—CO—, —CO—S—, —S—CO— or —S—S—,
X represents a hydrocarbon group, a neutral amino acid residue or a polyalkylene glycol residue,
p represents an integer of 0 or more,
q represents an integer of 0 or more,
Y represents a branched chain composed of a branched chain body and one or more groups Y2 that are bonded to the branched chain body, or represents a straight chain composed of one group Y2, wherein the branched chain body is composed of one or more units Y1, wherein each unit Y1 is represented by formula (VII):

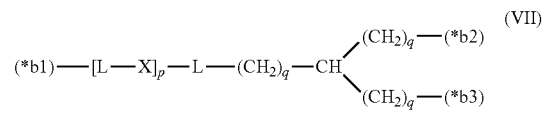

and wherein each group Y2 is represented by formula (VIII):

wherein, in formulas (VII) and (VIII),
R, L, X, p and q are the same as defined above,
(*b1), (*b2) and (*b3) represent a bond of each unit Y1,
(*b4) represents a bond of each group Y2, the bond (*b1) of each unit Y1 is bonded to $(CH_2)_q$ in formula (III), (IV) or (VI), or is bonded to
a bond (*b2) or (*b3) of another unit Y1 constituting the branched chain body, and
the bond (*b4) of each group Y2 is bonded to $(CH_2)_q$ in formula (III), (IV) or (VI), or is bonded to a bond (*b2) or (*b3) of any unit Y1 constituting the branched chain body,
Z represents a branched chain composed of a branched chain body and one or more groups Z2 that are bonded to the branched chain body, or represents a straight chain composed of one group Z2, wherein the branched chain body is composed of one or more units Z1, wherein each unit Z1 is represented by formula (IX):

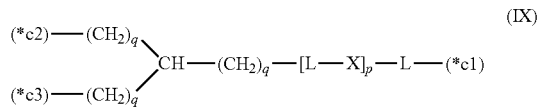

and wherein each group Z2 is selected from groups represented by formulas (X) and (XI):

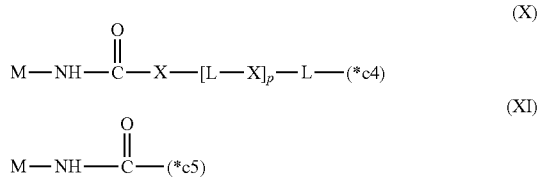

wherein, in formulas (IX), (X) and (XI),
M, L, X, p and q are the same as defined above,
(*c1), (*c2) and (*c3) represent a bond of each unit Z1,
(*c4) and (*c5) represent a bond of each group Z2,
the bond (*c1) of each unit Z1 is bonded to $(CH_2)_q$ in formula (V) or (VI), or is bonded to a bond (*c2) or (*c3) of another unit Z1 constituting the branched chain body, and
the bond (*c4) or (*c5) of each group Z2 is bonded to $(CH_2)_q$ in formula (V) or (VI), or is bonded to a bond (*c2) or (*c3) of any unit Z1 constituting the branched chain body.
[2] The carboxylic acid-type lipid according to [1], wherein the amino acid residue represented by M is an acidic amino acid residue or a neutral amino acid residue.
[3] The carboxylic acid-type lipid according to [2], wherein the acidic amino acid residue is an aspartic acid residue or a glutamic acid residue.
[4] The carboxylic acid-type lipid according to [1], wherein the residue of the amino acid derivative represented by M is a residue of a basic amino acid derivative, and
an introduced derivatization that the basic amino acid derivative comprises is amidation of an amino group of a side chain of a basic amino acid to a group represented by the formula: $-NH-CO-R_1$ wherein $-NH-$ is derived from the amino group of the side chain of the basic amino acid, and $R_1$ represents a hydrocarbon group.
[5] The carboxylic acid-type lipid according to [1], wherein the peptide residue represented by M is a peptide residue composed of two to seven amino acid residues.

[6] The carboxylic acid-type lipid according to [1] or [5], wherein the peptide residue represented by M is a peptide residue comprising one or two or more acidic amino acid residues.
[7] The carboxylic acid-type lipid according to [6], wherein the peptide residue represented by M is a peptide residue comprising two or more acidic amino acid residues selected from an aspartic acid residue and a glutamic acid residue.
[8] The carboxylic acid-type lipid according to [7], wherein the peptide residue represented by M is a peptide residue represented by formula (XII):

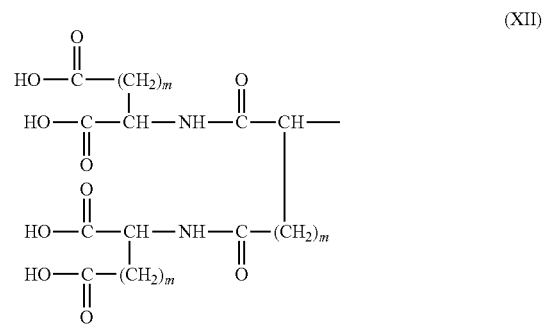

wherein m is the same or different and represents 1 or 2.
[9] The carboxylic acid-type lipid according to any one of [1] to [8], wherein the salt is selected from a sodium salt, a potassium salt, a calcium salt and a magnesium salt.
[10] The carboxylic acid-type lipid according to any one of [1] to [9], wherein L is the same or different and represents $-CO-O-$, $-O-CO-$, $-CO-NH-$ or $-NH-CO-$.
[11] The carboxylic acid-type lipid according to any one of [1] to [10], wherein Y is selected from straight and branched chains represented by formulas (XIII), (XIV), (XV) and (XVI):

wherein, in formulas (XIII) to (XVI),
Y1 represents one unit Y1,
Y2 represents one group Y2, and
(*b) represents a bond of the unit Y1 bonded to $(CH_2)_q$ in formula (III), (IV) or (VI).

[12] The carboxylic acid-type lipid according to any one of [1] to [11], wherein Z is selected from straight and branched chains represented by formulas (XVII), (XVIII), (XIX) and (XX):

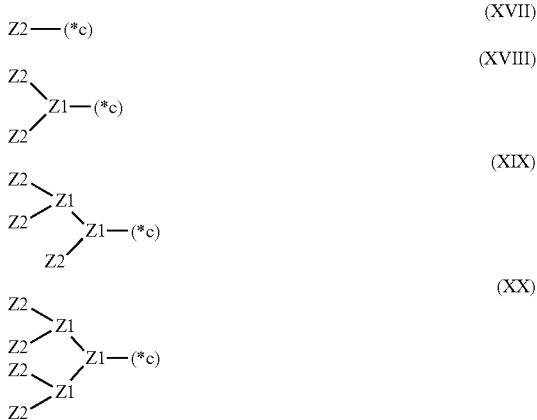

wherein, in formulas (XVII) to (XX),
Z1 represents one unit Z1,
Z2 represents one group Z2, and
(*c) represents a bond of the unit Z1 bonded to $(CH_2)_q$ in formula (V) or (VI).

[13] A lipid particle, comprising the carboxylic acid-type lipid according to any one of [1] to [12].
[14] The lipid particle according to [13], wherein the lipid particle further comprises one or two or more lipids selected from a phospholipid and a sterol.
[15] The lipid particle according to [13] or [14], wherein a surface of the lipid particle is negatively charged at physiological pH.
[16] The lipid particle according to [15], wherein the lipid particle has a zeta potential of −12 mV or less under a physiological condition.
[17] The lipid particle according to any one of [13] to [16], wherein the lipid particle has a mean particle diameter of 30 to 5,000 nm.
[18] The lipid particle according to any one of [13] to [17], wherein the lipid particle has a form selected from a liposome, a micelle, a nanosphere, a microsphere, a nanocrystal and a microcrystal.
[19] A lipid membrane, comprising the carboxylic acid-type lipid according to any one of [1] to [12].
[20] The lipid particle according to [19], wherein the lipid membrane further comprises one or two or more lipids selected from a phospholipid and a sterol.
[21] The lipid membrane according to [19] or [20], wherein a surface of the lipid membrane is negatively charged at physiological pH.
[22] The lipid membrane according to any one of [19] to [21], wherein the lipid membrane has a thickness of 10 to 1,000 nm.
[23] A platelet aggregation accelerating agent, comprising the carboxylic acid-type lipid according to any one of [1] to [12], the lipid particle according to any one of [13] to [18] or the lipid membrane according to any one of [19] to [22].
[24] A platelet adhesion accelerating agent, comprising the carboxylic acid-type lipid according to any one of [1] to [12], the lipid particle according to any one of [13] to [18] or the lipid membrane according to any one of [19] to [22].
[25] A hemostatic agent, comprising the carboxylic acid-type lipid according to any one of [1] to [12], the lipid particle according to any one of [13] to [18] or the lipid membrane according to any one of [19] to [22].
[26] A platelet substitute, comprising the carboxylic acid-type lipid according to any one of [1] to [12], the lipid particle according to any one of [13] to [18] or the lipid membrane according to any one of [19] to [22].

We thus provide a carboxylic acid-type lipid that can accelerate adhesion and/or aggregation of platelets even if the carboxylic acid-type lipid does not carry a protein involved in adhesion or aggregation of platelets such as GPIb and H12, or a peptide corresponding to an active site of the protein, and that in turn can be used as a platelet substitute (artificial platelet); a lipid particle and a lipid membrane each comprising the carboxylic acid-type lipid; and a platelet aggregation accelerating agent, a platelet adhesion accelerating agent, a hemostatic agent and a platelet substitute (artificial platelet) each comprising the carboxylic acid-type lipid, the lipid particle or the lipid membrane. The carboxylic acid-type lipid is an anionic lipid that is negatively charged at physiological pH. Each of the lipid particle and the lipid membrane comprises the carboxylic acid-type lipid, and the surfaces of the lipid particle and the lipid membrane are negatively charged at physiological pH. Without carrying a known protein constituting the GPIb-vWF system or the GPIIb/III-fibrinogen system, or a peptide corresponding to an active site of the protein, the carboxylic acid-type lipid, the lipid particle and the lipid membrane can accelerate adhesion and/or aggregation of platelets by binding to a plurality of platelets. Particularly, the carboxylic acid-type lipid, the lipid particle and the lipid membrane can make activated platelets aggregate more selectively, and thus exhibit preferable properties as a platelet substitute without activating platelets in a resting state more than necessary even in systemic administration such as intravenous administration. Therefore, the carboxylic acid-type lipid, the lipid particle and the lipid membrane are particularly useful as a hemostatic agent and a platelet substitute (artificial platelet).

DETAILED DESCRIPTION

Figure 1:
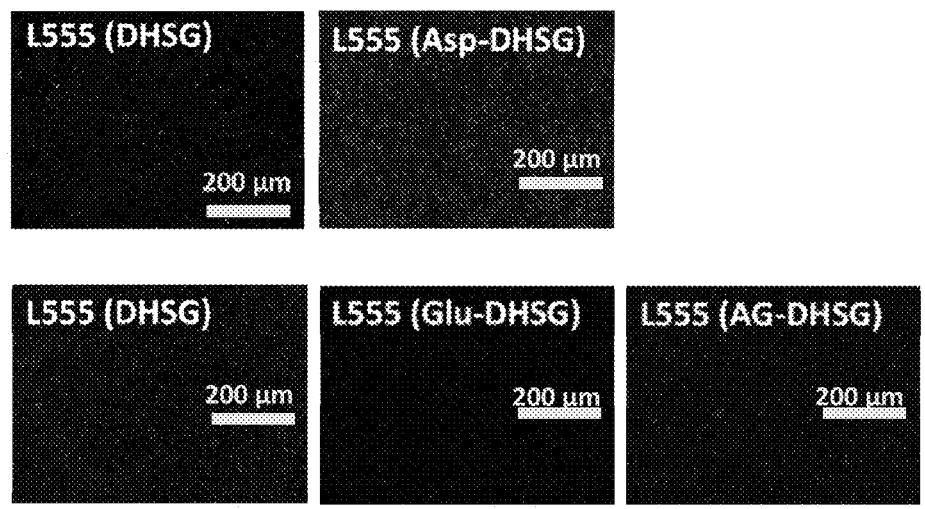
FIG. 1 shows observation results of fluorescently labeled liposomes in platelet aggregates (top of FIG. 1: fluorescence micrographs of platelet aggregates obtained by using a DiO-labeled liposome dispersion liquid, bottom of FIG. 1: fluorescence micrographs of platelet aggregates obtained by using a DiD-labeled liposome dispersion liquid).

Our lipids, particles and membranes will be described in detail. "Numerical value A to numerical value B" means numerical value A or more and numerical value B or less.

Lipid Particle and Lipid Membrane

The lipid particle is a particle comprising a lipid. The lipid membrane is a membrane comprising a lipid. The lipid is an organic molecule having a hydrophilic moiety and a hydrophobic moiety, and the lipid includes a simple lipid, a complex lipid, a derived lipid and the like. The lipid may be modified by a hydrophilic polymer or the like. Examples of the hydrophilic polymer include polyethylene glycol (PEG), polyglycerin, polypropylene glycol, polyvinyl alcohol, styrene-maleic anhydride alternating copolymer, polyvinylpyrrolidone, synthetic polyamino acid and the like.

Each of the lipid particle and the lipid membrane comprises one or two or more carboxylic acid-type lipids selected from carboxylic acid-type lipids (I) to (VI). The carboxylic acid-type lipids (I) to (VI) will be mentioned later. The carboxylic acid-type lipids (I) to (VI) are anionic lipids that are negatively charged at physiological pH. Therefore, when the carboxylic acid-type lipids (I) to (VI) come into contact with blood and are hydrated by moisture in the blood, they become negatively charged.

When the lipid particle and the lipid membrane come into contact with blood, the carboxylic acid-type lipid included in the lipid particle and the lipid membrane becomes negatively charged. The negatively charged carboxylic acid-type lipid can bind to a plurality of platelets (particularly, activated platelets) and can accelerate adhesion and/or aggregation of platelets, and in turn can accelerate blood coagulation. As a result of this, the lipid particle and the lipid membrane can accelerate the hemostatic effect of blood. The hemostatic effect of the lipid particle and the lipid membrane is exerted by the platelet adhesion accelerating effect and/or the platelet aggregation accelerating effect of the carboxylic acid-type lipid.

The lipid particle may form a lipid particle aggregate. The description of the lipid particle used herein is also applied to a lipid particle constituting the lipid particle aggregate unless otherwise specified.

Irregularities may be formed on the surface of the lipid membrane. For example, the lipid membrane may be composed of: a lipid membrane having a flat surface; and a lipid particle supported on the flat surface of the lipid membrane and/or a lipid particle aggregate supported on the flat surface of the lipid membrane, and such a lipid membrane corresponds to a lipid membrane having irregularities on the surface.

After coming into contact with blood, the lipid membrane may or may not maintain the form of a membrane. When the lipid membrane maintains the form of a membrane after coming into contact with blood, the abovementioned effect is exerted by the carboxylic acid-type lipid included in the lipid membrane. Examples of when the lipid membrane does not maintain the form of a membrane after coming into contact with blood include when a part of or the whole of the lipid membrane is hydrated by moisture in blood to form a lipid particle and the lipid particle thus formed is released from the base. When apart of the lipid membrane is hydrated by moisture in blood to form a lipid particle and the lipid particle thus formed is released from the base, the abovementioned effect is exerted by the carboxylic acid-type lipid included in the lipid particle and the carboxylic acid-type lipid included in the remaining lipid membrane. When the whole of the lipid membrane is hydrated by moisture in blood to form a lipid particle and the lipid particle thus formed is released from the base, the abovementioned effect is exerted by the carboxylic acid-type lipid included in the lipid particle. A lipid particle is formed from a part of or the whole of the lipid membrane, and the lipid particle thus formed is released from the base, resulting in an increased opportunity for the carboxylic acid-type lipid to act on platelets, and thus the abovementioned effect is more effectively exerted. The lipid particle also includes a lipid particle formed from the lipid membrane, and the description of the lipid particle used herein is also applied to the lipid particle formed from the lipid membrane unless otherwise specified.

The lipid particle and the lipid membrane may include one or two or more other anionic lipids. The anionic lipid has a group that is negatively charged at physiological pH as a part of a hydrophilic moiety. Therefore, when the anionic lipid comes into contact with blood and is hydrated by moisture in the blood, it becomes negatively charged. Examples of the group that is negatively charged at physiological pH include a phosphoric acid group, a carboxyl group, a sulfo group, a nitro group, a salt thereof and the like. The physiological pH is usually pH 5.5 to 9.0, preferably pH 6.5 to 8.0, and more preferably pH 7.0 to 7.8. Examples of the anionic lipid include a carboxylic acid-type lipid other than the carboxylic acid-type lipids (I) to (VI), an acidic phospholipid, a fatty acid, a ganglioside, an acidic amino acid-based surfactant and the like.

The shape of the lipid particle is not particularly limited. Examples of the shape of the lipid particle include a spherical shape (a true spherical shape, an elliptic spherical shape or the like), an indefinite shape and the like. When the lipid particle is a crystallite such as a nanocrystal and a microcrystal, the crystallite has a definite crystal shape.

The mean particle diameter of the lipid particle is not particularly limited. The mean particle diameter of the lipid particle is preferably 30 to 5,000 nm, more preferably 50 to 1,000 nm, and still more preferably 70 to 400 nm. The mean particle diameter as used herein is a numerical value measured by dynamic light scattering. Dynamic light scattering can be performed using Zetasizer nano (manufactured by Malvern Panalytical Ltd.). At that time, it is possible to use a dispersion liquid having the concentration of the lipid particle of 0.1 mg/mL that was prepared using PBS as a dispersion medium. The measurement temperature is, for example, 25° C. The scattering angle is, for example, 90 degrees. The particle diameter can be adjusted by, for example, using the extrusion method, the French press method and the like.

The lipid particle may be a monodisperse particle or a polydisperse particle, and is preferably a monodisperse particle. To obtain a monodisperse lipid particle, it is preferable to adjust the particle diameter of the lipid particle to a certain range by treatment such as homogenization and extrusion.

The form of the lipid particle is not particularly limited. Examples of the form of the lipid particle include a liposome, a micelle, a nanosphere, a microsphere (e.g., a lipid microsphere), a nanocrystal, a microcrystal and the like. Of these forms, a liposome is preferable. Examples of the liposome include a multilamellar vesicle (MLV), a small unilamellar vesicle (SUV), a large unilamellar vesicle and the like. The lipid particle also includes a lipid particle in which the inside of the particle is solid (i.e., the inside of the particle is packed with components) not having a lipid bilayer structure (lamella structure) like a liposome. Examples of such form include a form having a core of a hydrophobic polymer (preferably, a hydrophobic biodegradable polymer) and a lipid layer covering the core.

The form of the lipid particle can be confirmed by electron microscopy (e.g., cryo-transmission electron microscopy (CryoTEM method)), structural analysis using X-rays (e.g., small-angle X-ray scattering (SAXS) measurement) and the like.

The liposome is a lipid vesicle formed from a lipid bilayer membrane including a lipid molecule, specifically, a closed vesicle having space (internal phase) separated from the external environment by a lipid bilayer membrane occurring based on the polarity of a hydrophobic group and a hydrophilic group of a lipid molecule. The internal phase of the liposome includes a dispersion medium (e.g., an aqueous medium such as water) used during the production of the liposome. When the lipid bilayer membrane is defined as one layer, the number of layers of the lipid bilayer membrane possessed by the liposome is preferably 1 to 4, and more preferably 1 to 2.

The number of layers of the lipid bilayer membrane can be controlled by a pore diameter of a filter and a dispersion medium (pH, temperature, ionic strength) of a vesicle. Examples of the method of measuring the number of layers include the freeze-fracture method, small-angle X-ray scattering, electron spin resonance (ESR) using a spin-labeled lipid, a measurement method using $^{31}$P-NMR, a measurement method using 6-p-toluidino-2-naphthalenesulfonic acid (TNS) and the like.

The internal phase of the liposome may include a drug. The drug included in the internal phase of the liposome is preferably a drug that is physiologically or pharmacologically effective by being accumulated in a vascular injury site, and examples thereof include a platelet aggregation initiator, a blood coagulant, a thrombolytic agent, an antiplatelet agent, an anticoagulant, a vasoconstrictor, an anti-inflammatory agent and the like. Since the lipid particle has a property of accumulating in a site of a living body in which activated platelets are accumulated, namely, a site where a thrombus is formed, a drug that enhances the thrombus formation at the site (e.g., a platelet aggregation initiator, a blood coagulant and the like) or, conversely, a drug that dissolves a thrombus or weakens the degree (e.g., a thrombolytic agent, an antiplatelet agent, an anticoagulant and the like) is particularly preferably used. Encapsulation of a water-soluble drug can be performed using, for example, the hydration method, the extrusion method, the ethanol injection method, the reverse phase evaporation method, the freeze-thawing method and the like. Encapsulation of a lipophilic drug can be performed using, for example, the Bangham method, the mechanochemical method, the supercritical carbon dioxide method, the film loading method and the like. Encapsulation of a dissociative drug can be performed using, for example, the pH gradient (remote loading) method, the counterion concentration gradient method and the like.

Examples of the platelet aggregation initiator include adenosine diphosphate (ADP), collagen, a collagen-derived peptide, convulxin, serotonin, epinephrine, vasopressin, carbazochrome, a blood coagulation factor (e.g., FVIII, FIX), thrombin, an antiplasmin agent (e.g., epsilon-aminocaproic acid, tranexamic acid), ethamsylate, phytonadione, conjugated estrogen (e.g., sodium estrone sulfate, sodium equilin sulfate) and the like.

Examples of the blood coagulation accelerating agent include fibrinogen, thrombin, a blood coagulation factor (e.g., FXa), protamine sulfate and the like.

Examples of the thrombolytic agent include urokinase, plasmin, plasminogen activator and the like.

Examples of the antiplatelet agent include cilostazol, sarpogrelate, Epadel, Persantin, Plavix, ticlopidine, prasugrel, limaprost, PGE1 and a derivative thereof, prostacyclin and a derivative thereof and the like.

Examples of the anticoagulant include heparin, low-molecular-weight heparin, warfarin, a non-vitamin K antagonist oral anticoagulant (NOAC) and the like.

Examples of the vasoconstrictor include noradrenaline, norfenefrine, phenylephrine, metaraminol, methoxamine, prostaglandin $F_1\alpha$, prostaglandin $F_2\alpha$, thromboxane $A_2$ and the like.

Examples of the anti-inflammatory agent include a steroidal anti-inflammatory agent (e.g., dexamethasone, hydrocortisone, prednisolone, betamethasone, triamcinolone, methylprednisolone), a nonsteroidal anti-inflammatory agent (e.g., indomethacin, acemetacin, flurbiprofen, aspirin, ibuprofen, flufenamic acid, ketoprofen) and the like.

The thickness of the lipid membrane is preferably 10 to 1,000 nm, more preferably 30 to 500 nm, and still more preferably 60 to 240 nm. The method of measuring the lipid membrane is as follows. The lipid membrane is observed with a scanning electron microscope (SEM). The thickness of five points optionally selected in the SEM observation image is measured, and the mean is regarded as the thickness of the lipid membrane.

The lipid particle and the lipid membrane may include one or two or more components other than a lipid. Examples of the other components include a surfactant, a protein, a peptide, an antioxidant, an antiseptic, a pH adjuster, triglyceride, a biodegradable polymer such as polylactic acid, a dispersion medium used for production of the lipid particle or the lipid membrane and the like.

Examples of the surfactant include an anionic surfactant, an amphoteric surfactant, a nonionic surfactant and the like.

Examples of the anionic surfactant include carboxylic acid type, sulfonic acid type, sulfuric acid ester type, phosphoric acid ester type and the like. Specific examples thereof include α-acyl sulfonate, alkyl sulfonate, alkyl aryl sulfonate, alkyl naphthalene sulfonate, alkyl sulfate, alkyl ether sulfate, alkylamide sulfate, polyoxyethylene alkyl ether sulfate, polyoxyethylene alkylamide ether sulfate, alkyl phosphate, alkylamide phosphate, alkyloylalkyl taurine salt, N-acyl amino acid salt, sulfosuccinate, perfluoroalkyl phosphoric acid ester and the like.

Examples of the amphoteric surfactant include glycine type, aminopropionic acid type, carboxybetaine type, sulfobetaine type, phosphocholine type and the like. Specific examples thereof include 2-alkyl-N-carboxymethyl-N-hydroxyethyl imidazolinium betaine, coconut oil fatty acid amide propyl betaine and the like.

Examples of the nonionic surfactant include ester type, ether type, ester ether type, alkanolamide type and the like. Specific examples thereof include fatty acid alkanolamide, polyoxyethylene hardened castor oil, polyoxyethylene sorbitan fatty acid ester, polyoxyethylene alkyl ether, polyoxyethylene alkyl ester, sucrose fatty acid ester, polyglycerin fatty acid ester, alkyl amine oxide and the like.

Examples of the protein include a ligand, a receptor, an antibody and the like, each of which has directivity to a target molecule in cells, tissues and the like. These proteins may exist in the lipid bilayer membrane, or may exist on the surface of the lipid particle or the lipid membrane. These proteins may bind to the lipid particle and the lipid membrane via a so-called spacer, linker and the like.

Examples of such protein include a protein recognizing an activated platelet, a vascular injury site and/or an inflammatory tissue. A substance recognizing an activated platelet, a vascular injury site and/or an inflammatory tissue is, for example, a substance that acts to recognize an activated platelet, a vascular injury site and/or an inflammatory tissue to direct the lipid particle and the lipid membrane to the activated platelet, the vascular injury site and/or the inflammatory tissue and accumulate the lipid particle and the lipid membrane in these sites. Examples of the recognition substance include a substance that is incorporated into an aggregate of an activated platelet and/or a white blood cell and a substance that is accumulated in a vascular injury site and/or an inflammatory tissue after recognizing integrin or selectin exposed on an activated platelet, collagen exposed on a vascular injury site, von Willebrand factor bound to collagen exposed on a vascular injury site, selectin exposed on an inflammatory tissue and/or a selectin ligand exposed on a white blood cell and the like. Specific examples of the recognition substance include H12 (HHLGGAKQAGDV), GPIbα, GPIa/IIa (integrin α2β1), GPVI, MAC-1, fibrinogen, P-selectin, PSGL-1 and the like. Without carrying a protein involved in adhesion or aggregation of platelets such as GPIb and H12, or a peptide corresponding to an active site of the protein, the lipid particle and the lipid membrane can accelerate aggregation of platelets. Therefore, regarding the lipid particle and the lipid membrane, it is preferable that the surface is not chemically modified by GPIb, H12 or the like, in terms of reducing the production step, the production cost and the like.

As long as the desired effect of the lipid particle and the lipid membrane is achieved, the recognition substance may be a variant of a natural recognition substance in which one or a plurality of amino acids are deleted, substituted, inserted or added in an amino acid sequence of the natural recognition substance, and examples of such variant include a substitution product, an analog, a mutant, a modification product, a derivative, a glycosylation product and the like of the natural recognition substance.

Examples of the antioxidant include ascorbic acid, uric acid, a tocopherol homolog such as vitamin E and the like. As the tocopherol, four types of isomers including α-, β-, γ- and σ-isomers exist, and all of them are included in the lipid particle and the lipid membrane.

Examples of the antiseptic include propyl p-hydroxybenzoate, ethyl p-hydroxybenzoate, methyl p-hydroxybenzoate, bronopol and the like.

Examples of the pH adjuster include a phosphate buffer and the like.

It is preferable that the surfaces of the lipid particle, the lipid particle aggregate and the lipid membrane are negatively charged at physiological pH. As a result of this, when the surfaces of the lipid particle, the lipid particle aggregate and the lipid membrane come into contact with blood and are hydrated by moisture in the blood, they become negatively charged.

In the lipid particle before coming into contact with blood, a hydrophilic moiety of the carboxylic acid-type lipid may or may not be located in the surface side of the lipid particle. When the hydrophilic moiety of the carboxylic acid-type lipid is located in the surface side of the lipid particle in the lipid particle before coming into contact with blood, in the lipid particle after coming into contact with blood, the hydrophilic moiety of the carboxylic acid-type lipid is also located in the surface side of the lipid particle. Even when the hydrophilic moiety of the carboxylic acid-type lipid is not located in the surface side of the lipid particle in the lipid particle before coming into contact with blood, after coming into contact with blood, the lipid particle is reconstituted and, as a result, the hydrophilic moiety of the carboxylic acid-type lipid can be located in the surface side of the lipid particle. As a result of the fact that the hydrophilic moiety of the carboxylic acid-type lipid is located in the surface side of the lipid particle, the surface of the lipid particle becomes likely to be negatively charged at physiological pH (i.e., when it comes into contact with blood and is hydrated by moisture in the blood, it becomes likely to be negatively charged).

In the lipid membrane before coming into contact with blood, the hydrophilic moiety of the carboxylic acid-type lipid may or may not be located in the surface side of the lipid membrane. When the hydrophilic moiety of the carboxylic acid-type lipid is located in the surface side of the lipid membrane in the lipid membrane before coming into contact with blood, in the lipid membrane remaining after coming into contact with blood, the hydrophilic moiety of the carboxylic acid-type lipid is also located in the surface side of the lipid particle. Even when the hydrophilic moiety of the carboxylic acid-type lipid is not located in the surface side of the lipid particle in the lipid membrane before coming into contact with blood, after coming into contact with blood, the lipid membrane is reconstituted and, as a result, the hydrophilic moiety of the carboxylic acid-type lipid can be located in the surface side of the lipid membrane. As a result of the fact that the hydrophilic moiety of the carboxylic acid-type lipid is located in the surface side of the lipid membrane, the surface of the lipid membrane becomes likely to be negatively charged at physiological pH (i.e., when it comes into contact with blood and is hydrated by moisture in the blood, it becomes likely to be negatively charged). Even when the hydrophilic moiety of the carboxylic acid-type lipid is or is not located in the surface side of the lipid membrane in the lipid membrane before coming into contact with blood, in the lipid particle formed from the lipid membrane, the hydrophilic moiety of the carboxylic acid-type lipid is located in the surface side of the lipid particle.

The degree of negative charge at physiological pH of the surface of the lipid particle or the lipid particle aggregate can be evaluated based on a zeta potential (surface potential) of the lipid particle or the lipid particle aggregate under a physiological condition. The physiological condition is a condition in which usually pH is 5.5 to 9.0, preferably pH is 6.5 to 8.0, and more preferably pH is 7.0 to 7.8, and the ionic strength is usually 0.05 to 0.30, preferably 0.10 to 0.20, and more preferably 0.14 to 0.16.

The zeta potential (surface potential) of the lipid particle or the lipid particle aggregate under a physiological condition is preferably −12 mV or less, more preferably −15 mV or less, and still more preferably −18 mV or less. The lower limit of the zeta potential of the lipid particle or the lipid particle aggregate under a physiological condition is not particularly limited. The zeta potential of the lipid particle or the lipid particle aggregate under a physiological condition is preferably −80 mV or more, more preferably −50 mV or more, and still more preferably −45 mV or more. The upper limit and the lower limit mentioned herein can be appropriately combined. The zeta potential as used herein is a numerical value measured by electrophoretic light scattering. Electrophoretic light scattering can be performed using Zetasizer nano (manufactured by Malvern Panalytical Ltd.). At that time, it is possible to use a dispersion liquid having the concentration of the lipid particle of 0.1 mg/mL that was prepared using PBS as a dispersion medium. The measurement condition is, for example, a condition in which pH is 7.4, the ionic strength is 0.153, and the temperature is 25° C.

A method of producing the lipid particle and the lipid particle aggregate can be appropriately selected according to the form of the lipid particle and the lipid particle aggregate. Examples of the method of producing the lipid particle and the lipid particle aggregate include the thin film method, the reverse phase evaporation method, the ethanol injection method, the ether injection method, the dehydration-rehydration method, the surfactant dialysis method, the surfactant removal method, the hydration method, the freeze-thawing method, the ultrasonic wave method, the extrusion method, the high-pressure emulsification method and the like.

When the lipid particle is produced, examples of the dispersion medium in which the lipid particle is dispersed include an aqueous medium and the like. Examples of the aqueous medium include, in addition to water, those in which other components such as a salt are added to water, for example, buffers such as a phosphate buffer, a citrate buffer and phosphate-buffered saline, physiological saline, a cell culture medium and the like.

The lipid membrane can be formed on the surface of a base by attaching an appropriate amount of a solution of a lipid at an appropriate concentration to the base, followed by drying. The base is not particularly limited as long as it can form the lipid membrane. As a solvent in which a lipid is dissolved, for example, it is possible to use organic solvents such as ethyl alcohol, isopropyl alcohol, tert-butyl alcohol and diethyl ether. As a method of attaching a solution to a base, for example, it is possible to use the spraying method, the falling drop method, the dipping method, the applying method and the like. As a drying method, for example, it is possible to use freeze-drying, natural drying, drying by heating, drying under reduced pressure and the like. The concentration of a lipid can be selected in a range of 0.1 mg/mL to 100 mg/mL according to the solubility in the solvent and the membrane thickness of the lipid membrane obtained. The amount of a solution attached to a base can be appropriately adjusted according to the membrane thickness of the lipid membrane and the like. Usually, when an anionic lipid is dissolved in an organic solvent, it is dissolved as an acid type. When the anionic lipid is a salt type such as a sodium salt, since the solubility in an organic solvent is greatly decreased, an undissolved lipid is dispersed as an amorphous fine powder or a lipid particle in a form of a crystallite. When this is supported on a base in the same manner as the abovementioned method, a lipid particle is supported on the surface of the base. In this example, the lipid particle may be supported in a state in which a lipid membrane derived from a lipid dissolved in an organic solvent coexists, or may be supported in a state in which an aggregate of the lipid particle further coexists.

The surfaces of the lipid particle and the lipid membrane may be modified by a hydrophilic polymer or the like. Examples of the hydrophilic polymer include polyethylene glycol (PEG), polyglycerin, polypropylene glycol, polyvinyl alcohol, styrene-maleic anhydride alternating copolymer, polyvinylpyrrolidone, synthetic polyamino acid and the like. Regarding these hydrophilic polymers, one hydrophilic polymer may be used alone, or two or more hydrophilic polymers may be used in combination.

Carboxylic Acid-Type Lipid

Each of the lipid particle and the lipid membrane comprises one or two or more carboxylic acid-type lipids selected from carboxylic acid-type lipids (I) to (VI). Hereinafter, the carboxylic acid-type lipids (I) to (VI) are sometimes collectively referred to as "carboxylic acid-type lipid." When the carboxylic acid-type lipid is included in the lipid particle or the lipid membrane will be mainly described. The carboxylic acid-type lipid may be included in a lipid structure in other forms, and the following description is also applicable to when the carboxylic acid-type lipid is included in a lipid structure in other forms.

The carboxylic acid-type lipid has a hydrophilic moiety and a hydrophobic moiety, and the hydrophilic moiety has a carboxyl group or a salt thereof. The carboxylic acid-type lipid is an anionic lipid, and a carboxyl group or a salt thereof existing in the hydrophilic moiety is ionized at physiological pH and negatively charged. Therefore, when the lipid particle and the lipid membrane come into contact with blood and are hydrated by moisture in the blood, the surfaces of the lipid particle and the lipid membrane are negatively charged. As a result of this, at least a part of the lipid particle and the lipid membrane can bind to a plurality of platelets (particularly, activated platelets) via an electrostatic interaction and can accelerate aggregation of platelets, and in turn can accelerate blood coagulation. This does not mean that the platelet adhesion accelerating effect and/or the platelet aggregation accelerating effect evoked by the lipid particle and the lipid membrane cannot be involved in an interaction other than an electrostatic interaction such as the van der Waals force.

The content of the carboxylic acid-type lipid is not particularly limited as long as the surfaces of the lipid particle and the lipid membrane are negatively charged at physiological pH. The content of the carboxylic acid-type lipid is preferably 5 mol % or more, more preferably 10 mol % or more, still more preferably 30 mol % or more, yet more preferably 50 mol % or more, further preferably 60 mol % or more, and still further preferably 70 mol % or more, based on the total lipid amount included in the lipid particle or the lipid membrane. The upper limit of the content of the carboxylic acid-type lipid is 100 mol % based on the total lipid amount included in the lipid particle or the lipid membrane (in this example, all lipids included in the lipid particle or the lipid membrane are carboxylic acid-type lipids).

Whether a lipid other than the carboxylic acid-type lipid is included or not in the lipid particle and the lipid membrane, the content thereof can be appropriately determined from the viewpoint of solubility in an organic solvent, particle forming property and storage stability. For example, whether a carboxylic acid-type lipid other than the carboxylic acid-type lipid is included or not in the lipid particle and the lipid membrane, the content thereof and the like can be appropriately determined from the viewpoint of solubility in an organic solvent, particle forming property, membrane forming property and storage stability. However, the lipid particle forming property (e.g., ease of formation of a liposome, stability of the formed liposome and the like) and the lipid membrane forming property of the carboxylic acid-type lipid are superior to those of a known carboxylic acid-type lipid such as DHSG (1,5-dihexadecyl-N-succinyl-L-glutamate). When a liposome is formed using a known carboxylic acid-type lipid such as DHSG, the content to form a stable liposome has an upper limit. The number of carboxyl groups per molecule of the carboxylic acid-type lipid is the same or higher than that of a known carboxylic acid-type lipid such as DHSG, and the negative charge property at physiological pH of the carboxylic acid-type lipid is similar to or higher than that of a known carboxylic acid-type lipid such as DHSG. Considering these points, use of a carboxylic acid-type lipid other than our carboxylic acid-type lipid as a carboxylic acid-type lipid has less advantage. Therefore, in one example, our lipid particle and our lipid membrane do not include a carboxylic acid-type lipid other than our carboxylic acid-type lipid. When our lipid particle and our lipid membrane include a carboxylic acid-type lipid other than our carboxylic acid-type lipid, the content of the carboxylic acid-type lipid other than our carboxylic acid-type lipid is preferably 30 mol % or less, more preferably 10 mol % or less, still more preferably 7 mol % or less, and yet more preferably 5 mol % or less, based on the total lipid amount included in our lipid particle or our lipid membrane. The lower limit of the content of the carboxylic acid-type lipid other than our carboxylic acid-type lipid is not particularly limited, and a smaller lower limit is preferable and, for example, the lower limit is 1 mol % based on the total lipid amount included in our lipid particle or our lipid membrane. Examples of the carboxylic acid-type lipid other than our carboxylic acid-type lipid include a carboxylic acid-type lipid differing from our carboxylic acid-type lipid in that a moiety of M-NH— is substituted with a hydroxyl group and the like.

The carboxylic acid-type lipids (I) to (VI) will be described.

Carboxylic Acid-Type Lipid (I)

The carboxylic acid-type lipid (I) is represented by formula (I). When two or more same symbols (e.g., L, X and the like) exist in formula (I), the meanings of these same symbols may be the same or different as long as they are within the definition of the symbols.

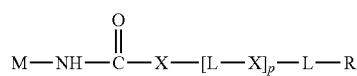
(I)

In formula (I), M represents an amino acid residue, an amino acid derivative residue, a peptide residue or a salt thereof that can be negatively charged at physiological pH.

The physiological pH is usually pH 5.5 to 9.0, preferably pH 6.5 to 8.0, and more preferably pH 7.0 to 7.8.

The fact that an amino acid residue, an amino acid derivative residue, a peptide residue or a salt thereof represented by M can be negatively charged at physiological pH means that an amino acid residue, an amino acid derivative residue, a peptide residue or a salt thereof represented by M can be negatively charged when coming into contact with blood.

An amino acid residue, an amino acid derivative residue, a peptide residue or a salt thereof represented by M may have, in addition to a functional group that can be negatively charged at physiological pH, a functional group that can be positively charged at physiological pH as long as it can be negatively charged at physiological pH as a whole. For example, when the number of functional groups (e.g., a carboxyl group or a salt thereof) that can be negatively charged at physiological pH is higher than the number of functional groups (e.g., an amino group) that can be positively charged at physiological pH, an amino acid residue, an amino acid derivative residue, a peptide residue or a salt thereof represented by M can be negatively charged at physiological pH as a whole.

Amino acid is an organic compound having a carboxyl group and an amino group in the same molecule. Amino acid is preferably aliphatic amino acid. Aliphatic amino acid may be any one of α-amino acid, β-amino acid, γ-amino acid, δ-amino acid and ε-amino acid, and is preferably α-amino acid. α-Amino acid may be any one of D-form and L-form, and is preferably L-form. Amino acid may be natural amino acid or non-natural amino acid, and is preferably natural amino acid. Natural amino acid is preferably any one of 20 types of amino acids included in a protein. Examples of the other amino acids include cystine, hydroxyproline, hydroxylysine, thyroxine, O-phosphoserine, desmosine, β-alanine, δ-aminovaleric acid, sarcosine (N-methylglycine), γ-aminobutyric acid (GABA), tricholomic acid, kainic acid, opine and the like.

Examples of the α-amino acid include glycine, alanine, valine, leucine, isoleucine, serine, threonine, tyrosine, cysteine, methionine, aspartic acid, asparagine, glutamic acid, glutamine, arginine, lysine, histidine, phenylalanine, tryptophan and the like, examples of the β-amino acid include β-alanine and the like, examples of the γ-amino acid include γ-amino-n-butyric acid (GABA), carnitine and the like, examples of the δ-amino acid include 5-aminolevulinic acid, 5-aminovaleric acid and the like, and examples of the ε-amino acid include δ-aminohexanoic acid and the like.

Examples of the non-natural amino acid include amino acid in which a main chain structure is different from that of natural amino acid (e.g., α,α-disubstituted amino acid (e.g., α-methylalanine or the like), N-alkyl-α-amino acid, D-amino acid, β-amino acid, α-hydroxy acid or the like), amino acid in which a side chain structure is different from that of natural amino acid (e.g., norleucine, homohistidine or the like), amino acid in which a side chain has excessive methylene (e.g., homoamino acid or the like) and amino acid in which a functional group (e.g., a thiol group) in a side chain is substituted with a sulfonic acid group (e.g., cysteic acid or the like). In addition, aminoalkanesulfonic acid having a sulfonic acid group and an amino group in the same molecule (e.g., aminoethanesulfonic acid (taurine) or the like) is included in the non-natural amino acid.

An amino acid residue represented by M means a moiety obtained by removing an amino group from amino acid unless otherwise specified. An amino group removed from α-amino acid, β-amino acid, γ-amino acid, δ-amino acid and ε-amino acid may be an amino group bonded to α-carbon, β-carbon, γ-carbon, δ-carbon and ε-carbon, respectively, or may be an amino group included in a side chain, and is preferably an amino group bonded to α-carbon, β-carbon, γ-carbon, δ-carbon and ε-carbon. When M represents an amino acid residue, —NH— of a structure represented by M-NH—CO— is derived from an amino group of amino acid. Thus, the amino acid residue represented by M is defined as a moiety obtained by removing an amino group from amino acid.

The amino acid residue or a salt thereof represented by M is not particularly limited as long as it can be negatively charged at physiological pH as a whole. The amino acid residue or a salt thereof represented by M is preferably an acidic amino acid residue, a neutral amino acid residue or a salt thereof, and more preferably an acidic amino acid residue or a salt thereof.

An acidic amino acid residue or a salt thereof has two carboxyl groups or salts thereof, and these carboxyl groups or salts thereof can be ionized at physiological pH and negatively charged. Therefore, the acidic amino acid residue or a salt thereof can be negatively charged at physiological pH as a whole. The acidic amino acid residue or a salt thereof is preferably an aspartic acid residue, a glutamic acid residue or a salt thereof.

A neutral amino acid residue or a salt thereof has one carboxyl group or a salt thereof, and this carboxyl group or salt thereof can be ionized at physiological pH and negatively charged. Meanwhile, a functional group included in a side chain of a neutral amino acid residue or a salt thereof is uncharged at physiological pH. Therefore, the neutral amino acid residue or a salt thereof can be negatively charged at physiological pH as a whole. Examples of the neutral amino acid residue include a glycine residue, an alanine residue, a phenylalanine residue, a leucine residue, an isoleucine residue, a methionine residue, a valine residue, an asparagine residue, a glutamine residue and the like. Examples of a preferable neutral amino acid residue include a glycine residue, an alanine residue and the like.

An amino acid derivative represented by M is produced by introducing a chemical modification into a side chain of amino acid, and has the same structure as that of amino acid except that a chemical modification is introduced into a side chain. An amino acid derivative residue represented by M means a moiety obtained by removing an amino group from an amino acid derivative unless otherwise specified. An amino group removed from a derivative of α-amino acid, β-amino acid, γ-amino acid, δ-amino acid and ε-amino acid may be an amino group bonded to α-carbon, β-carbon, γ-carbon, δ-carbon and ε-carbon, respectively, or may be an amino group included in a side chain, and is preferably an amino group bonded to α-carbon, β-carbon, γ-carbon, δ-carbon and ε-carbon, respectively. When M represents an amino acid derivative residue, —NH— of a structure represented by M-NH—CO— is derived from an amino group of an amino acid derivative. Thus, the amino acid derivative residue represented by M is defined as a moiety obtained by removing an amino group from an amino acid derivative.

The amino acid derivative residue represented by M is not particularly limited as long as it can be negatively charged at physiological pH as a whole. Examples of the amino acid derivative residue represented by M include a residue of a basic amino acid derivative. Examples of the introduced derivatization that a basic amino acid derivative comprises include amidation of an amino group of a side chain of a basic amino acid to a group represented by the formula: —NH—CO—$R_1$ wherein —NH— is derived from the amino group of the side chain of the basic amino acid, and $R_1$ represents a hydrocarbon group and the like. The basic amino acid has a carboxyl group bonded to α-carbon, an amino group bonded to α-carbon and an amino group included in a side chain bonded to α-carbon. As a result of derivatization of an amino group of a side chain into —NH—CO—$R_1$, the residue of a basic amino acid derivative can be negatively charged at physiological pH as a whole.

Examples of the basic amino acid include lysine, arginine, histidine and the like.

As a carboxylic acid used for amidation of an amino group of a side chain of a basic amino acid, for example, it is possible to use aliphatic carboxylic acid represented by the formula: $R_1$—COOH wherein $R_1$ is the same as defined above.

A hydrocarbon group represented by $R_1$ is preferably an aliphatic hydrocarbon group. The aliphatic hydrocarbon group may be linear or branched, and is preferably linear. The aliphatic hydrocarbon group may be saturated or unsaturated, and is preferably saturated. The number of carbon atoms of the aliphatic hydrocarbon group is usually 1 to 10, preferably 1 to 6, more preferably 1 to 4, and still more preferably 1 to 2. The unsaturated bond may be a carbon-carbon double bond or a carbon-carbon triple bond, and is preferably a carbon-carbon double bond.

Examples of the aliphatic hydrocarbon group represented by $R_1$ include an alkyl group, an alkenyl group, alkynyl group and the like, and it is preferably an alkyl group or an alkenyl group, and more preferably an alkyl group. Specific examples of the aliphatic hydrocarbon group represented by $R_1$ include a methyl group, an ethyl group, a propyl group, an isopropyl group, a butyl group, a sec-butyl group, a tert-butyl group, an isobutyl group, a pentyl group, a tert-pentyl group, an isopentyl group, a hexyl group, an isohexyl group, a heptyl group, an octyl group, a 2-ethylhexyl group, a nonyl group, a decyl group, an ethylene group, a propylene group, a butene group, an isobutene group, an isoprene group, a pentene group, a hexene group, a heptene group, an octene group, a nonene group, a decene group and the like. Specific preferable examples of the aliphatic hydrocarbon group represented by $R_1$ include a methyl group, an ethyl group and the like.

A peptide residue represented by M means a moiety obtained by removing an amino group from a peptide unless otherwise specified. An amino group removed from a peptide may be an amino group bonded to α-carbon, β-carbon, γ-carbon, δ-carbon or ε-carbon, or may be an amino group included in a side chain, and is preferably an amino group bonded to α-carbon, β-carbon, γ-carbon, S-carbon or ε-carbon. When M represents a peptide residue, —NH— of a structure represented by M-NH—CO— is derived from an amino group of a peptide. Thus, the peptide residue represented by M is defined as a moiety obtained by removing an amino group from a peptide.

The type and the number of amino acid residues constituting the peptide residue represented by M is not particularly limited as long as the peptide residue can be negatively charged at physiological pH as a whole. The amino acid residue as used herein is a usual meaning (a moiety obtained by removing H of an amino group and/or OH of a carboxyl group from amino acid), and differs from the abovementioned meaning (a moiety obtained by removing an amino group from amino acid).

The peptide residue represented by M can be composed of one or two or more amino acid residues selected from an acidic amino acid residue, a neutral amino acid residue and a basic amino acid residue, and is preferably composed of one or two or more amino acid residues selected from an acidic amino acid residue and a neutral amino acid residue, more preferably composed of one or two or more amino acid residues selected from an acidic amino acid residue, and still more preferably composed of one or two amino acid residues selected from aspartic acid and glutamic acid.

In the peptide residue represented by M, the difference between the number of functional groups (e.g., a carboxyl group or a salt thereof) that can be negatively charged at physiological pH and the number of functional groups (e.g., an amino group) that can be positively charged at physiological pH (the number of functional groups that can be negatively charged at physiological pH—the number of functional groups that can be positively charged at physiological pH) is preferably 1 or more, more preferably 2 or more, and still more preferably 3 or more. The upper limit of the difference is not particularly limited, and is preferably 10, more preferably 8, and still more preferably 4. In the peptide residue represented by M, the number of functional groups (e.g., an amino group) that can be positively charged at physiological pH is preferably 4 or less, more preferably 2 or less, and still more preferably 0.

The number of amino acid residues constituting the peptide residue represented by M is usually 2 to 12, preferably 2 to 7, more preferably 2 to 5, and still more preferably 2 to 4.

The peptide residue represented by M is preferably a peptide residue including one or two or more acidic amino acid residues, more preferably a peptide residue including two or more acidic amino acid residues, and still more preferably a peptide residue including two or more acidic amino acid residues selected from an aspartic acid residue and a glutamic acid residue. The peptide residue including one or two or more acidic amino acid residues may or may not include a neutral amino acid residue. The peptide residue including one or two or more acidic amino acid residues may or may not include a basic amino acid residue, and preferably does not include a basic amino acid residue. In other words, the peptide residue including one or two or more acidic amino acid residues is preferably composed of an acidic amino acid residue and a neutral amino acid residue, and more preferably composed of an acidic amino acid residue.

Examples of the peptide residue including two or more acidic amino acid residues selected from an aspartic acid residue and a glutamic acid residue include a peptide residue represented by formula (XII) (sometimes referred to as "AG residue"). The AG residue is a peptide residue composed of three acidic amino acid residues selected from an aspartic acid residue and a glutamic acid residue.

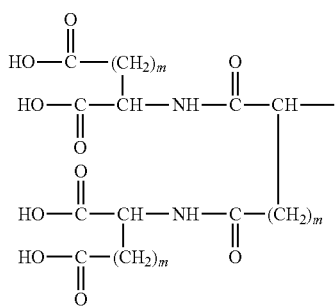

(XII)

In formula (XII), m represents 1 or 2. Integers represented by a plurality of m's existing in formula (XII) may be the same or different.

A salt of an amino acid residue, an amino acid derivative residue or a peptide residue represented by M is usually a salt formed by a carboxyl group, and specific examples thereof include a calcium salt, a magnesium salt, a potassium salt and the like.

In formula (I), R represents a hydrocarbon group. R is a monovalent functional group.

The number of carbon atoms of the hydrocarbon group represented by R is usually 8 to 30, preferably 10 to 24, more preferably 12 to 22, and still more preferably 14 to 18.

The hydrocarbon group represented by R is preferably an aliphatic hydrocarbon group. The aliphatic hydrocarbon group may be linear or branched, and is preferably linear. The aliphatic hydrocarbon group may be saturated or unsaturated, and is preferably saturated. The number of carbon atoms of the aliphatic hydrocarbon group is preferably 10 to 24, more preferably 12 to 22, and still more preferably 14 to 18. When the aliphatic hydrocarbon group has an unsaturated bond, the number of unsaturated bonds is usually 1 to 6, preferably 1 to 4, more preferably 1 to 3, and still more preferably 1 to 2. The unsaturated bond may be a carbon-carbon double bond or a carbon-carbon triple bond, and is preferably a carbon-carbon double bond.

Examples of the aliphatic hydrocarbon group represented by R include an alkyl group, an alkenyl group, alkynyl group and the like, and it is preferably an alkyl group or an alkenyl group, and more preferably an alkyl group. Specific examples of the aliphatic hydrocarbon group represented by R include a dodecyl group, a tridecyl group, a tetradecyl group, a pentadecyl group, a hexadecyl group, a heptadecyl group, an octadecyl group, a nonadecyl group, an icosyl group, a henicosyl group, a docosyl group, a dodecenyl group, a tricosyl group, a tridecenyl group, a tetradecenyl group, a pentadecenyl group, a hexadecenyl group, a heptadecenyl group, an octadecenyl group, a nonadecenyl group, an icocenyl group, a henicosenyl group, a docosenyl group, a tricosenyl group, a tridecadienyl group, a tetradecadienyl group, a pentadecadienyl group, a hexadecadienyl group, a heptadecadienyl group, an octadecadienyl group, a nonadecadienyl group, an icosadienyl group, a henicosadienyl group, a docosadienyl group, an octadecatrienyl group, an icosatrienyl group, an icosatetraenyl group, an icosapentaenyl group, a docosahexaenyl group, a methyldodecyl group, a methyltridecyl group, a methyltetradecyl group, a methylpentadecyl group, a methylheptadecyl group, a methyloctadecyl group, a methylnonadecyl group, a methylicosyl group, a methylhenicosyl group, a methyldocosyl group, an ethylundecyl group, an ethyldodecyl group, an ethyltridecyl group, an ethyltetradecyl group, an ethylpentadecyl group, an ethylheptadecyl group, an ethyloctadecyl group, an ethylnonadecyl group, an ethylicosyl group, an ethylhenicosyl group, a hexylheptyl group, a hexylnonyl group, a heptyloctyl group, a heptyldecyl group, an octylnonyl group, an octylundecyl group, a nonyldecyl group, a decylundecyl group, an undecyldodecyl group, a hexamethylundecyl group and the like. Examples of a preferable aliphatic hydrocarbon group include a tetradecyl group, a hexadecyl group, a heptadecyl group, an octadecyl group and the like.

In formula (I), L represents —CO—O—, —O—CO—, —CO—NH—, —NH—CO—, —CO—S—, —S—CO— or —S—S—. L represents preferably —CO—O—, —O—CO—, —CO—NH— or —NH—CO—. When a plurality of L's exist in formula (I) (when p is 1 or more), the meanings of these multiple L's may be the same or different as long as they are within the definition of L. L is a divalent functional group, and the right and left of L correspond to the right and left of formula (I). In other words, (*a1)-L-(*a2) is bonded to a group existing on the left side of L in formula (I) via a bond on the left side (*a1), and is bonded to a group existing on the right side of L in formula (I) via a bond on the right side (*a2). Therefore, —CO—O— is distinguished from —O—CO—, —CO—NH— is distinguished from —NH—CO—, and —CO—S— is distinguished from —S—CO—.

In formula (I), X represents a hydrocarbon group, a neutral amino acid residue or a polyalkylene glycol residue. When a plurality of X's exist in formula (I) (when p is 1 or more), the meanings of these multiple X's may be the same or different as long as they are within the definition of X. X is a divalent functional group.

The number of carbon atoms of the hydrocarbon group represented by X is usually 1 to 6, preferably 1 to 5, more preferably 1 to 4, and still more preferably 1 to 2.

The hydrocarbon group represented by X is preferably an aliphatic hydrocarbon group. The aliphatic hydrocarbon group may be linear or branched, and is preferably linear. The aliphatic hydrocarbon group may be saturated or unsaturated, and is preferably saturated. The unsaturated bond may be a carbon-carbon double bond or a carbon-carbon triple bond, and is preferably a carbon-carbon double bond. Examples of the aliphatic hydrocarbon group represented by X include an alkylene group, an alkenylene group, an alkynylene group and the like, and it is preferably an alkylene group or an alkenylene group, and more preferably an alkylene group. The number of carbon atoms of the alkylene group is usually 1 to 6, preferably 1 to 5, more preferably 1 to 4, and still more preferably 1 to 2. The number of carbon atoms of the alkenylene group is usually 2 to 6, preferably 2 to 5, more preferably 2 to 4, and still more preferably 2 to 3. The number of carbon atoms of the alkynylene group is usually 2 to 6, preferably 2 to 5, more preferably 2 to 4, and still more preferably 2 to 3.

Examples of the alkylene group include —$CH_2$—, —$(CH_2)_2$—, —$(CH_2)_3$—, —$CH(CH_3)CH_2$—, —$CH_2CH(CH_3)$—, —$(CH_2)_4$—, —$CH(CH_3)(CH_2)_2$—, —$(CH_2)_2CH(CH_3)$—, —$C(CH_3)_2CH_2$—, —$CH_2C(CH_3)_2$—, —$(CH_2)_5$—, —$CH(CH_3)(CH_2)_3$—, —$(CH_2)_3CH(CH_3)$—, —$CH(C_2H_5)(CH_2)_2$—, —$(CH_2)_2CH(C_2H_5)$—, —$CH_2CH(CH_3)(CH_2)_2$—, —$(CH_2)_2CH(CH_3)CH_2$—, —$CH_2CH(C_2H_5)CH_2$—, —$C(CH_3)_2(CH_2)_2$—, —$(CH_2)_2C(CH_3)_2$—, —$CH_2C(CH_3)_2CH_2$—, —$(CH_2)_6$—, —$CH(CH_3)(CH_2)_4$—, —$(CH_2)_4CH(CH_3)$—, —$CH(C_2H_5)(CH_2)_3$—, —$CH_2CH(CH_3)(CH_2)_3$—, —$(CH_2)_3CH(CH_3)CH_2$—, —$(CH_2)_2CH(CH_3)(CH_2)_2$—, —$(CH_2)_3CH(C_2H_5)$—, —$C(CH_3)_2(CH_2)_3$—, —$(CH_2)_3C(CH_3)_2$—, —$CH_2C(CH_3)_2(CH_2)_2$—, —$(CH_2)_2C(CH_3)_2CH_2$—, —$C(CH_3)_2C(CH_3)_2$— and the like. Examples of a preferable alkylene group include —$CH_2$—, —$(CH_2)_2$— and the like.

Examples of the alkenylene group include —CH=CH—, —CH=CH—$CH_2$—, —$CH_2$—CH=CH—, —CH=CH—$CH_2$—$CH_2$—, —$CH_2$—CH=CH—$CH_2$—, —$CH_2$—$CH_2$—CH=CH—, —CH=CH—CH=CH—, —$C(CH_3)$=CH—$CH_2$—, —CH=$C(CH_3)$—$CH_2$—, —CH=CH—$CH(CH_3)$—, —$CH(CH_3)$—CH=CH—, —$CH_2$—$C(CH_3)$=CH—, —$CH_2$—CH=$C(CH_3)$—, —CH=CH—$CH_2$—$CH_2$—$CH_2$—, —$CH_2$—CH=CH—$CH_2$—$CH_2$—, —$CH_2$—$CH_2$—CH=CH—$CH_2$—, —$CH_2$—$CH_2$—$CH_2$—CH=CH—, —CH=CH—$CH_2$—$CH_2$—$CH_2$—$CH_2$—, —$CH_2$—CH=CH—$CH_2$—$CH_2$—$CH_2$—, —$CH_2$—$CH_2$—CH=CH—$CH_2$—$CH_2$—, —$CH_2$—$CH_2$—$CH_2$—CH=CH—$CH_2$—$CH_2$—, —$CH_2$—$CH_2$—$CH_2$—$CH_2$—CH=CH—$CH_2$—, —$CH_2$—$CH_2$—$CH_2$—$CH_2$—$CH_2$—CH=CH— and the like. Examples of a preferable alkenylene group include —CH=CH—, —CH=CH—$CH_2$— and the like.

Examples of the alkynylene group include —C≡C—, —C≡C—$CH_2$—, —$CH_2$—C≡C—, —C≡C—$CH_2$—$CH_2$—, —$CH_2$—C≡C—$CH_2$—, —$CH_2$—$CH_2$—C≡C—, —C≡C—$CH_2$—$CH_2$—$CH_2$—, —$CH_2$—C≡C—$CH_2$—$CH_2$—, —$CH_2$—$CH_2$—C≡C—$CH_2$—, —$CH_2$—$CH_2$—$CH_2$—C≡C—, —$CH_2$—C≡C—$CH_2$—$CH_2$—$CH_2$—, —$CH_2$—$CH_2$—$CH_2$—C≡C—$CH_2$—, —$CH_2$—$CH_2$—$CH_2$—$CH_2$—C≡C— and the like. Examples of a preferable alkynylene group include —C≡C—, —C≡C—$CH_2$— and the like.

A neutral amino acid residue represented by X means a moiety obtained by removing a carboxyl group and an amino group from a neutral amino acid unless otherwise specified. The carboxyl group and the amino group of the neutral amino acid are used for formation of an adjacent moiety (—CO— or -L-) of X of formula (I). For example, when the carboxylic acid-type lipid (I) has a structure of —CO—X-L- (e.g., when p is 0), the carboxyl group of the neutral amino acid residue is used for formation of —CO— of a structure of —CO—X-L-, and the amino group of the neutral amino acid is used for formation of -L- of a structure of —CO—X-L-. When the carboxylic acid-type lipid (I) has a structure of -L-X-L- (e.g., when p is an integer of 1 or more), the carboxyl group of the neutral amino acid residue is used for formation of one -L- of a structure of -L-X-L-, and the amino group of the neutral amino acid is used for formation of the other -L- of a structure of -L-X-L-. Thus, the neutral amino acid residue represented by X is defined as a moiety obtained by removing a carboxyl group and an amino group from a neutral amino acid.

The neutral amino acid residue represented by X is preferably a neutral amino acid residue not having a reactive functional group (e.g., a hydroxyl group, a thiol group and the like) in a side chain. Examples of a preferable neutral amino acid residue include a glycine residue, an alanine residue, a phenylalanine residue, a leucine residue, an isoleucine residue, a valine residue, a methionine residue, an asparagine residue, a glutamine residue and the like, and examples of a more preferable neutral amino acid residue include a glycine residue, an alanine residue, an asparagine residue, a glutamine residue and the like. When the neutral amino acid residue represented by X is a neutral amino acid residue in which a side chain is a hydrocarbon group, overlapping occurs when X is a hydrocarbon group. In terms of excluding the overlapping when X is a hydrocarbon group, the neutral amino acid residue represented by X is preferably a neutral amino acid residue in which a side chain is not a hydrocarbon group. Examples of the neutral amino acid residue in which a side chain is not a hydrocarbon group include a methionine residue, an asparagine residue, a glutamine residue and the like.

A polyalkylene glycol residue represented by X means a moiety obtained by removing functional groups (e.g., a carboxyl group, an amino group, a hydroxyl group, a thiol group and the like) at both terminals from polyalkylene glycol or a polyalkylene glycol derivative unless otherwise specified. The polyalkylene glycol derivative is one in which one or both of hydroxyl groups at both terminals of polyalkylene glycol is/are substituted with another/other functional group(s) (e.g., a carboxyl group, an amino group, a thiol group and the like). The functional groups (e.g., a carboxyl group, an amino group, a hydroxyl group, a thiol group and the like) at both terminals of polyalkylene glycol or the polyalkylene glycol derivative are used for formation of an adjacent moiety (—CO— or -L-) of X of formula (I). For example, when the functional groups at both terminals of a polyalkylene glycol derivative are a carboxyl group and a hydroxyl group and the carboxylic acid-type lipid (I) has a structure of —CO—X-L- (e.g., when p is 0), the carboxyl group of the polyalkylene glycol derivative is used for formation of —CO— of a structure of —CO—X-L-, and the hydroxyl group of the polyalkylene glycol derivative is used for formation of -L- of a structure of —CO—X-L-. When the carboxylic acid-type lipid (I) has a structure of -L-X-L- (e.g., when p is an integer of 1 or more), a functional group at one terminal of polyalkylene glycol or the polyalkylene glycol derivative is used for formation of one -L- of a structure of -L-X-L-, and a functional group at the other terminal is used for formation of the other -L- of a structure of -L-X-L-. Thus, the polyalkylene glycol residue represented by X is defined as a moiety obtained by removing functional groups at both terminals from polyalkylene glycol or a polyalkylene glycol derivative.

Examples of an alkylene glycol unit constituting polyalkylene glycol include ethylene glycol, propylene glycol, butylene glycol and the like. The alkylene glycol unit constituting polyalkylene glycol may be one or two or more.

Examples of the polyalkylene glycol include polyethylene glycol, polypropylene glycol, polytrimethylene glycol, polybutylene glycol, polytetramethylene glycol, polyoxyethyleneoxypropylene glycol and the like. The molecular weight of the polyalkylene glycol is preferably 400 to 40,000, more preferably 1,000 to 10,000, and still more preferably 2,000 to 5,000.

In formula (I), p represents an integer of 0 or more. p is usually an integer of 0 to 4, preferably an integer of 0 to 3, more preferably an integer of 0 to 2, and still more preferably an integer of 0 to 1.

Carboxylic Acid-Type Lipid (II)

The carboxylic acid-type lipid (II) is represented by formula (II).

(II)

In formula (II), M and R are the same as defined above.

Carboxylic Acid-Type Lipid (III)

The carboxylic acid-type lipid (III) is represented by formula (III). The meanings of a plurality of same symbols (e.g., L's, X's, q's, Y's and the like) existing in formula (III) may be the same or different as long as they are within the definition of the symbols.

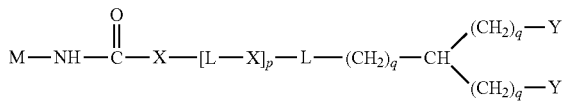
(III)

In formula (III), M, L, X and p are the same as defined above. The meaning of Y will be mentioned later. When a plurality of L's exist in formula (III), the meanings of these multiple L's may be the same or different as long as they are within the definition of L. When a plurality of X's exist in formula (III), the meanings of these multiple X's may be the same or different as long as they are within the definition of X.

In formula (III), q represents an integer of 0 or more. q is usually an integer of 0 to 8, preferably an integer of 0 to 6, more preferably an integer of 0 to 4, and still more preferably an integer of 0 to 2. Integers represented by a plurality of q's existing in formula (III) may be the same or different. The same applies to integers represented by a plurality of q's existing in other formulas.

Carboxylic Acid-Type Lipid (IV)

The carboxylic acid-type lipid (IV) is represented by formula (IV). The meanings of a plurality of same symbols (e.g., q's, Y's and the like) existing in formula (IV) may be the same or different as long as they are within the definition of the symbols.

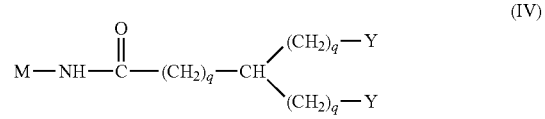
(IV)

In formula (IV), M and q are the same as defined above. The meaning of Y will be mentioned later. Integers represented by a plurality of q's existing in formula (IV) may be the same or different.

Carboxylic Acid-Type Lipid (V)

The carboxylic acid-type lipid (V) is represented by formula (V). The meanings of a plurality of same symbols (e.g., L's, X's, q's, Z's and the like) existing in formula (V) may be the same or different as long as they are within the definition of the symbols.

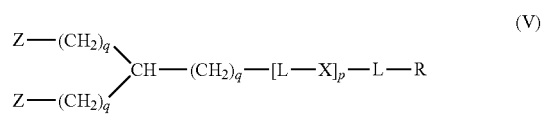
(V)

In formula (V), R, L, X, p and q are the same as defined above. The meaning of Z will be mentioned later. When a plurality of L's exist in formula (V), the meanings of these multiple L's may be the same or different as long as they are within the definition of L. When a plurality of X's exist in formula (V), the meanings of these multiple X's may be the same or different as long as they are within the definition of X. Integers represented by a plurality of q's existing in formula (V) may be the same or different.

Carboxylic Acid-Type Lipid (VI)

The carboxylic acid-type lipid (VI) is represented by formula (VI). The meanings of a plurality of same symbols (e.g., L's, X's, q's, Y's, Z's and the like) existing in formula (VI) may be the same or different as long as they are within the definition of the symbols.

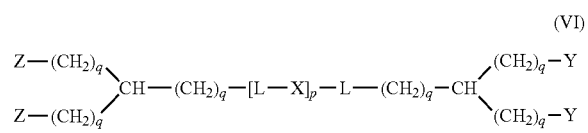
(VI)

In formula (VI), L, X, p and q are the same as defined above. The meanings of Y and Z will be mentioned later. When a plurality of L's exist in formula (VI), the meanings of these multiple L's may be the same or different as long as they are within the definition of L. When a plurality of X's exist in formula (VI), the meanings of these multiple X's may be the same or different as long as they are within the definition of X. Integers represented by a plurality of q's existing in formula (VI) may be the same or different.

Branched Moiety

In formulas (III), (IV), (V) and (VI), a branched moiety represented by formula (BP) is derived from, for example, a trifunctional compound (i.e., a residue of a trifunctional compound). A residue of a trifunctional compound means a moiety obtained by removing three reactive functional groups from a trifunctional compound unless otherwise specified. Three reactive functional groups of a trifunctional compound are used for formation of a moiety adjacent to the branched moiety (—CO— or -L-). Thus, the residue of a trifunctional compound is defined as a moiety obtained by removing three reactive functional groups from a trifunctional compound.

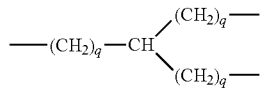  (BP)

The trifunctional compound has first, second and third functional groups independently selected from a carboxyl group, an amino group, a hydroxyl group and a thiol group. The first and second functional groups may be the same or different, and are preferably different. The third functional group may be the same as or different from one or both of the first and second functional groups, and is preferably different from one or both of the first and second functional groups. Examples of the trifunctional compound include trifunctional amino acid and the like. The trifunctional amino acid is amino acid having a first functional group that is a carboxyl group, a second functional group that is an amino group and a third functional group selected from a carboxyl group, an amino group, a hydroxyl group and a thiol group. The third functional group is preferably different from one or both of the first and second functional groups. Examples of the trifunctional amino acid include amino acid having a carboxyl group and an amino group bonded to α-carbon and having a carboxyl group, an amino group, a hydroxyl group or a thiol group in a side chain. Examples of such amino acid include aspartic acid, glutamic acid, lysine, serine and the like.

In one example, all of three q in the branched moiety are 0. In another example, of three q in the branched moiety, one q is an integer of 1 or more, for example, 1, 2, 3 or 4, and the other two q are 0. In further another example, of three q in the branched moiety, two q are the same or different and are an integer of 1 or more, for example, 1, 2, 3 or 4, and the other one q is 0. In still further another example, three q in the branched moiety are the same or different and are an integer of 1 or more, for example, 1, 2, 3 or 4.

When the branched moiety is derived from aspartic acid, of three q, one q is 1, and the other two q are 0.

When the branched moiety is derived from glutamic acid, of three q, one q is 2, and the other two q are 0.

When the branched moiety is derived from lysine, of three q, one q is 4, and the other two q are 0.

When the branched moiety is derived from serine, of three q, one q is 1, and the other two q are 0.

Meaning of Y

In formulas (III), (IV) and (VI), Y represents a branched chain composed of a branched chain body composed of one or more units Y1 and one or more groups Y2 bonded to the branched chain body, or represents a straight chain composed of one group Y2. The meanings of a plurality of Y's existing in each of formulas (III), (IV) and (VI) may be the same or different as long as they are within the definition of Y. When a plurality of same symbols (e.g., R's, L's, X's, p's, q's and the like) exist in a structure formula of each Y, the meanings of these same symbols may be the same or different as long as they are within the definition of the symbols.

Each unit Y1 is represented by formula (VII). When Y includes two or more units Y1, the meanings of these units Y1 may be the same or different as long as they are within the definition of Y1. When a plurality of same symbols (e.g., L's, X's, q's and the like) exist in a structure formula of each Y1, the meanings of these same symbols may be the same or different as long as they are within the definition of the symbols.

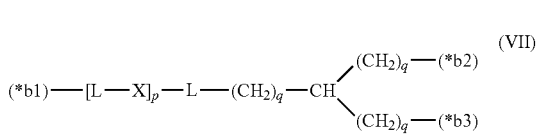  (VII)

In formula (VII), L, X, p and q are the same as defined above. When a plurality of L's exist in formula (VII), the meanings of these multiple L's may be the same or different as long as they are within the definition of L. When a plurality of X's exist in formula (VII), the meanings of these multiple X's may be the same or different as long as they are within the definition of X. Integers represented by a plurality of q's existing in formula (VII) may be the same or different.

In formula (VII), (*b1), (*b2) and (*b3) represent a bond of each unit Y1.

Each group Y2 is represented by formula (VIII). When Y includes two or more groups Y2, the meanings of these groups Y2 may be the same or different as long as they are within the definition of Y2. When a plurality of same symbols (e.g., L's, X's and the like) exist in a structure formula of each Y2, the meanings of these same symbols may be the same or different as long as they are within the definition of the symbols.

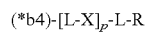  (VIII)

In formula (VIII), R, L, X and p are the same as defined above. When a plurality of L's exist in formula (VIII), the meanings of these multiple L's may be the same or different as long as they are within the definition of L. When a plurality of X's exist in formula (VIII), the meanings of these multiple X's may be the same or different as long as they are within the definition of X. When the carboxylic acid-type lipid has a plurality of groups Y2, the meanings of R's included in the plurality of groups Y2 (R's in formula (VIII)) may be the same or different as long as they are within the definition of R.

In formula (VIII), (*b4) represents a bond of each group Y2.

In one example, Y represents a branched chain composed of a branched chain body composed of one or more units Y1 and one or more groups Y2 bonded to the branched chain body.

When the branched chain body is composed of one unit Y1, a bond (*b1) of the unit Y1 is bonded to $(CH_2)_q$ in formula (III), (IV) or (VI). When the branched chain body is composed of one unit Y1, two groups Y2 are bonded to the branched chain body. A bond (*b4) of each group Y2 is bonded to a bond (*b2) or (*b3) of a unit Y1 constituting the branched chain body, and each group Y2 constitutes a terminal part of Y.

When the branched chain body is composed of two or more units Y1, a bond (*b1) of each unit Y1 is bonded to $(CH_2)_q$ in formula (III), (IV) or (VI), or is bonded to a bond (*b2) or (*b3) of another unit Y1 constituting the branched chain body. In other words, when the branched chain body is composed of two or more units Y1, the branched chain body includes, in addition to one unit Y1 bonded to $(CH_2)_q$ in formula (III), (IV) or (VI), one or more units Y1 in which a bond (*b1) is bonded to a bond (*b2) or (*b3) of another unit Y1. When the branched chain body is composed of two or more units Y1, (the number of units Y1+1) groups Y2 are bonded to the branched chain body. A bond (*b4) of each group Y2 is bonded to a bond (*b2) or (*b3) of any unit Y1 constituting the branched chain body, and each group Y2 constitutes a terminal part of Y.

In the example in which Y represents a branched chain composed of a branched chain body composed of one or more units Y1 and one or more groups Y2 bonded to the branched chain body, the number of units Y1 included in Y is not particularly limited as long as it is 1 or more. The number of units Y1 included in Y is usually 1 to 4, preferably 1 to 3, more preferably 1 to 2, and still more preferably 1. The number of groups Y2 included in Y is determined according to the number of units Y1 included in Y. When the number of units Y1 is 1 or more, the number of groups Y2 bonded to the branched chain body is (the number of units Y1+1).

In another example, Y represents a straight chain composed of one group Y2. In this example, a bond (*b4) of the group Y2 is bonded to $(CH_2)_q$ in formula (III), (IV) or (VI).

In the example in which Y represents a straight chain composed of a group Y2, Y does not include a unit Y1 (the number of units Y1 is 0), and the number of groups Y2 included in Y is 1.

Each Y can be selected from, for example, straight and branched chains represented by formulas (XIII), (XIV), (XV) and (XVI).

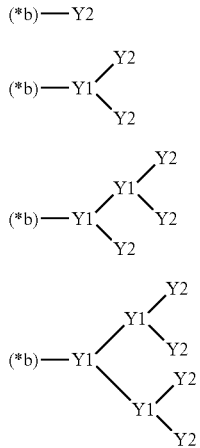

(XIII)
(XIV)
(XV)
(XVI)

In formulas (XIII) to (XVI), Y1 represents one unit Y1, Y2 represents one group Y2, and (*b) represents a bond of the unit Y1 bonded to $(CH_2)_q$ in formula (III), (IV) or (VI).

Meaning of Z

In formulas (V) and (VI), Z represents a branched chain composed of a branched chain body composed of one or more units Z1 and one or more groups Z2 bonded to the branched chain body, or represents a straight chain composed of one group Z2. The meanings of a plurality of Z's existing in each of formulas (V) and (VI) may be the same or different as long as they are within the definition of Z. When a plurality of same symbols (e.g., M's, L's, X's, p's, q's and the like) exist in a structure formula of each Z, the meanings of these same symbols may be the same or different as long as they are within the definition of the symbols.

Each unit Z1 is represented by formula (IX). When Z includes two or more units Z1, the meanings of these units Z1 may be the same or different as long as they are within the definition of Z1. When a plurality of same symbols (e.g., L's, X's, q's and the like) exist in a structure formula of each Z1, the meanings of these same symbols may be the same or different as long as they are within the definition of the symbols.

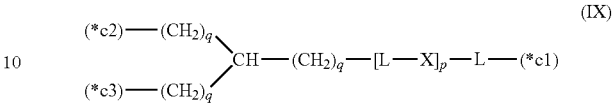

(IX)

In formula (IX), L, X, p and q are the same as defined above. When a plurality of L's exist in formula (IX), the meanings of these multiple L's may be the same or different as long as they are within the definition of L. When a plurality of X's exist in formula (IX), the meanings of these multiple X's may be the same or different as long as they are within the definition of X. Integers represented by a plurality of q's existing in formula (IX) may be the same or different.

In formula (IX), (*c1), (*c2) and (*c3) represent a bond of each unit Z1.

Each group Z2 is selected from groups represented by formulas (X) and (XI).

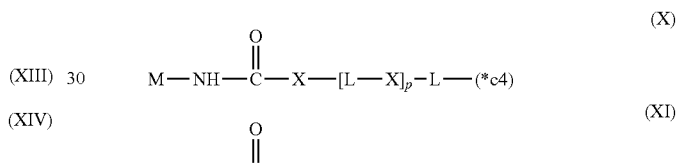

(X)
(XI)

In formula (X), M, L, X and p are the same as defined above, and (*c4) represents a bond of each group Z2. In formula (XI), M is the same as defined above, and (*c5) represents a bond of each group Z2. When a plurality of L's exist in formula (X), the meanings of these multiple L's may be the same or different as long as they are within the definition of L. When a plurality of X's exist in formula (X), the meanings of these multiple X's may be the same or different as long as they are within the definition of X. When the carboxylic acid-type lipid has a plurality of groups Z2, the meanings of R's included in the plurality of groups Z2 (R's in formula (X) or (XI)) may be the same or different as long as they are within the definition of R.

In one example, Z represents a branched chain composed of a branched chain body composed of one or more units Z1 and one or more groups Z2 bonded to the branched chain body.

When the branched chain body is composed of one unit Z1, a bond (*c1) of the unit Z1 is bonded to $(CH_2)_q$ in formula (V) or (VI). When the branched chain body is composed of one unit Z1, two groups Z2 are bonded to the branched chain body. A bond (*c4) or (*c5) of each group Z2 is bonded to a bond (*c2) or (*c3) of a unit Z1 constituting the branched chain body, and each group Z2 constitutes a terminal part of Z.

When the branched chain body is composed of two or more units Z1, a bond (*c1) of each unit Z1 is bonded to $(CH_2)_q$ in formula (V) or (VI), or is bonded to a bond (*c2) or (*c3) of another unit Z1 constituting the branched chain body. In other words, when the branched chain body is composed of two or more units Z1, the branched chain body includes, in addition to one unit Z1 bonded to $(CH_2)_q$ in formula (V) or (VI), one or more units Z1 in which a bond (*c1) is bonded to a bond (*c2) or (*c3) of another unit Z1. When the branched chain body is composed of two or more units Z1, (the number of units Z1+1) groups Z2 are bonded to the branched chain body. A bond (*c4) or (*c5) of each group Z2 is bonded to a bond (*c2) or (*c3) of any unit Z1 constituting the branched chain body, and each group Z2 constitutes a terminal part of Z.

In the example in which Z represents a branched chain composed of a branched chain body composed of one or more units Z1 and one or more groups Z2 bonded to the branched chain body, the number of units Z1 included in Z is not particularly limited as long as it is 1 or more. The number of units Z1 included in Z is usually 1 to 4, preferably 1 to 3, more preferably 1 to 2, and still more preferably 1. The number of groups Z2 included in Z is determined according to the number of units Z1 included in Z. When the number of units Z1 is 1 or more, the number of groups Z2 bonded to the branched chain body is (the number of units Z1+1).

In another example, Z represents a straight chain composed of one group Z2. In this example, a bond (*c4) or (*c5) of the group Z2 is bonded to $(CH_2)_q$ in formula (V) or (VI).

In the example in which Z represents a straight chain composed of a group Z2, Z does not include a unit Z1 (the number of units Z1 is 0), and the number of groups Z2 included in Z is 1.

Each Z can be selected from, for example, straight and branched chains represented by formulas (XVII), (XVIII), (XIX) and (XX).

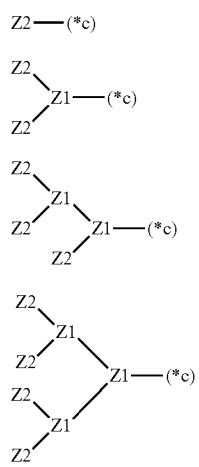

In formulas (XVII) to (XX), Z1 represents one unit Z1, Z2 represents one group Z2, and (*c) represents a bond of the unit Z1 bonded to $(CH_2)_q$ in formula (V) or (VI).

Method of Producing Carboxylic Acid-Type Lipid (I)

One example of a method of producing the carboxylic acid-type lipid (I) will be described. When a plurality of same symbols (e.g., L's, X's and the like) exist in a structure formula of one certain compound, the meanings of these same symbols may be the same or different as long as they are within the definition of the symbols. When the same symbols (e.g., L, X and the like) exist in structure formulas of two or more compounds, the meanings of these same symbols may be the same or different as long as they are within the definition of the symbols.

Step 1A

A compound (1) represented by formula (1):

$$M\text{-}NH_2 \qquad (1)$$

wherein M is the same as defined above, is provided.

The compound (1) can be produced in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. The compound (1) may be a commercially available product.

Step 2A

A compound (2) represented by formula (2):

$$HOOC\text{---}X\text{-}A_1 \qquad (2)$$

wherein X is the same as defined above, and $A_1$ represents a carboxyl group, an amino group, a hydroxyl group or a thiol group, is provided.

The compound (2) can be produced in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. The compound (2) may be a commercially available product.

When X is a hydrocarbon group, $A_1$ is selected from a carboxyl group, an amino group, a hydroxyl group and a thiol group.

When X is a hydrocarbon group and $A_1$ is a carboxyl group, examples of the compound (2) include aliphatic dicarboxylic acid and the like. Examples of the aliphatic dicarboxylic acid include malonic acid, succinic acid, glutaric acid, 2-methylglutaric acid, 3-methylglutaric acid, adipic acid, pimelic acid, suberic acid, azelaic acid, sebacic acid, dodecanedioic acid, maleic acid, fumaric acid, citraconic acid, mesaconic acid, 2-pentenedioic acid, itaconic acid, allylmalonic acid, isopropylidenesuccinic acid, 2,2,4-trimethyladipic acid, 2,4,4-trimethyladipic acid, 2,4-hexadienedioic acid, acetylenedicarboxylic acid and the like. The aliphatic dicarboxylic acid may be acid anhydride.

When X is a hydrocarbon group and $A_1$ is an amino group, examples of the compound (2) include neutral amino acid in which a side chain is a hydrocarbon group and the like. Examples of the neutral amino acid in which a side chain is a hydrocarbon group include glycine, alanine, phenylalanine, leucine, isoleucine, valine and the like.

When X is a hydrocarbon group and $A_1$ is a hydroxyl group, examples of the compound (2) include aliphatic hydroxycarboxylic acid and the like. Examples of the aliphatic hydroxycarboxylic acid include glycolic acid, lactic acid, hydroxybutyric acid, hydroxyvaleric acid, hydroxycaproic acid, hydroxycapric acid and the like.

When X is a hydrocarbon group and $A_1$ is a thiol group, examples of the compound (2) include aliphatic carboxylic acid thiol and the like. Examples of the aliphatic carboxylic acid thiol include 2-mercaptopropionic acid, 3-mercaptopropionic acid, 3-mercaptobutanoic acid, 2-mercaptoisobutyric acid, 3-mercaptoisobutyric acid, 3-mercapto-3-methylbutyric acid, 2-mercaptovaleric acid, 3-mercaptoisovaleric acid, 4-mercaptovaleric acid, 3-phenyl-3mercaptopropionic acid and the like.

When X is a neutral amino acid residue, $A_1$ is an amino group, and the compound (2) is neutral amino acid. Examples of the neutral amino acid include a glycine residue, an alanine residue, a phenylalanine residue, a leucine residue, an isoleucine residue, a valine residue, a methionine residue, an asparagine residue, a glutamine residue and the like. In terms of excluding the overlapping when X is a hydrocarbon group, the neutral amino acid is preferably neutral amino acid in which a side chain is not a hydrocarbon group. Examples of the neutral amino acid in which a side chain is not a hydrocarbon group include methionine, asparagine, glutamine and the like.

When X is a polyalkylene glycol residue, $A_1$ is a carboxyl group, an amino group, a hydroxyl group or a thiol group, and the compound (2) is a polyalkylene glycol derivative having a carboxyl group at one terminal and having a carboxyl group, a hydroxyl group, an amino group or a thiol group at the other terminal. Polyalkylene glycol derivatives in which various functional groups are introduced into one or both terminals are commercially available.

Step 3A

A compound (3) represented by formula (3):

$$D_1\text{-}X\text{-}[L\text{-}X]_{p-1}\text{-}E_p \qquad (3)$$

wherein L and X are the same as defined above, and p represents an integer of 1 or more, and $D_1$ and $E_p$ each independently represent a carboxyl group, an amino group, a hydroxyl group or a thiol group, is provided, as necessary.

A functional group $D_1$ is a functional group that can be reacted with the functional group $A_1$ of the compound (2), and is selected from a carboxyl group, an amino group, a hydroxyl group and a thiol group. When $A_1$ is a carboxyl group, $D_1$ is an amino group, a hydroxyl group or a thiol group. When $A_1$ is an amino group, $D_1$ is a carboxyl group. When $A_1$ is a hydroxyl group, $D_1$ is a carboxyl group. When $A_1$ is a thiol group, $D_1$ is a carboxyl group or a thiol group.

The compound (3) can be produced in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. The compound (3) may be a commercially available product.

One example of a method of producing the compound (3) will be described.

According to an integer represented by p, a compound (3-1) represented by the formula: $D_1\text{-}X\text{-}E_1$, a compound (3-2) represented by the formula: $D_2\text{-}X\text{-}E_2$, a compound (3-3) represented by the formula: $D_3\text{-}X\text{-}E_3$, . . . , a compound (3-p) represented by the formula: $D_p\text{-}X\text{-}E_p$ are provided. For example, when p is 1, the compound (3-1) is provided, when p is 2, the compound (3-1) and the compound (3-2) are provided, and when p is 3, the compound (3-1), the compound (3-2) and the compound (3-3) are provided.

A functional group $D_1$ and a functional group $E_p$ are the same as defined above.

Functional groups $E_1$ to $E_{p-1}$ are each independently selected from a carboxyl group, an amino group, a hydroxyl group and a thiol group.

Functional groups $D_2$ to $D_p$ each are functional groups that can be reacted with the functional groups $E_1$ to $E_{p-1}$, and are each independently selected from a carboxyl group, an amino group, a hydroxyl group and a thiol group. For example, the functional group $D_2$ is a functional group that can be reacted with the functional group $E_1$, the functional group $D_3$ is a functional group that can be reacted with the functional group $E_2$, and the functional group $D_p$ is a functional group that can be reacted with the functional group $E_{p-1}$. Specific examples of a combination of functional groups that can be reacted are the same as the specific examples of the combination of the functional group $A_1$ and the functional group $D_1$.

The compounds (3-1) to (3-p) are generalized by a compound (3-k) represented by the formula: $D_k\text{-}X\text{-}E_k$ (k=1, 2, . . . , p), and the compound (3-k) will be described.

When X is a hydrocarbon group, $D_k$ and $E_k$ are each independently selected from a carboxyl group, an amino group, a hydroxyl group and a thiol group.

When X is a hydrocarbon group, $D_k$ is a carboxyl group, and $E_k$ is a carboxyl group, examples of the compound (3-k) include aliphatic dicarboxylic acid and the like. Specific examples of the aliphatic dicarboxylic acid are the same as mentioned above. The aliphatic dicarboxylic acid may be acid anhydride.

When X is a hydrocarbon group, $D_k$ is a carboxyl group, and $E_k$ is an amino group, examples of the compound (3-k) include neutral amino acid in which a side chain is a hydrocarbon group and the like. Specific examples of the neutral amino acid in which a side chain is a hydrocarbon group are the same as mentioned above.

When X is a hydrocarbon group, $D_k$ is a carboxyl group, and $E_k$ is a hydroxyl group, examples of the compound (3-k) include aliphatic hydroxycarboxylic acid and the like. Specific examples of the aliphatic hydroxycarboxylic acid are the same as mentioned above.

When X is a hydrocarbon group, $D_k$ is a carboxyl group, and $E_k$ is a thiol group, examples of the compound (3-k) include aliphatic carboxylic acid thiol and the like. Specific examples of the aliphatic carboxylic acid thiol are the same as mentioned above.

When X is a hydrocarbon group, $D_k$ is an amino group, and $E_k$ is a carboxyl group, examples of the compound (3-k) include neutral amino acid in which a side chain is a hydrocarbon group and the like. Specific examples of the neutral amino acid in which a side chain is a hydrocarbon group are the same as mentioned above.

When X is a hydrocarbon group, $D_k$ is an amino group, and $E_k$ is an amino group, examples of the compound (3-k) include aliphatic diamine and the like. Examples of the aliphatic diamine include 1,4-butanediamine, 1,5-pentanediamine, 1,2-ethanediamine, 1,3-propanediamine, 1,6-hexanediamine and the like.

When X is a hydrocarbon group, $D_k$ is an amino group, and $E_k$ is a hydroxyl group, examples of the compound (3-k) include aliphatic hydroxy amine and the like. Examples of the aliphatic hydroxy amine include monoethanolamine, diethanolamine, triethanolamine, monopropanolamine, dipropanolamine, tripropanolamine, monobutanolamine, dibutanolamine, tributanolamine, N-methyl-diethanolamine, N,N-dimethylmonoethanolamine, aminomethyl propanol and the like.

When X is a hydrocarbon group, $D_k$ is an amino group, and $E_k$ is a thiol group, examples of the compound (3-k) include aliphatic amine having a thiol group and the like. Examples of the aliphatic amine having a thiol group include cysteamine, N-alkylcysteamine, 3-aminopropanethiol, 4-aminobutanethiol and the like.

When X is a hydrocarbon group, $D_k$ is a hydroxyl group, and $E_k$ is a carboxyl group, examples of the compound (3-k) include aliphatic hydroxycarboxylic acid and the like. Specific examples of the aliphatic hydroxycarboxylic acid are the same as mentioned above.

When X is a hydrocarbon group, $D_k$ is a hydroxyl group, and $E_k$ is an amino group, examples of the compound (3-k) include aliphatic hydroxy amine and the like. Specific examples of the aliphatic hydroxy amine are the same as mentioned above.

When X is a hydrocarbon group, $D_k$ is a hydroxyl group, and $E_k$ is a hydroxyl group, examples of the compound (3-k) include aliphatic diol and the like. Examples of the aliphatic diol include ethylene glycol, 1,3-propylene glycol, 1,2-propylene glycol, 1,2-butylene glycol, 1,4-butylene glycol, isopentanediol, 1,2-pentanediol, 1,3-pentanediol, 1,4-pentanediol, 1,5-pentanediol, 1,2-hexanediol, 1,3-hexanediol, 1,4-hexanediol, 1,5-hexanediol, 1,6-hexanediol, 3-methyl-1,5-pentanediol, 2-methyl-2,4-pentanediol, 1,2-heptanediol, 1,3-heptanediol, 1,4-heptanediol, 1,5-heptanediol, 1,6-heptanediol, 1,7-heptanediol, 2,4-heptanediol, 3,4-heptanediol, 1,2-octanediol, 2,3-octanediol, 2-ethyl-1,3-hexanediol, 2-butyl-2-ethyl-1,3-propanediol, 2,5-dimethyl-2,5-hexanediol and the like.

When X is a hydrocarbon group, $D_k$ is a hydroxyl group, and $E_k$ is a thiol group, examples of the compound (3-k) include aliphatic alcohol having a thiol group and the like. Examples of the aliphatic alcohol having a thiol group include 2-mercaptoethanol, 3-mercapto-1-propanol, 3-mercapto-2-propanol, 4-mercapto-1-butanol, 4-mercapto-2-butanol, 4-mercapto-3-butanol, 1-mercapto-1,1-methanediol, 1-mercapto-1,1-ethanediol, 3-mercapto-1,2-propanediol (α-thioglycerol), 2-mercapto-1,2-propanediol, 2-mercapto-2-methyl-1,3-propanediol, 2-mercapto-2-ethyl-1,3-propanediol, 1-mercapto-2,2-propanediol, 2-mercaptoethyl-2-methyl-1,3-propanediol, 2-mercaptoethyl-2-ethyl-1,3-propanediol and the like.

When X is a hydrocarbon group, $D_k$ is a thiol group, and $E_k$ is a carboxyl group, examples of the compound (3-k) include aliphatic carboxylic acid thiol and the like. Specific examples of the aliphatic carboxylic acid thiol are the same as mentioned above.

When X is a hydrocarbon group, $D_k$ is a thiol group, and $E_k$ is an amino group, examples of the compound (3-k) include aliphatic amine having a thiol group and the like. Specific examples of the aliphatic amine having a thiol group are the same as mentioned above.

When X is a hydrocarbon group, $D_k$ is a thiol group, and $E_k$ is a hydroxyl group, examples of the compound (3-k) include aliphatic alcohol having a thiol group and the like. Specific examples of the aliphatic alcohol having a thiol group are the same as mentioned above.

When X is a hydrocarbon group, $D_k$ is a thiol group, and $E_k$ is a thiol group, examples of the compound (3-k) include aliphatic dithiol and the like. Examples of the aliphatic dithiol include 1,4-butanedithiol, ethanedithiol and the like.

When X is a neutral amino acid residue, one of $D_k$ and $E_k$ is a carboxyl group, the other is an amino group, and the compound (3-k) is a neutral amino acid. Examples of the neutral amino acid include a glycine residue, an alanine residue, a phenylalanine residue, a leucine residue, an isoleucine residue, a valine residue, a methionine residue, an asparagine residue, a glutamine residue and the like. In terms of excluding the overlapping when X is a hydrocarbon group, the neutral amino acid is preferably neutral amino acid in which a side chain is not a hydrocarbon group. Examples of the neutral amino acid in which a side chain is not a hydrocarbon group include methionine, asparagine, glutamine and the like.

When X is a polyalkylene glycol residue, $D_k$ and $E_k$ are each independently selected from a carboxyl group, an amino group, a hydroxyl group and a thiol group, and the compound (3-k) is polyalkylene glycol having hydroxyl groups at both terminals, a polyalkylene glycol derivative having a hydroxyl group at one terminal and having a carboxyl group, an amino group or a thiol group at the other terminal, or a polyalkylene glycol derivative having a carboxyl group, an amino group or a thiol group each independently at both terminals. Polyalkylene glycol derivatives in which various functional groups are introduced into one or both terminals are commercially available.

The functional group $E_1$ of the compound (3-1) is reacted with the functional group $D_2$ of the compound (3-2) in accordance with a conventional method to produce a compound represented by the formula: $D_1$-X-L-X-$E_2$, and then the functional group $E_2$ of the produced compound is reacted with the functional group $D_3$ of the compound (3-3) in accordance with a conventional method to produce a compound represented by the formula: $D_1$-X-L-X-L-X-$E_3$. The same step is repeated to produce a compound represented by the formula: $D_1$-X-$[L-X]_{p-2}$-$E_{p-1}$, and the functional group $E_{p-1}$ of the produced compound is reacted with the functional group $D_p$ of the compound (3-p) in accordance with a conventional method to produce a compound (3) represented by the formula: $D_1$-X-$[L-X]_{p-1}$-$E_p$. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method.

When $E_1$ is a carboxyl group and $D_2$ is an amino group, L formed by the reaction of both groups is —CO—NH—. When $E_1$ is a carboxyl group and $D_2$ is a hydroxyl group, L formed by the reaction of both groups is —CO—O—. When $E_1$ is a carboxyl group and $D_2$ is a thiol group, L formed by the reaction of both groups is —CO—S—. When $E_1$ is an amino group and $D_2$ is a carboxyl group, L formed by the reaction of both groups is —NH—CO—. When $E_1$ is a hydroxyl group and $D_2$ is a carboxyl group, L formed by the reaction of both groups is —O—CO—. When $E_1$ is a thiol group and $D_2$ is a carboxyl group, L formed by the reaction of both groups is —S—CO—. When $E_1$ is a thiol group and $D_2$ is a thiol group, L formed by the reaction of both groups is —S—S—. Specific examples of L formed by the reaction of other two functional groups are the same as the specific examples of L formed by the reaction of the functional group $E_1$ and the functional group $D_2$.

Step 4A

A compound (4) represented by formula (4):

$$A_2\text{-R} \qquad (4)$$

wherein R is the same as defined above, and $A_2$ represents a carboxyl group, an amino group, a hydroxyl group or a thiol group, is provided.

A functional group $A_2$ is a functional group that can be reacted with the functional group $A_1$ of the compound (2) or the functional group $E_p$ of the compound (3), and is selected from a carboxyl group, an amino group, a hydroxyl group and a thiol group. Specific examples of a combination of functional groups that can be reacted are the same as the specific examples of the combination of the functional group $A_1$ and the functional group $D_1$.

The compound (4) can be produced in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. The compound (4) may be a commercially available product.

When $A_2$ is a carboxyl group, examples of the compound (4) include linear or branched saturated or unsaturated aliphatic carboxylic acid and the like. Examples of the aliphatic carboxylic acid include acetic acid, propionic acid, butyric acid, valeric acid, isovaleric acid, caproic acid, enanthic acid, caprylic acid, undecanoic acid, lauric acid, tridecanoic acid, myristic acid, pentadecanoic acid, palmitic acid, heptadecanoic acid, stearic acid, nonadecanoic acid, arachic acid, behenic acid, palmitoleic acid, oleic acid, linoleic acid, linoleic acid, arachidonic acid and the like.

When $A_2$ is an amino group, examples of the compound (4) include linear or branched saturated or unsaturated aliphatic amine and the like. The aliphatic amine may be any one of primary aliphatic amine and secondary aliphatic amine, and is preferably primary aliphatic amine. Examples of the aliphatic amine include dodecylamine, tridecylamine, tetradecylamine, pentadecylamine, hexadecylamine, heptadecylamine, octadecylamine, docosylamine, oleylamine, N-methyl-dodecylamine, N-methyl-tetradecylamine, N-methyl-hexadecylamine, N-ethyl-dodecylamine, N-ethyl-tetradecylamine, N-ethyl-hexadecylamine, N-propyl-dodecylamine, N-propyl-tetradecylamine, N-propyl-hexadecylamine, dioleylamine and the like.

When $A_2$ is a hydroxyl group, examples of the compound (4) include linear or branched saturated or unsaturated aliphatic alcohol and the like. The aliphatic alcohol may be any one of primary aliphatic alcohol, secondary aliphatic alcohol and tertiary aliphatic alcohol, and is preferably primary aliphatic alcohol. Examples of the aliphatic alcohol include lauryl alcohol, cetyl alcohol, stearyl alcohol, behenyl alcohol, 1,1-dodecenol, 1-oley alcohol, linolenyl alcohol and the like. The compound (4) may be dialkyl glycerol in which aliphatic alcohol is ether bonded to position 1 and position 3 or position 1 and position 2 of glycerin.

When $A_2$ is a thiol group, examples of the compound (4) include linear or branched saturated or unsaturated aliphatic thiol and the like. Examples of the aliphatic thiol include methanethiol, ethanethiol, propanethiol, butanethiol, pentanethiol, hexanethiol, heptanethiol, octanethiol, nonanethiol, decanethiol, undecanethiol, hexadecanethiol, octadecanethiol and the like.

Step 5A

When p in formula (I) is 0, a carboxylic acid-type lipid (I) is produced: by reacting the functional group $A_1$ of the compound (2) with the functional group $A_2$ of the compound (4) in accordance with a conventional method to produce a compound represented by the formula: HOOC—X-L-R, and then reacting the carboxyl group of the produced compound with the amino group of the compound (1); or by reacting the amino group of the compound (1) with the carboxyl group of the compound (2) in accordance with a conventional method to produce a compound represented by the formula: M-NH—CO—X-$A_1$, and then reacting the functional group $A_1$ of the produced compound with the functional group $A_2$ of the compound (4) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (I) is 1 or more, a compound represented by the formula: HOOC—X-[L-X]$_p$-L-R is produced: by reacting the functional group $E_p$ of the compound (3) with the functional group $A_2$ of the compound (4) in accordance with a conventional method to produce a compound represented by the formula: $D_1$-X-[L-X]$_{p-1}$-L-R, and then reacting the functional group $D_1$ of the produced compound with the functional group $A_1$ of the compound (2) in accordance with a conventional method; or by reacting the functional group $A_1$ of the compound (2) with the functional group $D_1$ of the compound (3) in accordance with a conventional method to produce a compound represented by the formula: HOOC—X-[L-X]$_p$-$E_p$, and then reacting the functional group $E_p$ of the produced compound with the functional group $A_2$ of the compound (4) in accordance with a conventional method. Then, a carboxylic acid-type lipid (I) is produced by reacting the carboxyl group of the compound represented by the formula: HOOC—X-[L-X]$_p$-L-R with the amino group of the compound (1). In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

As mentioned above, the carboxylic acid-type lipid (I) can be produced by a method including step 1A to step 5A. In each step, the order of reaction can be appropriately changed as long as a desired compound can be produced.

Method of Producing Carboxylic Acid-Type Lipid (II)

One example of a method of producing the carboxylic acid-type lipid (II) will be described.

Step 1B

A compound (1) is provided.

Step 2B

A compound (4) in which $A_2$ is a carboxyl group is provided.

Step 3B

A carboxylic acid-type lipid (II) is produced by reacting the amino group of the compound (1) with the carboxyl group of the compound (4) in which $A_2$ is a carboxyl group in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method.

As mentioned above, the carboxylic acid-type lipid (II) can be produced by a method including step 1B to step 3B. In each step, the order of reaction can be appropriately changed as long as a desired compound can be produced.

Method of Producing Carboxylic Acid-Type Lipid (III)

One example of a method of producing the carboxylic acid-type lipid (III) will be described. When two or more same symbols (e.g., L, X, p, q and the like) exist in a structure formula of one certain compound, the meanings of these same symbols may be the same or different as long as they are within the definition of the symbols. When the same symbols (e.g., L, X, p, q and the like) exist in structure formulas of two or more compounds, the meanings of these same symbols may be the same or different as long as they are within the definition of the symbols.

Step 1C

A compound (1) is provided.

Step 2C

A compound (2) is provided.

Step 3C

A compound (3) is provided, as necessary.

Step 4C

A compound (5) represented by formula (5) is provided.

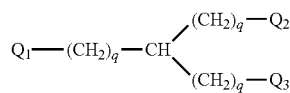
(5)

In formula (5), q is the same as defined above. A plurality of q's existing in formula (5) may represent the same integers or may represent different integers.

In formula (5), $Q_1$ is a functional group that can be reacted with the functional group $A_1$ of the compound (2) or the functional group $E_p$ of the compound (3), and is selected from a carboxyl group, an amino group, a hydroxyl group and a thiol group. Specific examples of a combination of functional groups that can be reacted are the same as the specific examples of the combination of the functional group $A_1$ and the functional group $D_1$.

In formula (5), $Q_2$ and $Q_3$ each independently represent a carboxyl group, an amino group, a hydroxyl group or a thiol group. $Q_2$ and $Q_3$ may be the same or different.

In formula (5), $Q_1$ may be the same as or different from one or both of $Q_2$ and $Q_3$. When $Q_1$ is different from one or both of $Q_2$ and $Q_3$, it becomes easy to select a protecting group for protection of $Q_1$. From this point of view, it is preferable that $Q_1$ is different from one or both of $Q_2$ and $Q_3$.

The compound (5) is not particularly limited as long as it is a trifunctional compound. The compound (5) is preferably trifunctional amino acid. The trifunctional amino acid is amino acid having a first functional group that is a carboxyl group, a second functional group that is an amino group and a third functional group selected from a carboxyl group, an amino group, a hydroxyl group and a thiol group. The third functional group is preferably different from one or both of the first and second functional groups. Examples of the trifunctional amino acid include amino acid having a carboxyl group and an amino group bonded to α-carbon and having a carboxyl group, an amino group, a hydroxyl group or a thiol group in a side chain. Examples of such amino acid include lysine, aspartic acid, glutamic acid, serine and the like.

Step 5C

A compound (6) represented by formula (6) is provided, as necessary.

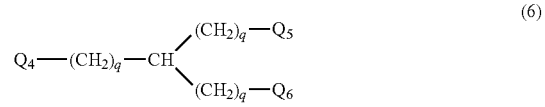
(6)

In formula (6), q is the same as defined above. A plurality of q's existing in formula (6) may represent the same integers or may represent different integers.

In formula (6), $Q_4$ is a functional group that can be reacted with $Q_2$ or $Q_3$ of the compound (5), $Q_5$ or $Q_6$ of another compound (6) or a functional group $G_p$ of a compound (7) mentioned later, and is selected from a carboxyl group, an amino group, a hydroxyl group and a thiol group. Specific examples of a combination of functional groups that can be reacted are the same as the specific examples of the combination of the functional group $A_1$ and the functional group $D_1$.

In formula (6), $Q_5$ and $Q_6$ each independently represent a carboxyl group, an amino group, a hydroxyl group or a thiol group. $Q_5$ and $Q_6$ may be the same or different.

In formula (6), $Q_4$ may be the same as or different from one or both of $Q_5$ and $Q_6$. When $Q_4$ is different from one or both of $Q_5$ and $Q_6$, it becomes easy to select a protecting group for protection of $Q_4$. From this point of view, it is preferable that $Q_4$ is different from one or both of $Q_5$ and $Q_6$.

The compound (6) is not particularly limited as long as it is a trifunctional compound. The compound (6) is preferably trifunctional amino acid. The description of the trifunctional amino acid is the same as mentioned above.

Step 6C

A compound (7) represented by formula (7):

(7)

wherein L and X are the same as defined above, and p represents an integer of 1 or more, and $F_1$ and $G_p$ each independently represent a carboxyl group, an amino group, a hydroxyl group or a thiol group, is provided, as necessary.

A functional group $F_1$ is a functional group that can be reacted with the functional group $Q_2$ or $Q_3$ of the compound (5) or the functional group $Q_5$ or $Q_6$ of the compound (6), and is selected from a carboxyl group, an amino group, a hydroxyl group and a thiol group. Specific examples of a combination of functional groups that can be reacted are the same as the specific examples of the combination of the functional group $A_1$ and the functional group $D_1$.

The compound (7) can be produced in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. The compound (7) may be a commercially available product.

One example of a method of producing the compound (7) is the same as one example of a method of producing the compound (3).

Step 7C

A compound (8) represented by formula (8):

$$H_1—X—[L—X]_{p-1}—I_p \quad (8)$$

wherein L and X are the same as defined above, and p represents an integer of 1 or more, and $H_1$ and $I_p$ each independently represent a carboxyl group, an amino group, a hydroxyl group or a thiol group, is provided, as necessary.

A functional group $H_1$ is a functional group that can be reacted with the functional group $Q_2$ or $Q_3$ of the compound (5) or the functional group $Q_5$ or $Q_6$ of the compound (6), and is selected from a carboxyl group, an amino group, a hydroxyl group and a thiol group. Specific examples of a combination of functional groups that can be reacted are the same as the specific examples of the combination of the functional group $A_1$ and the functional group $D_1$.

The compound (8) can be produced in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection by a protecting group can be performed in accordance with a conventional method. The compound (8) may be a commercially available product.

One example of a method of producing the compound (8) is the same as one example of a method of producing the compound (3).

Step 8C

A compound (9) represented by formula (9):

$$A_3\text{-}R \quad (9)$$

wherein R is the same as defined above, and $A_3$ represents a carboxyl group, an amino group, a hydroxyl group or a thiol group, is provided.

A functional group $A_3$ is a functional group that can be reacted with the functional group $Q_2$ or $Q_3$ of the compound (5), the functional group $Q_5$ or $Q_6$ of the compound (6) or the functional group $I_p$ of the compound (8), and is selected from a carboxyl group, an amino group, a hydroxyl group and a thiol group. Specific examples of a combination of functional groups that can be reacted are the same as the specific examples of the combination of the functional group $A_1$ and the functional group $D_1$.

The compound (9) can be produced in accordance with a conventional method. In this example, a functional group not involved in the reaction may be protected by a protecting group, as necessary. The protected functional group not involved in the reaction can be deprotected after reacting functional groups involved in the reaction with each other Protection by a protecting group and deprotection can be performed in accordance with a conventional method. The compound (9) may be a commercially available product.

Specific examples of the compound (9) are the same as the specific examples of the compound (4).

Step 9C

A compound (5-Y) represented by formula (5-Y) is produced by introducing a straight chain or a branched chain into the functional groups $Q_2$ and $Q_3$ of the compound (5). In formula (5-Y), Y is the same as defined above.

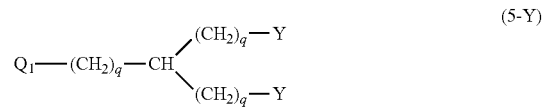

An example in which a straight chain or a branched chain is introduced into the functional group $Q_2$ of the compound (5) will be described, and a straight chain or a branched chain can also be similarly introduced into the functional group $Q_3$ of the compound (5).

When a straight chain is introduced into the functional group $Q_2$ of the compound (5), a compound (10) represented by formula (10) is produced.

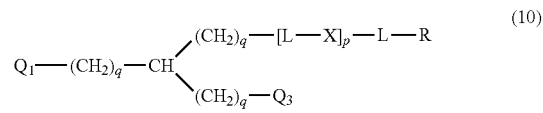

When p in formula (10) is 0, a compound (10) is produced by reacting the functional group $Q_2$ of the compound (5) with the functional group $A_3$ of the compound (9) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (10) is 1 or more, a compound (10) is produced: by reacting the functional group $Q_2$ of the compound (5) with the functional group $H_1$ of the compound (8) in accordance with a conventional method, and then reacting the functional group $I_p$ of the obtained compound with the functional group $A_3$ of the compound (9) in accordance with a conventional method; or by reacting the functional group $I_p$ of the compound (8) with the functional group $A_3$ of the compound (9) in accordance with a conventional method, and then reacting the functional group $H_1$ of the obtained compound with the functional group $Q_2$ of the compound (5) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When a branched chain is introduced into the functional group $Q_2$ of the compound (5), a compound (11) represented by formula (11) is produced.

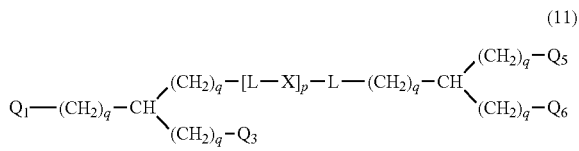

(11)

When p in formula (11) is 0, a compound (11) is produced by reacting the functional group $Q_2$ of the compound (5) with the functional group $Q_4$ of the compound (6) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (11) is 1 or more, a compound (11) is produced: by reacting the functional group $Q_2$ of the compound (5) with the functional group $F_1$ of the compound (7) in accordance with a conventional method, and then reacting the functional group $G_p$ of the obtained compound with the functional group $Q_4$ of the compound (6) in accordance with a conventional method; or by reacting the functional group $G_p$ of the compound (7) with the functional group $Q_4$ of the compound (6) in accordance with a conventional method, and then reacting the functional group $F_1$ of the obtained compound with the functional group $Q_2$ of the compound (5) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When a branched chain is introduced into the functional group $Q_2$ of the compound (5), after production of the compound (11), a straight chain or a branched chain is introduced into the functional groups $Q_5$ and $Q_6$ of the compound (11).

An example in which a straight chain or a branched chain is introduced into the functional group $Q_5$ of the compound (11) will be described, and a straight chain or a branched chain can also be similarly introduced into the functional group $Q_6$ of the compound (11).

When a straight chain is introduced into the functional group $Q_5$ of the compound (11), a compound (12) represented by formula (12) is produced.

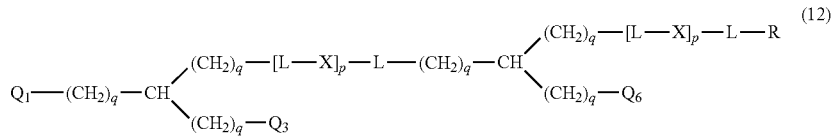

(12)

When p in formula (12) (p in $-(CH_2)_q-[L-X]_p-L-R$) is 0, a compound (12) is produced by reacting the functional group $Q_5$ of the compound (11) with the functional group $A_3$ of the compound (9) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (12) (p in $-(CH_2)_q-[L-X]_p-L-R$) is 1 or more, a compound (12) is produced: by reacting the functional group $Q_5$ of the compound (11) with the functional group $H_1$ of the compound (8) in accordance with a conventional method, and then reacting the functional group $I_p$ of the obtained compound with the functional group $A_3$ of the compound (9) in accordance with a conventional method; or by reacting the functional group $I_p$ of the compound (8) with the functional group $A_3$ of the compound (9) in accordance with a conventional method, and then reacting the functional group $H_1$ of the obtained compound with the functional group $Q_5$ of the compound (11) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When a branched chain is introduced into the functional group $Q_5$ of the compound (11), a compound (13) represented by formula (13) is produced.

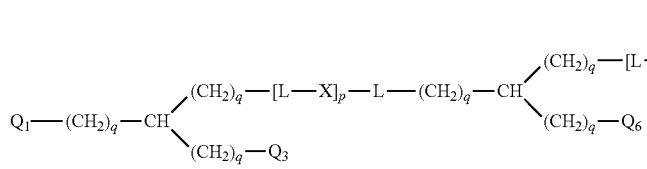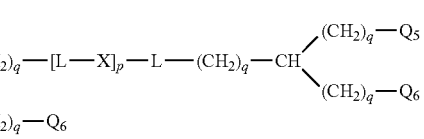

When p in formula (13) (p in $—(CH_2)_q$-[L-X]$_p$-L-$(CH_2)_q$—CH($—(CH_2)_q$-$Q_5$)($—(CH_2)_q$-$Q_6$)) is 0, a compound (13) is produced by reacting the functional group $Q_5$ of the compound (11) with the functional group $Q_4$ of the compound (6) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (13) (p in $—(CH_2)_q$-[L-X]$_p$-L-$(CH_2)_q$—CH($—(CH_2)_q$-$Q_5$)($—(CH_2)_q$-$Q_6$)) is 1 or more, a compound (13) is produced: by reacting the functional group $Q_5$ of the compound (11) with the functional group $F_1$ of the compound (7) in accordance with a conventional method, and then reacting the functional group $G_p$ of the obtained compound with the functional group $Q_4$ of the compound (6) in accordance with a conventional method; or by reacting the functional group $G_p$ of the compound (7) with the functional group $Q_4$ of the compound (6) in accordance with a conventional method, and then reacting the functional group $F_1$ of the obtained compound with the functional group $Q_5$ of the compound (11) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

A straight chain or a branched chain is introduced into newly introduced functional groups $Q_5$ and $Q_6$ in the same manner as mentioned above. By repeating this operation desired times, a branched chain having a desired number of branches is introduced into the functional group $Q_2$ of the compound (5). A straight chain is introduced into the last introduced functional groups $Q_5$ and $Q_6$ in the same manner as mentioned above. As a result, a compound (5-Y) is produced.

Step 10C

When p in formula (III) is 0, a carboxylic acid-type lipid (III) is produced: by reacting the functional group $Q_1$ of the compound (5-Y) with the functional group $A_1$ of the compound (2) in accordance with a conventional method, and then reacting the carboxyl group of the obtained compound with the amino group of the compound (1) in accordance with a conventional method; or by reacting the amino group of the compound (1) with the carboxyl group of the compound (2) in accordance with a conventional method, and then reacting the functional group $A_1$ of the obtained compound with the functional group $Q_1$ of the compound (5-Y) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (III) is 1 or more, a carboxylic acid-type lipid (III) is produced: by reacting the functional group $Q_1$ of the compound (5-Y) with the functional group $E_p$ of the compound (3) in accordance with a conventional method, then reacting the functional group $D_1$ of the obtained compound with the functional group $A_1$ of the compound (2) in accordance with a conventional method, and then reacting the carboxyl group of the obtained compound with the amino group of the compound (1) in accordance with a conventional method; or by reacting the amino group of the compound (1) with the carboxyl group of the compound (2) in accordance with a conventional method, then reacting the functional group $A_1$ of the obtained compound with the functional group $D_1$ of the compound (3) in accordance with a conventional method, and then reacting the functional group $E_p$ of the obtained compound with the functional group $Q_1$ of the compound (5-Y) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

As mentioned above, the carboxylic acid-type lipid (III) can be produced by a method including step 1C to step 10C. In each step, the order of reaction can be appropriately changed as long as a desired compound can be produced.

Method of Producing Carboxylic Acid-Type Lipid (IV)

One example of a method of producing the carboxylic acid-type lipid (IV) will be described.

Step 1D

A compound (1) is provided.

Step 2D

A compound (5) in which $Q_1$ is a carboxyl group is provided.

Step 3D

A carboxylic acid-type lipid (IV) is produced by reacting the functional group $Q_1$ (carboxyl group) of a compound (5-Y) produced by introducing a straight chain or a branched chain into the functional groups $Q_2$ and $Q_3$ of the compound (5) in the same manner as in step 9C with the amino group of the compound (1) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method.

As mentioned above, the carboxylic acid-type lipid (IV) can be produced by a method including step 1D to step 3D. In each step, the order of reaction can be appropriately changed as long as a desired compound can be produced.

Method of Producing Carboxylic Acid-Type Lipid (V)

One example of a method of producing the carboxylic acid-type lipid (V) will be described. When two or more same symbols (e.g., L, X, p, q and the like) exist in a structure formula of one certain compound, the meanings of these same symbols may be the same or different as long as they are within the definition of the symbols. When the same symbols (e.g., L, X, p, q and the like) exist in structure formulas of two or more compounds, the meanings of these same symbols may be the same or different as long as they are within the definition of the symbols.

Step 1E

A compound (1) is provided.

Step 2E

A compound (2) is provided.

Step 3E

A compound (3) is provided, as necessary.

Step 4E

A compound (14) represented by formula (14) is provided.

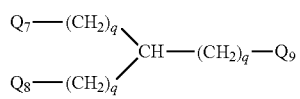

(14)

In formula (14), q is the same as defined above. A plurality of q's existing in formula (14) may represent the same integers or may represent different integers.

In formula (14), $Q_7$ and $Q_8$ are each independently functional groups that can be reacted with the amino group of the compound (1), the functional group $A_1$ of the compound (2), the functional group $E_p$ of the compound (3), a functional group $Q_{12}$ of a compound (15) mentioned later or a functional group $K_p$ of a compound (16) mentioned later, and are selected from a carboxyl group, an amino group, a hydroxyl group and a thiol group. Specific examples of a combination of functional groups that can be reacted are the same as the specific examples of the combination of the functional group $A_1$ and the functional group $D_1$. $Q_7$ and $Q_8$ may be the same or different.

In formula (14), $Q_9$ represents a carboxyl group, an amino group, a hydroxyl group or a thiol group.

In formula (14), $Q_9$ may be the same as or different from one or both of $Q_7$ and $Q_8$. When $Q_9$ is different from one or both of $Q_7$ and $Q_8$, it becomes easy to select a protecting group for protection of $Q_9$. From this point of view, it is preferable that $Q_9$ is different from one or both of $Q_7$ and $Q_8$.

The compound (14) is not particularly limited as long as it is a trifunctional compound. The compound (14) is preferably trifunctional amino acid. The description of the trifunctional amino acid is the same as mentioned above.

Step 5E

A compound (15) represented by formula (15) is provided, as necessary.

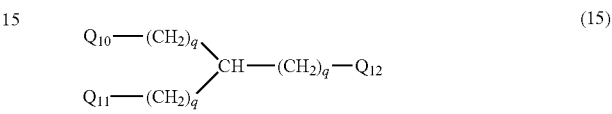

In formula (15), q is the same as defined above. A plurality of q's existing in formula (15) may represent the same integers or may represent different integers.

In formula (15), $Q_{10}$ and $Q_{11}$ are each independently functional groups that can be reacted with the amino group of the compound (1), the functional group $A_1$ of the compound (2), the functional group $E_p$ of the compound (3), a functional group $Q_{12}$ of another compound (15) or a functional group $K_p$ of a compound (16) mentioned later, and are selected from a carboxyl group, an amino group, a hydroxyl group and a thiol group. Specific examples of a combination of functional groups that can be reacted are the same as the specific examples of the combination of the functional group $A_1$ and the functional group $D_1$. $Q_{10}$ and $Q_{11}$ may be the same or different.

In formula (15), $Q_{12}$ represents a carboxyl group, an amino group, a hydroxyl group or a thiol group.

In formula (15), $Q_{12}$ may be the same as or different from one or both of $Q_{10}$ and $Q_{11}$. When $Q_{12}$ is different from one or both of $Q_{10}$ and $Q_{11}$, it becomes easy to select a protecting group for protection of $Q_{12}$. From this point of view, it is preferable that $Q_{12}$ is different from one or both of $Q_{10}$ and $Q_{11}$.

The compound (15) is not particularly limited as long as it is a trifunctional compound. The compound (15) is preferably trifunctional amino acid. The description of the trifunctional amino acid is the same as mentioned above.

Step 6E

A compound (16) represented by formula (16):

$$J_1\text{-}X\text{-}[L\text{-}X]_{p-1}\text{—}K_p \qquad (16)$$

wherein L and X are the same as defined above, and p represents an integer of 1 or more, and $J_1$ and $K_p$ each independently represent a carboxyl group, an amino group, a hydroxyl group or a thiol group, is provided, as necessary.

A functional group $J_1$ is a functional group that can be reacted with the functional group $Q_{12}$ of the compound (15), and is selected from a carboxyl group, an amino group, a hydroxyl group and a thiol group. Specific examples of a combination of functional groups that can be reacted are the same as the specific examples of the combination of the functional group $A_1$ and the functional group $D_1$.

The compound (16) can be produced in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. The compound (16) may be a commercially available product.

One example of a method of producing the compound (16) is the same as one example of a method of producing the compound (3).

Step 7E

A compound (17) represented by formula (17):

  (17)

wherein L and X are the same as defined above, and p represents an integer of 1 or more, and $T_1$ and $U_p$ each independently represent a carboxyl group, an amino group, a hydroxyl group or a thiol group, is provided, as necessary.

A functional group $T_1$ is a functional group that can be reacted with the functional group $Q_9$ of the compound (14), and is selected from a carboxyl group, an amino group, a hydroxyl group and a thiol group. Specific examples of a combination of functional groups that can be reacted are the same as the specific examples of the combination of the functional group $A_1$ and the functional group $D_1$.

The compound (17) can be produced in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. The compound (17) may be a commercially available product.

One example of a method of producing the compound (17) is the same as one example of a method of producing the compound (3).

Step 8E

A compound (18) represented by formula (18):

$A_4$-R  (18)

wherein R is the same as defined above, and $A_4$ represents a carboxyl group, an amino group, a hydroxyl group or a thiol group, is provided.

A functional group $A_4$ is a functional group that can be reacted with the functional group $Q_9$ of the compound (14) or the functional group $U_p$ of the compound (17), and is selected from a carboxyl group, an amino group, a hydroxyl group and a thiol group. Specific examples of a combination of functional groups that can be reacted are the same as the specific examples of the combination of the functional group $A_1$ and the functional group $D_1$.

The compound (18) can be produced in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. The compound (18) may be a commercially available product. Specific examples of the compound (18) are the same as the specific examples of the compound (4).

Step 9E

A compound (14-Z) represented by formula (14-Z) is produced by introducing a straight chain or a branched chain into the functional groups $Q_7$ and $Q_8$ of the compound (14). In formula (14-Z), Z is the same as defined above.

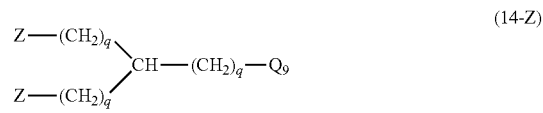  (14-Z)

An example in which a straight chain or a branched chain is introduced into the functional group $Q_7$ of the compound (14) will be described, and a straight chain or a branched chain can also be similarly introduced into the functional group $Q_8$ of the compound (14).

When a straight chain represented by formula (X) is introduced into the functional group $Q_7$ of the compound (14), a compound (19) represented by formula (19) is produced.

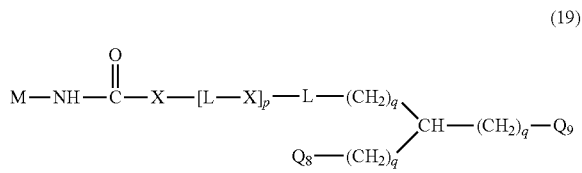  (19)

When p in formula (19) is 0, a compound (19) is produced: by reacting the functional group $Q_7$ of the compound (14) with the functional group $A_1$ of the compound (2) in accordance with a conventional method, and then reacting the carboxyl group of the obtained compound with the amino group of the compound (1) in accordance with a conventional method; or by reacting the amino group of the compound (1) with the carboxyl group of the compound (2) in accordance with a conventional method, and then reacting the functional group $A_1$ of the obtained compound with the functional group $Q_7$ of the compound (14) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (19) is 1 or more, a compound (19) is produced: by reacting the functional group $Q_7$ of the compound (14) with the functional group $E_p$ of the compound (3) in accordance with a conventional method, then reacting the functional group $D_1$ of the obtained compound with the functional group $A_1$ of the compound (2) in accordance with a conventional method, and then reacting the carboxyl group of the obtained compound with the amino group of the compound (1) in accordance with a conventional method; or by reacting the amino group of the compound (1) with the carboxyl group of the compound (2) in accordance with a conventional method, then reacting the functional group $A_1$ of the obtained compound with the functional group $D_1$ of the compound (3) in accordance with a conventional method, and then reacting the functional group $E_p$ of the obtained compound with the functional group $Q_7$ of the compound (14) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When a straight chain represented by formula (XI) is introduced into the functional group $Q_7$ of the compound (14), a compound (20) represented by formula (20) is produced.

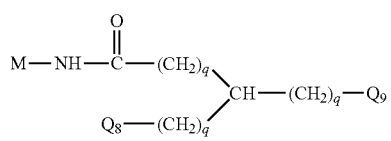

When a straight chain represented by formula (XI) is introduced into the functional group $Q_7$ of the compound (14), the functional group $Q_7$ of the compound (14) is a carboxyl group. When a straight chain represented by formula (XI) is introduced into the functional group $Q_8$ of the compound (14), the functional group $Q_8$ of the compound (14) is a carboxyl group. A compound (20) is produced by reacting the functional group $Q_7$ (carboxyl group) of the compound (14) with the amino group of the compound (1) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method.

When a branched chain is introduced into the functional group $Q_7$ of the compound (14), a compound (21) represented by formula (21) is produced.

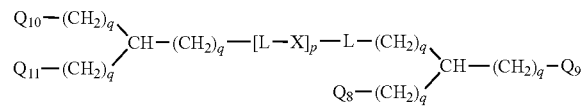

When p in formula (21) is 0, a compound (21) is produced by reacting the functional group $Q_7$ of the compound (14) with the functional group $Q_{12}$ of the compound (15). In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (21) is 1 or more, a compound (21) is produced: by reacting the functional group $Q_7$ of the compound (14) with the functional group $K_p$ of the compound (16) in accordance with a conventional method, and then reacting the functional group $J_1$ of the obtained compound with the functional group $Q_{12}$ of the compound (15) in accordance with a conventional method; or by reacting the functional group $J_1$ of the compound (16) with the functional group $Q_{12}$ of the compound (15) in accordance with a conventional method, and then reacting the functional group $K_p$ of the obtained compound with the functional group $Q_7$ of the compound (14). In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When a branched chain is introduced into the functional group $Q_7$ of the compound (14), after production of the compound (21), a straight chain or a branched chain is introduced into the functional groups $Q_{10}$ and $Q_{11}$ of the compound (21).

An example in which a straight chain or a branched chain is introduced into the functional group $Q_{10}$ of the compound (21) will be described, and a straight chain or a branched chain can also be similarly introduced into the functional group $Q_{11}$ of the compound (21).

When a straight chain represented by formula (X) is introduced into the functional group $Q_{10}$ of the compound (21), a compound (22) represented by formula (22) is produced.

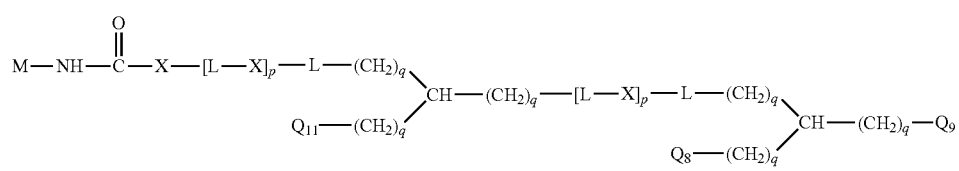

When p in formula (22) (p in M-NH—CO—X-[L-X]$_p$-L-) is 0, a compound (22) is produced: by reacting the functional group $Q_{10}$ of the compound (21) with the functional group $A_1$ of the compound (2) in accordance with a conventional method, and then reacting the carboxyl group of the obtained compound with the amino group of the compound (1) in accordance with a conventional method; or by reacting the amino group of the compound (1) with the carboxyl group of the compound (2) in accordance with a conventional method, and then reacting the functional group $A_1$ of the When a straight chain represented by formula (XI) is introduced into the functional group $Q_{10}$ of the compound (21), a compound (23) represented by formula (23) is produced.

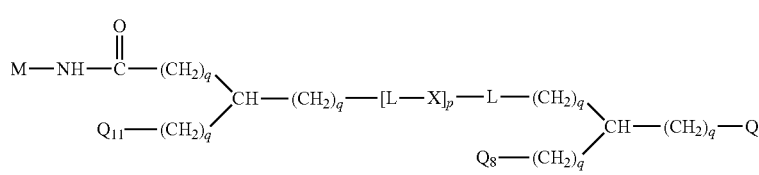

(23)

obtained compound with the functional group $Q_{10}$ of the compound (21) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (22) (p in M-NH—CO—X-[L-X]$_p$-L-) is 1 or more, a compound (22) is produced: by reacting the functional group $Q_{10}$ of the compound (21) with the functional group $E_p$ of the compound (3) in accordance with a conventional method, then reacting the functional group $D_1$ of the obtained compound with the functional group $A_1$ of When a straight chain represented by formula (XI) is introduced into the functional group $Q_{10}$ of the compound (21), the functional group $Q_{10}$ of the compound (21) is a carboxyl group. When a straight chain represented by formula (XI) is introduced into the functional group $Q_{11}$ of the compound (21), the functional group $Q_{11}$ of the compound (21) is a carboxyl group. A compound (23) is produced by reacting the functional group $Q_{10}$ (carboxyl group) of the compound (21) with the amino group of the compound (1) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method.

When a branched chain is introduced into the functional group $Q_{10}$ of the compound (21), a compound (24) represented by formula (24) is produced.

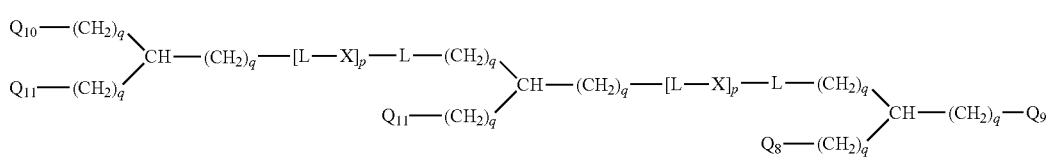

(24)

the compound (2) in accordance with a conventional method, and then reacting the carboxyl group of the obtained compound with the amino group of the compound (1) in accordance with a conventional method; or by reacting the amino group of the compound (1) with the carboxyl group of the compound (2) in accordance with a conventional method, then reacting the functional group $A_1$ of the obtained compound with the functional group $D_1$ of the compound (3) in accordance with a conventional method, and then reacting the functional group $E_p$ of the obtained compound with the functional group $Q_{10}$ of the compound (21) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (24) (p in $(Q_{10}$-$(CH_2)_q$—$)(Q_{11}$-$(CH_2)_q$—$)CH$—$(CH_2)_q$-$[L$-$X]_p$-$L$-) is 0, a compound (24) is produced by reacting the functional group $Q_{10}$ of the compound (21) with the functional group $Q_{12}$ of the compound (15). In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (24) (p in $(Q_{10}$-$(CH_2)_q$—$)(Q_{11}$-$(CH_2)_q$—$)CH$—$(CH_2)_q$-$[L$-$X]_p$-$L$-) is 1 or more, a compound (24) is produced: by reacting the functional group $Q_{10}$ of the compound (21) with the functional group $K_p$ of the compound (16) in accordance with a conventional method, and then reacting the functional group $J_1$ of the obtained compound with the functional group $Q_{12}$ of the compound (15) in accordance with a conventional method; or by reacting the functional group $J_1$ of the compound (16) with the functional group $Q_{12}$ of the compound (15) in accordance with a conventional method, and then reacting the functional group $K_p$ of the obtained compound with the functional group $Q_{10}$ of the compound (21). In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

A straight chain or a branched chain is introduced into newly introduced functional groups $Q_{10}$ and $Q_{11}$ in the same manner as mentioned above. By repeating this operation desired times, a branched chain having a desired number of branches can be introduced into the functional group $Q_7$ of the compound (14). A straight chain is introduced into the last introduced functional groups $Q_{10}$ and $Q_{11}$ in the same manner as mentioned above. As a result, a compound (14-Z) is produced.

Step 10E

When p in formula (V) is 0, a carboxylic acid-type lipid (V) is produced by reacting the functional group $Q_9$ of the compound (14-Z) with the functional group $A_4$ of the compound (18) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (V) is 1 or more, a carboxylic acid-type lipid (V) is produced: by reacting the functional group $Q_9$ of the compound (14-Z) with the functional group $T_1$ of the compound (17) in accordance with a conventional method, and then reacting the functional group $U_p$ of the obtained compound with the functional group $A_4$ of the compound (18) in accordance with a conventional method; or by reacting the functional group $U_p$ of the compound (17) with the functional group $A_4$ of the compound (18) in accordance with a conventional method, and then reacting the functional group $T_1$ of the obtained compound with the functional group $Q_9$ of the compound (14-Z) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

As mentioned above, the carboxylic acid-type lipid (V) can be produced by a method including step 1E to step 10E. In each step, the order of reaction can be appropriately changed as long as a desired compound can be produced.

Method of Producing Carboxylic Acid-Type Lipid (VI)

One example of a method of producing the carboxylic acid-type lipid (VI) will be described. When two or more same symbols (e.g., L, X, p, q and the like) exist in a structure formula of one certain compound, the meanings of these same symbols may be the same or different as long as they are within the definition of the symbols. When the same symbols (e.g., L, X, p, q and the like) exist in structure formulas of two or more compounds, the meanings of these same symbols may be the same or different as long as they are within the definition of the symbols.

Step 1F

A compound (5-Y) is produced by introducing a straight chain or a branched chain into the functional groups $Q_2$ and $Q_3$ of the compound (5) in the same manner as in step 9C.

In the compound (5-Y) produced in step 1F, $Q_1$ is a functional group that can be reacted with $Q_9$ of a compound (14-Z) produced in step 2F or a functional group $W_p$ of a compound (25) prepared in step 3F, and is selected from a carboxyl group, an amino group, a hydroxyl group and a thiol group. Specific examples of a combination of functional groups that can be reacted are the same as the specific examples of the combination of the functional group $A_1$ and the functional group $D_1$.

Step 2F

A compound (14-Z) is produced by introducing a straight chain or a branched chain into the functional group $Q_7$ and $Q_8$ of the compound (14) in the same manner as in step 9E.

Step 3F

A compound (25) represented by formula (25):

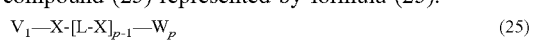

$$V_1-X-[L-X]_{p-1}-W_p \qquad (25)$$

wherein L and X are the same as defined above, and p represents an integer of 1 or more, and $V_1$ and $W_p$ each independently represent a carboxyl group, an amino group, a hydroxyl group or a thiol group, is provided, as necessary.

A functional group $V_1$ is a functional group that can be reacted with the functional group $Q_9$ of the compound (14-Z), and is selected from a carboxyl group, an amino group, a hydroxyl group and a thiol group. Specific examples of a combination of functional groups that can be reacted are the same as the specific examples of the combination of the functional group $A_1$ and the functional group $D_1$.

A functional group $W_p$ is a functional group that can be reacted with the functional group $Q_1$ of the compound (5-Y), and is selected from a carboxyl group, an amino group, a hydroxyl group and a thiol group. Specific examples of a combination of functional groups that can be reacted are the same as the specific examples of the combination of the functional group $A_1$ and the functional group $D_1$.

The compound (25) can be produced in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. The compound (25) may be a commercially available product.

One example of a method of producing the compound (25) is the same as one example of a method of producing the compound (3).

Step 4F

When p in formula (VI) is 0, a carboxylic acid-type lipid (VI) is produced by reacting the functional group $Q_9$ of the compound (14-Z) with the functional group $Q_1$ of the compound (5-Y) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

When p in formula (VI) is 1 or more, a carboxylic acid-type lipid (VI) is produced: by reacting the functional group $Q_9$ of the compound (14-Z) with the functional group $V_1$ of the compound (25) in accordance with a conventional method, and then reacting the functional group $W_p$ of the obtained compound with the functional group $Q_1$ of the compound (5-Y) in accordance with a conventional method; or by reacting the functional group $W_p$ of the compound (25) with the functional group $Q_1$ of the compound (5-Y) in accordance with a conventional method, and then reacting the functional group $V_1$ of the obtained compound with the functional group $Q_9$ of the compound (14-Z) in accordance with a conventional method. In this example, a functional group not involved in the reaction may be protected by a protecting group, as necessary. The protected functional group not involved in the reaction can be deprotected after reacting functional groups involved in the reaction with each other. Protection by a protecting group and deprotection can be performed in accordance with a conventional method. Specific examples of L formed by the reaction of two functional groups are the same as the specific examples of L formed by the reaction of the functional group $E_1$ and the functional group $D_2$.

As mentioned above, the carboxylic acid-type lipid (VI) can be produced by a method including step 1F to step 4F. In each step, the order of reaction can be appropriately changed as long as a desired compound can be produced.

Other Lipids

The lipid particle and the lipid membrane may include one or two or more lipids other than the carboxylic acid-type lipid. Examples of the lipid other than the carboxylic acid-type lipid include a phospholipid, a glycolipid, a sterol and the like. The phospholipid, the glycolipid and the sterol will be described.

Phospholipid

Examples of the phospholipid include a glycerophospholipid, a sphingophospholipid, a cardiolipin and the like. The phospholipid may be a phospholipid that is negatively charged at physiological pH, or may be a phospholipid that is amphoteric (i.e., has a moiety that is negatively charged and a moiety that is positively charged, and is electrically neutral as a whole) at physiological pH. The phospholipid also includes a salt formed by a phosphoric acid group possessed by the phospholipid, and examples of the salt of a phosphoric acid group include a calcium salt, a magnesium salt, a potassium salt and the like. Regarding the phospholipid, one phospholipid may be used alone, or two or more phospholipids may be used in combination. The glycerophospholipid, the sphingophospholipid and the cardiolipin will be described.

Glycerophospholipid

Examples of the glycerophospholipid include a lipid having a structure represented by formula (i). The glycerophospholipid may be a glycerophospholipid that is negatively charged at physiological pH, or may be a glycerophospholipid that is amphoteric at physiological pH. Examples of the glycerophospholipid that is negatively charged at physiological pH include a glycerophospholipid in which a group represented by $X_1$ in formula (i) is a group other than a cationic group (anionic group or electrically neutral group). Examples of the glycerophospholipid that is amphoteric at physiological pH include a glycerophospholipid in which a group represented by $X_1$ in formula (i) is a cationic group.

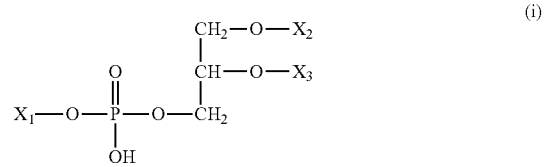

In formula (i), $X_1$ represents hydrogen, a choline residue, a serine residue, an inositol residue, a glycerol residue or an ethanolamine residue. A group represented by $X_1$ may be a cationic group, or may be a group other than a cationic group (anionic group or electrically neutral group). The choline residue is a cationic group, and the serine residue, the inositol residue and the glycerol residue are groups other than a cationic group.

In formula (i), $X_2$ and $X_3$ each independently represent hydrogen, a saturated or unsaturated acyl group (—CO—R, R is a hydrocarbon group) or a hydrocarbon group. Specific examples of the hydrocarbon group included in the acyl group represented by $X_2$ or $X_3$, and specific examples of the hydrocarbon group represented by $X_2$ or $X_3$ are the same as mentioned above. It is preferable that at least one of $X_2$ or $X_3$ is a saturated or unsaturated acyl group, and it is further preferable that both $X_2$ or $X_3$ are saturated or unsaturated acyl groups. When both $X_2$ or $X_3$ are acyl groups, two acyl groups may be the same or different.

Examples of the glycerophospholipid include phosphatidic acid, phosphatidylcholine, phosphatidylserine, phosphatidylinositol, phosphatidylglycerol, phosphatidylethanolamine and the like. Of these, phosphatidylserine and phosphatidylglycerol are preferable.

Examples of the phosphatidic acid include dipalmitoylphosphatidic acid, distearoylphosphatidic acid, dimyristoylphosphatidic acid, dioleylphosphatidic acid and the like.

Examples of the phosphatidylcholine include dipalmitoylphosphatidylcholine, distearoylphosphatidylcholine, dimyristoylphosphatidylcholine, dioleoylphosphatidylcholine, dilauroylphosphatidylcholine, didecanoylphosphatidylcholine, dioctanoylphosphatidylcholine, dihexanoylphosphatidylcholine, dibutyrylphosphatidylcholine, dielaidoylphosphatidylcholine, dilinoleoylphosphatidylcholine, diarachidonoylphosphatidylcholine, diicosenoylphosphatidylcholine, diheptanoylphosphatidylcholine, dicaproylphosphatidylcholine, diheptadecanoylphosphatidylcholine, dibehenoylphosphatidylcholine, eleostearoylphosphatidylcholine, hydrogenated egg phosphatidylcholine, hydrogenated soy phosphatidylcholine, 1-palmitoyl-2-arachidonoylphosphatidylcholine, 1-palmitoyl-2-oleoylphosphatidylcholine, 1-palmitoyl-2-linoleoylphosphatidylcholine, 1-palmitoyl-2-myristoylphosphatidylcholine, 1-palmitoyl-2-stearoylphosphatidylcholine, 1-stearoyl-2-palmitoylphosphatidylcholine, 1,2-dimyristoylamide-1,2-deoxyphosphatidylcholine, 1-myristoyl-2-palmitoylphosphatidylcholine, 1-myristoyl-2-stearoylphosphatidylcholine, di-O-hexadecylphosphatidylcholine, transdielaidoylphosphatidylcholine, dipalmitelaidoyl-phosphatidylcholine, n-octadecyl-2- methylphosphatidylcholine, n-octadecylphosphatidylcholine, 1-laurylpropanediol-3-phosphocholine, erythro-N-lignoceroylsphingophosphatidylcholine, palmitoyl-(9-cis-octadecenoyl)-3-sn-phosphatidylcholine and the like.

Examples of the phosphatidylserine include distearoylphosphatidylserine, dimyristoylphosphatidylserine, dilauroylphosphatidylserine, dipalmitoylphosphatidylserine, dioleoylphosphatidylserine, eleostearoylphosphatidylserine, 1,2-di-(9-cis-octadecenoyl)-3-sn-phosphatidylserine and the like.

Examples of the phosphatidylinositol include dipalmitoylphosphatidylinositol, distearoylphosphatidylinositol, dilauroylphosphatidylinositol and the like.

Examples of the phosphatidylglycerol include dipalmitoylphosphatidylglycerol, distearoylphosphatidylglycerol, dioleoylphosphatidylglycerol, dilauroylphosphatidylglycerol, dimyristoylphosphatidylglycerol, hydrogenated soy phosphatidylglycerol, hydrogenated egg phosphatidylglycerol and the like.

Examples of the phosphatidylethanolamine include dipalmitoylphosphatidylethanolamine, distearoylphosphatidylethanolamine, dioleoylphosphatidylethanolamine, dilauroylphosphatidylethanolamine, dimyristoylphosphatidylethanolamine, didecanoylphosphatidylethanolamine, N-glutarylphosphatidylethanolamine, N-(7-nitro-2,1,3-benzoxydiazol-4-yl)-1,2-dioleoyl-sn-phosphatidylethanolamine, eleostearoylphosphatidylethanolamine, N-succinyldioleoylphosphatidylethanolamine, 1-hexadecyl-2-palmitoylglycerophosphatidylethanolamine and the like.

In phosphatidic acid, phosphatidylcholine, phosphatidylserine, phosphatidylinositol, phosphatidylglycerol and phosphatidylethanolamine, the number of carbon atoms of the hydrocarbon group included in the acyl group represented by $X_2$ or $X_3$, and the number of carbon atoms of the hydrocarbon group represented by $X_2$ or $X_3$ is preferably 10 to 24, more preferably 12 to 22, and still more preferably 14 to 18.

The glycerophospholipid is preferably dipalmitoylphosphatidylcholine, dipalmitoylphosphatidylserine, dipalmitoylphosphatidylglycerol, dipalmitoylphosphatidylethanolamine and the like.

Sphingophospholipid

Examples of the sphingophospholipid include a lipid having a structure represented by formula (ii). The sphingophospholipid may be a sphingophospholipid that is negatively charged at physiological pH, or may be a sphingophospholipid that is amphoteric at physiological pH. Examples of the sphingophospholipid that is negatively charged at physiological pH include a sphingophospholipid in which a group represented by $X_4$ in formula (ii) is a group other than a cationic group (anionic group or electrically neutral group). Examples of the sphingophospholipid that is amphoteric at physiological pH include a sphingophospholipid in which a group represented by $X_4$ in formula (ii) is a cationic group.

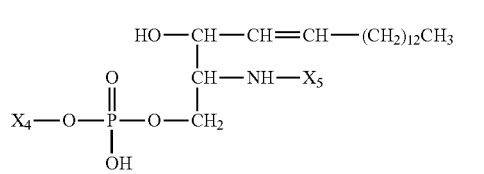

In formula (ii), $X_4$ represents hydrogen, a choline residue, a serine residue, an inositol residue, a glycerol residue or an ethanolamine residue. A group represented by $X_4$ may be a cationic group, or may be a group other than a cationic group (anionic group or electrically neutral group). The choline residue is a cationic group, and the serine residue, the inositol residue and the glycerol residue are groups other than a cationic group.

In formula (ii), $X_5$ represents hydrogen or a saturated or unsaturated acyl group. $X_5$ represents preferably a saturated or unsaturated acyl group. Specific examples of the hydrocarbon group included in the acyl group are the same as mentioned above. The number of carbon atoms of the hydrocarbon group included in the acyl group is preferably 10 to 24, more preferably 12 to 22, and still more preferably 14 to 18.

Examples of the sphingophospholipid include sphingomyelin, dipalmitoyl sphingomyelin, distearoyl sphingomyelin, ceramide ciliatine, ceramide phosphorylethanolamine, ceramide phosphorylglycerol and the like.

Cardiolipin

Examples of the cardiolipin include a lipid having a structure represented by formula (iii). The cardiolipin may be a cardiolipin that is negatively charged at physiological pH, or may be a cardiolipin that is amphoteric at physiological pH.

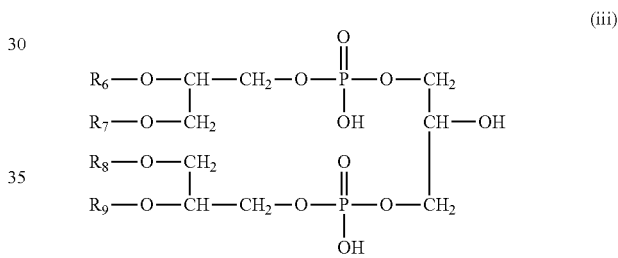

In formula (iii), $R_6$ to $R_9$ each independently represent hydrogen or a saturated or unsaturated acyl group, at least one of $R_6$ to $R_9$ is a saturated or unsaturated acyl group. It is preferable that two to four of $R_6$ to $R_9$ are acyl groups, it is more preferable that three to four of $R_6$ to $R_9$ are acyl groups, and it is still more preferable that all of $R_6$ to $R_9$ are acyl groups. When two or more of $R_6$ to $R_9$ are acyl groups, two or more acyl groups may be the same or different. Specific examples of the hydrocarbon group included in the acyl group are the same as mentioned above. The number of carbon atoms of the hydrocarbon group included in the acyl group is preferably 10 to 24, more preferably 12 to 22, and still more preferably 14 to 18.

Glycolipid

Examples of the glycolipid include a glyceroglycolipid, a sphingoglycolipid and the like. When two or more acyl groups are included in the glycolipid, two or more acyl groups may be the same or different. Specific examples of the hydrocarbon group included in the acyl group are the same as mentioned above. The number of carbon atoms of the hydrocarbon group included in the acyl group is preferably 1 to 4, more preferably 1 to 2, and still more preferably 2. Regarding the glycolipid, one glycolipid may be used alone, or two or more glycolipids may be used in combination.

Examples of the glyceroglycolipid include diglycosyl diglyceride, glycosyl diglyceride, digalactosyl diglyceride, galactosyl diglyceride, sulfoxyribosyl diglyceride, (1,3)-D- mannosyl(1,3)diglyceride, digalactosyl glyceride, digalactosyl dilauroyl glyceride, digalactosyl dimyristoyl glyceride, digalactosyl dipalmitoyl glyceride, digalactosyl distearoyl glyceride, galactosyl glyceride, galactosyl dilauroyl glyceride, galactosyl dimyristoyl glyceride, galactosyl dipalmitoyl glyceride, galactosyl distearoyl glyceride, digalactosyldiacylglycerol and the like.

Examples of the sphingoglycolipid include ceramide (cerebroside), galactosylceramide, lactosylceramide, digalactosylceramide, ganglioside GM1, ganglioside GM2, ganglioside GM3, sulfatide, ceramide oligohexoside, globoside and the like.

Sterol

Examples of the sterol include cholesterol, cholesterol succinate, dihydrocholesterol, lanosterol, dihydrolanosterol, desmosterol, stigmasterol, sitosterol, campesterol, brassicasterol, zymosterol, ergosterol, campesterol, fucosterol, 22-ketosterol, 20-hydroxysterol, 7-hydroxycholesterol, 19-hydroxycholesterol, 22-hydroxycholesterol, 25-hydroxycholesterol, 7-dehydrocholesterol, 5α-cholest-7-en-3β-ol, epicholesterol, dehydroergosterol, cholesterol sulfate, cholesterol hemisuccinate, cholesterol phthalate, cholesterol phosphate, cholesterol valerate, cholesterol hemisuccinate, 3βN—(N',N'-dimethylaminoethane)-carbamoyl cholesterol, cholesterol acetate, cholesteryl oleate, cholesteryl linoleate, cholesteryl myristate, cholesteryl palmitate, cholesteryl arachidate, coprostanol, cholesterol ester, cholesteryl phosphorylcholine, 3,6,9-trioxaoctan-1-ol-cholesteryl-3e-ol and the like. Regarding the sterol, one sterol may be used alone, or two or more sterols may be used in combination.

Fatty Acid

The lipid particle and the lipid membrane may include a fatty acid. The fatty acid may be saturated fatty acid or unsaturated fatty acid. The number of carbon atoms of fatty acid is not particularly limited, and is 10 to 24, more preferably 12 to 22, and still more preferably 14 to 18. Examples of the fatty acid include caprylic acid, pelargonic acid, capric acid, undecylenic acid, lauric acid, tridecylenic acid, myristic acid, pentadecylenic acid, palmitic acid, margaric acid, stearic acid, nonadecylenic acid, arachidic acid, dodecenoic acid, tetradecenoic acid, oleic acid, linoleic acid, linoleic acid, eicosenoic acid, erucic acid, docosapentaenoic acid and the like. Regarding the fatty acid, one fatty acid may be used alone, or two or more fatty acids may be used in combination.

The phospholipid, the glycolipid, the sterol and the like may be modified by a hydrophilic polymer and the like. Examples of the hydrophilic polymer include polyethylene glycol (PEG), polyglycerin, polypropylene glycol, polyvinyl alcohol, styrene-maleic anhydride alternating copolymer, polyvinylpyrrolidone, synthetic polyamino acid and the like. Regarding these hydrophilic polymers, one hydrophilic polymer may be used alone, or two or more hydrophilic polymers may be used in combination.

Preferably, the lipid particle or the lipid membrane comprises our carboxylic acid-type lipid and at least one selected from the group consisting of a phospholipid and a sterol.

The content of a phospholipid is preferably 0 to 95 mol %, more preferably 0 to 50 mol %, and still more preferably 0 to 30 mol %, based on the total lipid amount included in our lipid particle or our lipid membrane. The molar ratio of the content of a phospholipid to the content of our carboxylic acid-type lipid (content of a phospholipid:content of our carboxylic acid-type lipid) is preferably 0:1 to 19:1, more preferably 0:1 to 10:1, and still more preferably 0:1 to 1:1.

The content of a sterol is preferably 0 to 50 mol %, more preferably 0 to 40 mol %, and still more preferably 0 to 30 mol %, based on the total lipid amount included in our lipid particle or our lipid membrane. The molar ratio of the content of a sterol to the content of our carboxylic acid-type lipid (the content of a sterol:the content of our carboxylic acid-type lipid) is preferably 0:1 to 9:1, more preferably 0:1 to 5:1, and still more preferably 0:1 to 1:1.

Specific combinations of a carboxylic acid-type lipid, a phospholipid and a sterol can be appropriately selected from the carboxylic acid-type lipids, the phospholipids and the sterols mentioned above.

When the lipid particle or the lipid membrane comprises our carboxylic acid-type lipid and a phospholipid, preferably, the carboxylic acid-type lipid is a carboxylic acid-type lipid in which M in formulas (I) to (VI) is an aspartic acid residue, a glutamic acid residue, an AG residue or a salt thereof, and the phospholipid is at least one glycerophospholipid selected from the group consisting of dipalmitoylphosphatidylcholine, dipalmitoylphosphatidylserine, dipalmitoylphosphatidylglycerol and dipalmitoylphosphatidylethanolamine. More preferably, the carboxylic acid-type lipid is a carboxylic acid-type lipid in which M in formulas (I) to (VI) is an aspartic acid residue, a glutamic acid residue, an AG residue or a salt thereof, and the phospholipid is at least one glycerophospholipid selected from the group consisting of dipalmitoylphosphatidylcholine, dipalmitoylphosphatidylserine and dipalmitoylphosphatidylglycerol. Still more preferably, the carboxylic acid-type lipid is a carboxylic acid-type lipid in which M in formulas (I) to (VI) is an aspartic acid residue, a glutamic acid residue, an AG residue or a salt thereof, and the phospholipid is at least one glycerophospholipid selected from the group consisting of dipalmitoylphosphatidylserine and dipalmitoylphosphatidylglycerol.

When the lipid particle or the lipid membrane comprises the carboxylic acid-type lipid and a sterol, preferably, the carboxylic acid-type lipid is a carboxylic acid-type lipid in which M in formulas (I) to (VI) is an aspartic acid residue, a glutamic acid residue, an AG residue or a salt thereof, and the sterol is cholesterol.

When the lipid particle or the lipid membrane comprises the carboxylic acid-type lipid, a phospholipid and a sterol, preferably, the carboxylic acid-type lipid is a carboxylic acid-type lipid in which M in formulas (I) to (VI) is an aspartic acid residue, a glutamic acid residue, an AG residue or a salt thereof, the phospholipid is at least one glycerophospholipid selected from the group consisting of dipalmitoylphosphatidylcholine, dipalmitoylphosphatidylserine, dipalmitoylphosphatidylglycerol and dipalmitoylphosphatidylethanolamine, and the sterol is cholesterol. More preferably, the carboxylic acid-type lipid is a carboxylic acid-type lipid in which M in formulas (I) to (VI) is an aspartic acid residue, a glutamic acid residue, an AG residue or a salt thereof, the phospholipid is at least one glycerophospholipid selected from the group consisting of dipalmitoylphosphatidylcholine, dipalmitoylphosphatidylserine and dipalmitoylphosphatidylglycerol, and the sterol is cholesterol. Still more preferably, the carboxylic acid-type lipid is a carboxylic acid-type lipid in which M in formulas (I) to (VI) is an aspartic acid residue, a glutamic acid residue, an AG residue or a salt thereof, the phospholipid is at least one glycerophospholipid selected from the group consisting of dipalmitoylphosphatidylserine and dipalmitoylphosphatidylglycerol, and the sterol is cholesterol.

Application

Since the carboxylic acid-type lipid is negatively charged at physiological pH, the surfaces of the lipid particle and the lipid membrane are negatively charged at physiological pH. Therefore, when the lipid particle and the lipid membrane come into contact with blood and are hydrated by moisture in the blood, the surfaces of the lipid particle and the lipid membrane are negatively charged, and at least a part of the lipid particle and the lipid membrane can bind to a plurality of platelets (particularly, activated platelets) via an electrostatic interaction. As a result of this, the lipid particle and the lipid membrane can accelerate adhesion and/or aggregation of platelets, and in turn can accelerate blood coagulation. This does not mean that the platelet adhesion accelerating effect and/or the platelet aggregation accelerating effect evoked by the lipid particle and the lipid membrane cannot be involved in an interaction other than an electrostatic interaction such as the van der Waals force.

Since the carboxylic acid-type lipid, the lipid particle and the lipid membrane have the platelet adhesion accelerating effect and/or the platelet aggregation accelerating effect, they are useful as a platelet adhesion accelerating agent, a platelet aggregation accelerating agent and a platelet substitute (artificial platelet). The carboxylic acid-type lipid, the lipid particle and the lipid membrane are also useful as a platelet adhesion initiator, a platelet aggregation initiator, a blood coagulation accelerating agent, a vascular embolizing agent, a vasoconstrictor, a hemostatic agent, a wound healing agent, anti-inflammatory agent and the like.

Since the carboxylic acid-type lipid, the lipid particle and the lipid membrane can be accumulated in a site in which platelets are activated such as a vascular injury site, they can also be used as a drug carrier that carries a drug to such site. The drug included in the carboxylic acid-type lipid, the lipid particle or the lipid membrane is not particularly limited as long as it is physiologically or pharmacologically effective by being accumulated in a vascular injury site, and examples thereof include a platelet aggregation inducing drug, a vasoconstricting drug, an anti-inflammatory drug and the like.

On the other hand, it is of course possible that, using the fact that the carboxylic acid-type lipid, the lipid particle and the lipid membrane recognize a site in which platelets are accumulated to form a thrombus, the carboxylic acid-type lipid, the lipid particle and the lipid membrane are used as a carrier when a thrombolytic agent, an antiplatelet agent, an anticoagulant and the like are delivered.

We provide a platelet aggregation accelerating agent comprising the carboxylic acid-type lipid, the lipid particle or the lipid membrane.

We also provide a platelet adhesion accelerating agent comprising the carboxylic acid-type lipid, the lipid particle or the lipid membrane.

We further provide a hemostatic agent comprising the carboxylic acid-type lipid, the lipid particle or the lipid membrane.

We still further provide a platelet substitute comprising the carboxylic acid-type lipid, the lipid particle or the lipid membrane.

We yet further provide use of the carboxylic acid-type lipid, the lipid particle or the lipid membrane for acceleration of platelet adhesion and/or acceleration of platelet aggregation.

We still yet further provide use of the carboxylic acid-type lipid, the lipid particle or the lipid membrane for hemostasis.

We yet further provide use of the carboxylic acid-type lipid, the lipid particle or the lipid membrane as a platelet substitute.

We further provide use of the carboxylic acid-type lipid, the lipid particle or the lipid membrane in the production of a platelet adhesion accelerating agent and/or a platelet aggregation accelerating agent.

We still further provide use of the carboxylic acid-type lipid, the lipid particle or the lipid membrane in the production of a hemostatic agent.

We also provide use of the carboxylic acid-type lipid, the lipid particle or the lipid membrane in the production of a platelet substitute.

The platelet adhesion accelerating effect is an effect of accelerating adhesion of platelets to any site or member (e.g., a base on which the carboxylic acid-type lipid, the lipid particle or the lipid membrane is supported). In other words, the carboxylic acid-type lipid, the lipid particle or the lipid membrane can accelerate adhesion of platelets in a site or member in which the carboxylic acid-type lipid, the lipid particle or the lipid membrane exists. The platelet aggregation accelerating effect is an effect of accelerating the platelet-platelet attachment (aggregation). In other words, the carboxylic acid-type lipid, the lipid particle or the lipid membrane can accelerate the platelet-platelet attachment (aggregation) in a site or member in which the carboxylic acid-type lipid, the lipid particle or the lipid membrane exists. In actual thrombus formation, there are many instances in which adhesion and aggregation of platelets occur almost at the same time and cannot be distinguished.

The platelet aggregation accelerating agent, platelet adhesion accelerating agent, hemostatic agent and platelet substitute may be composed of the carboxylic acid-type lipid, the lipid particle or the lipid membrane alone, or may be a form of a composition comprising the carboxylic acid-type lipid, the lipid particle or the lipid membrane and other components such as a pharmaceutically acceptable carrier and additive, and are preferably a form of a composition. The composition comprising the carboxylic acid-type lipid, the lipid particle or the lipid membrane is hereinafter referred to as "composition."

The pharmaceutically acceptable carrier is not particularly limited, and examples thereof include physiological saline, a phosphate buffer, an HEPES buffer and the like.

Examples of the pharmaceutically acceptable additive is not particularly limited, and examples thereof include an isotonizing agent, a stabilizer, an antioxidant, a pH adjuster, an excipient, a diluent, a humectant, an emulsifier, a binder, a disintegrant, a lubricant, an expander, a dispersant, a suspending agent, an osmotic pressure adjuster, an antiseptic, a coloring agent, an ultraviolet absorber, a moisturizer, a thickener, a brightener, a preservative, a corrigent, a fragrance, a film forming agent, a flavoring agent, a bacterial inhibitor and the like.

The content of the carboxylic acid-type lipid, the lipid particle or the lipid membrane in the composition is not particularly limited as long as a desired effect of the carboxylic acid-type lipid, the lipid particle or the lipid membrane is exerted, and can be appropriately determined. The amount of the carboxylic acid-type lipid, the lipid particle or the lipid membrane included in the composition can be appropriately adjusted according to the application of the composition.

The dosage form of the composition is not particularly limited, and can be appropriately selected according to an administration method. Examples of the dosage form of the composition include a patch, an embrocation, a solution, an inhalant, a nebulizer, a spray, a gel, a cream, a nebula, a nasal drop, an eye drop, an injection, a pellet, a suspending agent, a powder and the like. Formulation can be performed in accordance with a known method in the field of drug production.

Examples of the patch include a patch having a base in which the composition is attached on the surface of the base. The base preferably has an adhesion layer that can adhere to the skin.

Examples of the embrocation include a gel (an aqueous gel, an oily gel), a cream, an ointment, a solution (a lotion, a liniment) and the like.

In the production of a solution or a pellet suspending agent, for example, the carboxylic acid-type lipid, the lipid particle or the lipid membrane is mixed with a physiologically acceptable aqueous solution, and, if desired, sterile filtration, dispensing, freeze-drying and the like may be performed.

The carboxylic acid-type lipid, the lipid particle or the lipid membrane can bind to activated platelets in vascular injury site or the like and can accelerate aggregation of platelets, thus enabling the acceleration of blood coagulation. Therefore, we provide a method of accelerating aggregation of platelets, which comprises administering an effective dose of the carboxylic acid-type lipid, the lipid particle or the lipid membrane to a subject in need thereof. Further preferably, we provide a hemostasis method, which comprises administering an effective dose of the carboxylic acid-type lipid, the lipid particle or the lipid membrane to a subject in need thereof. The effective dose of the carboxylic acid-type lipid, the lipid particle or the lipid membrane can be appropriately increased or decreased according to the sex, age, symptoms and the like of a subject. The subject is not particularly limited, and is preferably a mammal, and more preferably a human. The carboxylic acid-type lipid, the lipid particle or the lipid membrane may be orally administered or parenterally administered, and is usually parenterally administered. The parenteral administration method is not particularly limited as long as the carboxylic acid-type lipid, the lipid particle or the lipid membrane can be delivered to a target site, and examples thereof include application to an affected site (bleeding site), intravenous administration and the like. Examples of the other parenteral administration methods include intraarterial administration, intramuscular administration, subcutaneous administration, intraperitoneal administration, transmucosal administration, transdermal administration and the like.

EXAMPLES

Our lipids, particles, membranes, compositions and methods will be described in more detail by way of Examples.
Synthesis of Lipid
The following lipids were synthesized and used in the Examples.
(1) Synthesis of Carboxylic Acid-Type Lipid Represented by Formula (a2) (DHSG: 1,5-Dihexadecyl-N-Succinyl-L-Glutamate)

In accordance with the following procedures, DHSG was synthesized. DHSG is used as a starting material when our carboxylic acid-type lipids (Glu-DHSG, Asp-DHSG and AG-DHSG) are synthesized.

Glutamic acid (2.96 g, 20 mmol), p-toluenesulfonic acid (4.56 g, 24 mmol) and hexadecyl alcohol (10.65 g, 44 mmol) were dissolved in benzene (150 mL) and mixed, and the mixture was refluxed at 100° C. for 14 hours while dehydrating. Then, the solvent was removed under reduced pressure, and the residue thus obtained was redissolved in chloroform, washed with a saturated aqueous solution of sodium hydrogen carbonate three times, and further washed with water three times. Then, the chloroform layer was dehydrated using sodium sulfate, and after filtration, the solvent of the obtained solution was removed under reduced pressure. The residue thus obtained was dissolved in methanol (400 mL) at 60° C., and after the obtained solution was cooled to 4° C. and recrystallized, the crystal was filtered and dried to obtain a glutamic acid derivative represented by formula (a1) (Glu2C16) as a white solid (9.5 g, yield of 80%).

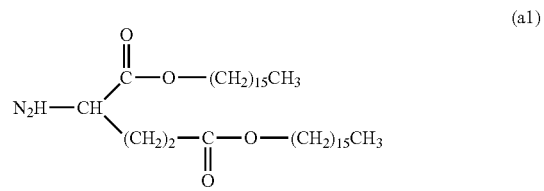

(a1)

The obtained Glu2C16 (1.49 g, 2.5 mmol) was dissolved in a mixed solution (mixing ratio of 1:1 (v/v)) of chloroform (7.5 mL) and THF (7.5 mL) and mixed in a recovery flask with a volume of 50 mL, and anhydrous succinic acid (0.374 g, 3.74 mmol) was added to the mixture, followed by stirring at 23° C. for 12 hours to obtain a reaction solution. The solvent of the obtained reaction solution was removed under reduced pressure, and after the residue was dissolved in a mixed solution (mixing ratio of 1:5 (v/v)) of ethanol and acetone, and the solution thus obtained was cooled at 4° C. for 3 hours and recrystallized. The crystal thus obtained was filtered through a glass filter (G4), and the filtered product was dissolved in chloroform. After the solvent of the obtained solution was removed under reduced pressure, the residue was redissolved in tert-butyl alcohol, and the solution thus obtained was freeze-dried to obtain DHSG represented by formula (a2) as a white powder (1376 mg, 1.98 mmol, yield of 79%).

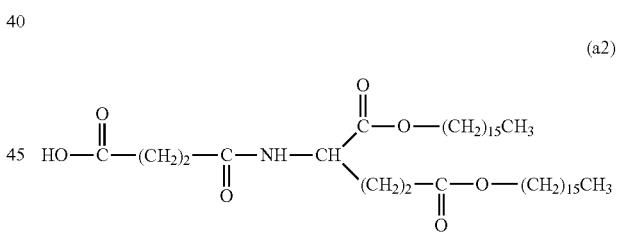

(a2)

(2) Synthesis of Carboxylic Acid-Type Lipid Represented by Formula (b2) (Asp-DHSG)

In accordance with the following procedures, an aspartic acid residue was introduced into the hydrophilic moiety (carboxyl group) of DHSG to synthesize a carboxylic acid-type lipid of the example (Asp-DHSG).

In a recovery flask with a volume of 50 mL, DHSG (197 mg, 0.28 mmol), Asp(—OtBu)(—OtBu)·HCl (L-aspartic acid di-tert-butyl ester hydrochloride) (120 mg, 0.42 mmol), PyBOP (1H-benzotriazol-1-yloxytris[pyrrolidin-1-yl]phosphonium hexafluorophosphate) (177 mg, 0.34 mmol) and triethylamine (TEA) (57.4 µL, 0.42 mmol) were dissolved in dichloromethane (4 mL), followed by stirring at 23° C. for 24 hours to obtain a reaction solution. The reaction solution thus obtained was separated twice using dichloromethane and a saturated aqueous solution of sodium carbonate, and further separated twice using dichloromethane and a saturated aqueous solution of sodium chloride, thus removing water-soluble impurities and acidic impurities to obtain a crude product. After the crude product was dehydrated using sodium sulfate, the product was purified by silica gel column chromatography (developing solvent: hexane/ethyl acetate=1/1). The purified product thus obtained was redissolved in tert-butyl alcohol, and the solution thus obtained was freeze-dried to obtain Asp(—OtBu)(—OtBu)-DHSG represented by formula (b1) as a white powder (160 mg, 0.17 mmol, yield of 61.8%).

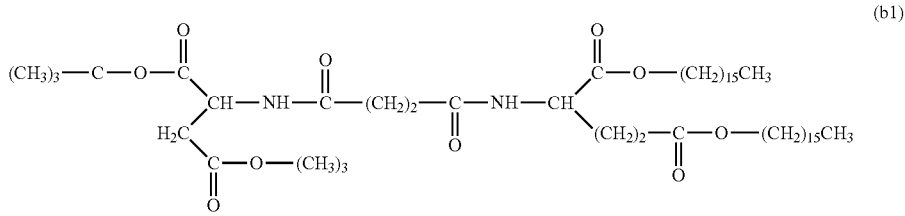

(b1)

The obtained Asp(—OtBu)(—OtBu)-DHSG (40 mg, 0.044 mmol) was dissolved in a mixture of trifluoroacetic acid (4 mL) and dichloromethane (2 mL) in a recovery flask with a volume of 50 mL, followed by stirring at 23° C. for 3 hours, and the reaction solution thus obtained was filtered under reduced pressure using an acid-proof pump. The filtered product was redissolved in tert-butyl alcohol, and the solution thus obtained was freeze-dried to obtain Asp-DHSG represented by formula (b2) as a white powder (32 mg, 0.040 mmol, yield of 92.4%).

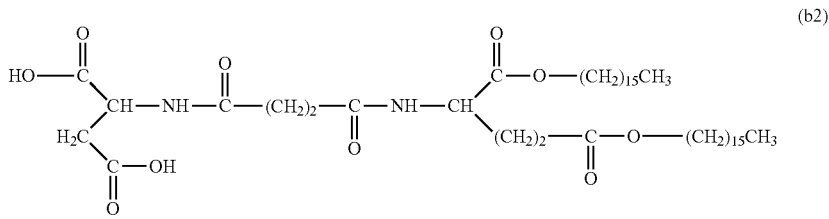

(b2)

(3) Synthesis of Carboxylic Acid-Type Lipid Represented by Formula (c2) (Glu-DHSG)

In accordance with the following procedures, a glutamic acid residue was introduced into the hydrophilic moiety (carboxyl group) of DHSG to synthesize a carboxylic acid-type lipid of the example (Glu-DHSG).

In a recovery flask with a volume of 50 mL, DHSG (197 mg, 0.28 mmol), Glu(—OtBu)(—OtBu)·HCl (L-glutamic acid di-tert-butyl ester hydrochloride) (127 mg, 0.43 mmol), PyBOP (182 mg, 0.35 mmol) and TEA (58.8 μL, 0.43 mmol) were dissolved in dichloromethane (4 mL), followed by stirring at 23° C. for 24 hours to obtain a reaction solution.

The reaction solution thus obtained was separated twice using dichloromethane and a saturated aqueous solution of sodium carbonate, and further separated twice using dichloromethane and a saturated aqueous solution of sodium chloride, thus removing water-soluble impurities and acidic impurities to obtain a crude product. After the crude product was dehydrated using sodium sulfate, the product was purified by silica gel column chromatography (developing solvent: hexane/ethyl acetate=1/1). The purified product thus obtained was redissolved in tert-butyl alcohol, and the solution thus obtained was freeze-dried to obtain Glu(—OtBu)(—OtBu)-DHSG represented by formula (c1) as a white powder (216.4 mg, 0.23 mmol, yield of 79.8%).

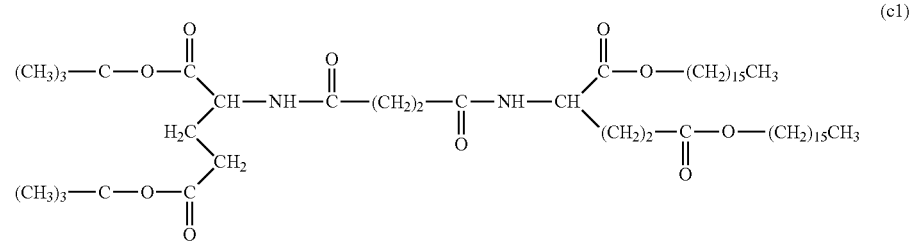

(c1)

The obtained Glu(—OtBu)(—OtBu)-DHSG (40 mg, 0.043 mmol) was dissolved in a mixture of trifluoroacetic acid (4 mL) and dichloromethane (2 mL) in a recovery flask with a volume of 50 mL, followed by stirring at 23° C. for 3 hours, and the reaction solution thus obtained was filtered under reduced pressure using an acid-proof pump. The filtered product was redissolved in tert-butyl alcohol, and the solution thus obtained was freeze-dried to obtain Glu-DHSG represented by formula (c2) as a white powder (35 mg, 0.042 mmol, yield of 87.6%).

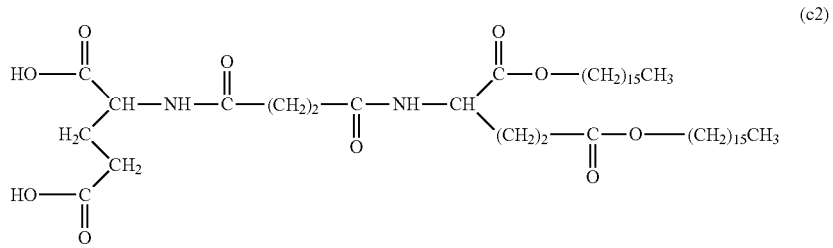

(c2)

(4) Synthesis of Carboxylic Acid-Type Lipid Represented by Formula (d2) (AG-DHSG)

In accordance with the following procedures, a peptide residue (AG residue) composed of two aspartic acid residues and one glutamic acid residue was introduced into the hydrophilic moiety (carboxyl group) of DHSG to synthesize a carboxylic acid-type lipid of the example (AG-DHSG).

In a recovery flask with a volume of 50 mL, Glu-DHSG (57.4 mg, 0.069 mmol), Asp(—OtBu)(—OtBu)·HCl (58.9 mg, 0.209 mmol), PyBOP (86.9 mg, 0.167 mmol) and TEA (30 μL, 0.209 mmol) were dissolved in dichloromethane (4 mL), followed by stirring at 23° C. for 72 hours to obtain a reaction solution. The reaction solution thus obtained was separated twice using dichloromethane and a saturated aqueous solution of sodium carbonate, and further separated twice using dichloromethane and a saturated aqueous solution of sodium chloride, thus removing water-soluble impurities and acidic impurities to obtain a crude product. After the crude product was dehydrated using sodium sulfate, the product was purified by silica gel column chromatography (developing solvent: hexane/ethyl acetate=1/2). The purified product thus obtained was redissolved in tert-butyl alcohol, and the solution thus obtained was freeze-dried to obtain Asp(—OtBu)(—OtBu)-Glu-DHSG represented by formula (d1) as a white powder (38.9 mg, 0.03 mmol, yield of 44.0%).

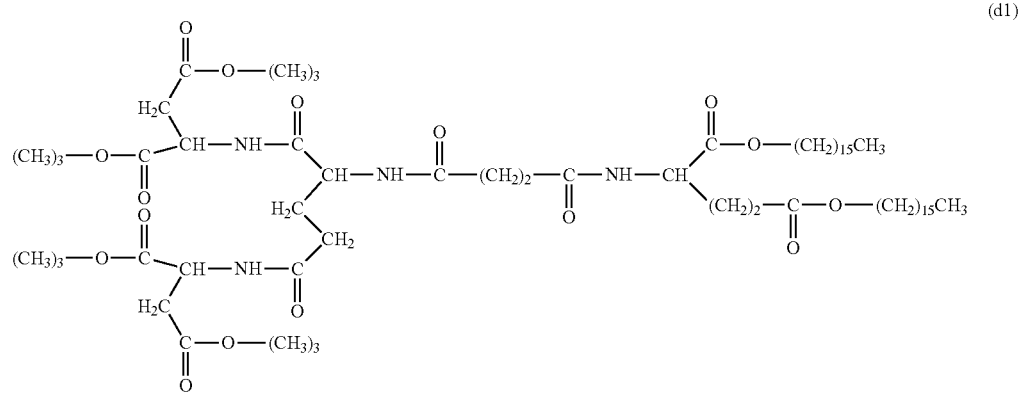

(d1)

The obtained Asp(—OtBu)(—OtBu)-Glu-DHSG (35 mg, 0.027 mmol) was dissolved in a mixture of trifluoroacetic acid (4 mL) and dichloromethane (2 mL) in a recovery flask with a volume of 50 mL, followed by stirring at 23° C. for 3 hours, and the reaction solution thus obtained was filtered under reduced pressure using an acid-proof pump. The filtered product was redissolved in tert-butyl alcohol, and the solution thus obtained was freeze-dried to obtain AG-DHSG represented by formula (d2) as a white powder (23 mg, 0.021 mmol, yield of 80.0%).

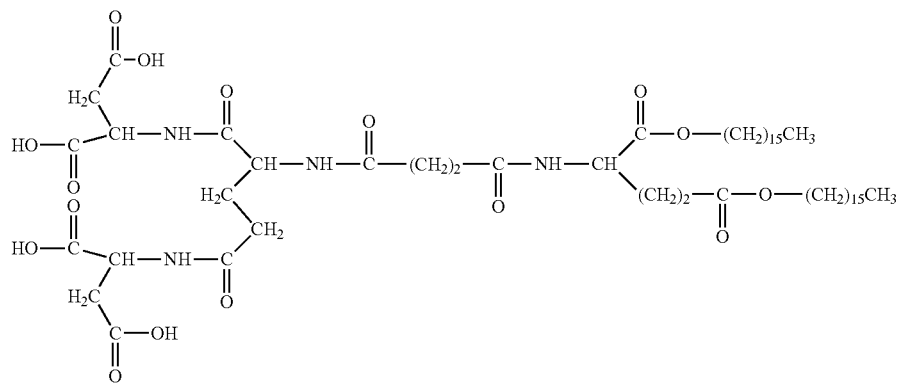

(d2)

(5) Synthesis of Carboxylic Acid-Type Lipid Represented by Formula (e2)

In accordance with the following procedures, a carboxylic acid-type lipid of the reference example represented by formula (e2) was synthesized. This carboxylic acid-type lipid can be used as a starting material when our carboxylic acid-type lipid is synthesized. In other words, by introducing an amino acid residue such as aspartic acid residue and a glutamic acid residue, and a peptide residue such as an AG residue, into the hydrophilic moiety (carboxyl group) of this carboxylic acid-type lipid in the same manner as mentioned above, our carboxylic acid-type lipid can be synthesized.

L-glutamic acid (1.47 g, 10 mmol) and t-butoxycarbonyl anhydride (2.62 g, 12 mmol) were dissolved in a mixed solution of dioxane (20 mL), water (10 mL) and iN NaOH (10 mL), followed by stirring at 25° C. for 6 hours to obtain a reaction solution. The obtained reaction solution was concentrated under reduced pressure to 10 mL, and after an aqueous 5% potassium hydrogen sulfate solution was added until pH became 2.4, the solution was washed with ethyl acetate three times, and further washed with water three times. After the ethyl acetate layer was dehydrated with sodium sulfate, the solvent was removed under reduced pressure, the residue was dissolved in hexane, and the solution thus obtained was cooled at 4° C. and recrystallized. The crystal thus obtained was filtered, and the filtered product was dried to obtain a branched compound 1 in which the amino group is protected by a protecting group (t-butoxycarbonyl group (Boc group)) as a white solid (1.85 g, yield of 75%).

The obtained branched compound 1 (0.49 g, 2 mmol) and N,N'-dicyclohexylcarbodiimide (DCC) (0.82 g, 4 mmol) were dissolved in chloroform, followed by stirring at 4° C. for 1 hour to obtain a mixture. The obtained mixture was added dropwise to a chloroform solution in which a glutamic acid derivative (Glu2C16) (2.98 g, 5 mmol) and triethylamine (0.20 g, 2 mmol) were dissolved to obtain a reaction solution. The obtained reaction solution was stirred at 25° C. for 6 hours, followed by filtration through a glass filter (G4), and the filtrate was concentrated under reduced pressure, and reprecipitated using methanol and purified. After the precipitate was filtered, the filtered product was purified by silica gel column chromatography (developing solvent: chloroform/methanol=6/1 (v/v)) to obtain a branched compound 2 (1.40 g, yield of 50%).

The obtained branched compound 2 (1.40 g, 1 mmol) was dissolved in trifluoroacetic acid (TFA), followed by stirring for 1 hour to remove the protecting group (Boc group). The solution thus obtained was dissolved in methanol, followed by cooling at 4° C. and recrystallization. The crystal thus obtained was filtered, and the filtered product was dried to obtain a branched compound 3 represented by formula (e1) (1.17 g, yield of 90%).

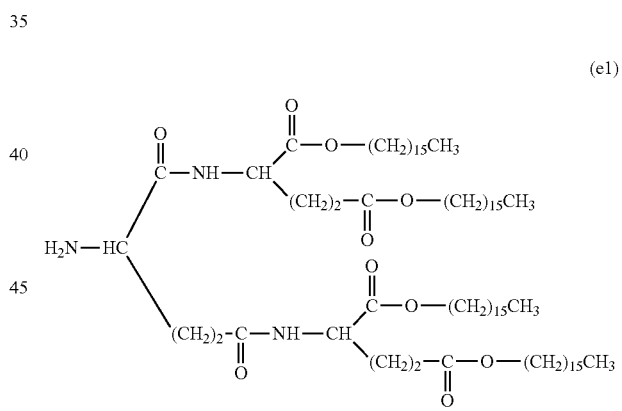

(e1)

The obtained branched compound 3 (1.17 g, 0.9 mmol) was dissolved in a mixed solution (mixing ratio of 1:1 (v/v)) of chloroform and tetrahydrofuran and mixed, and anhydrous succinic acid (130 g, 1.35 mmol) was added to the mixture, followed by stirring for 5 hours to obtain a reaction solution. The solvent of the obtained reaction solution was removed under reduced pressure, and after the residue was dissolved in a mixed solution (mixing ratio of 1:5 (v/v)) of ethanol and acetone, and the solution thus obtained was cooled at 4° C. and recrystallized. The crystal thus obtained was filtered, and the filtered product was dried to obtain a carboxylic acid-type lipid represented by formula (e2) (reference example) as a white solid (0.95 g, yield of 75%).

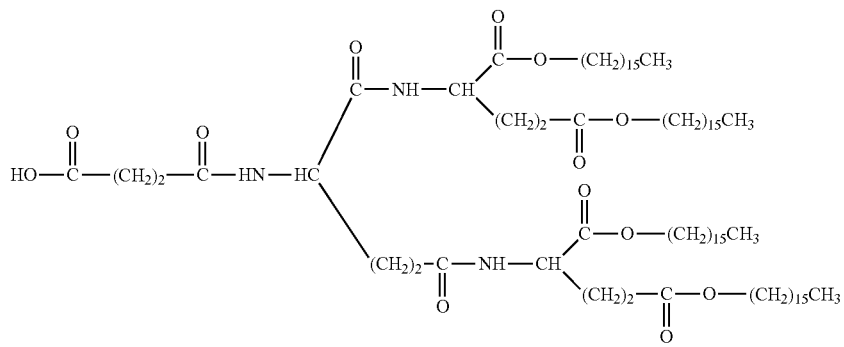

(e2)

Examples 1 to 5 and Comparative Example 1

(1) Preparation of Liposome

In accordance with the following procedures, a liposome was prepared. In this example, together with the carboxylic acid-type lipid obtained by the synthesis method mentioned above, the following lipids (commercially available products) were used. Cholesterol is hereinafter sometimes expressed as "Chol."

DPPC (1,2-dipalmitoyl-sn-glycero-3-phosphatidylcholine, manufactured by NIPPON FINE CHEMICAL CO., LTD.)

Cholesterol (manufactured by NIPPON FINE CHEMICAL CO., LTD.)

PEG-DSPE (1,2-distearoyl-sn-glycero-3-phosphatidyletha-nolamine-N-[monomethoxypoly(ethyleneglycol)], manufactured by NOF CORPORATION)

The lipids were mixed in the molar ratio shown in Table 1 to obtain a lipid mixture. The obtained lipid mixture was dissolved in tert-butyl alcohol, and the solution thus obtained was freeze-dried for 12 hours to obtain a lipid powder. In Examples 1 to 3 and Comparative Example 1, the obtained lipid powder was hydrated using DPBS (Dulbecco's PBS, 3 wt %) at 25° C. for 12 hours, and the particle diameter of the liposome was controlled by the extrusion method (pore diameter of 450 nm×2, pore diameter of 220 nm×2, pore diameter of 200 nm×1) to obtain a liposome dispersion liquid. In Examples 4 and 5, the obtained lipid powder was sonicated using an HEPES buffer (20 mM) at 50° C. for 1 hour to obtain a liposome dispersion liquid.

In Example 1, using DPPC, cholesterol, Asp-DHSG and PEG-DSPE (DPPC:cholesterol:Asp-DHSG:PEG-DSPE=5: 5:5:0.045 (molar ratio)), a liposome of the example (L555Asp-DHSG) was obtained. In Example 2, using DPPC, cholesterol, Glu-DHSG and PEG-DSPE (DPPC: cholesterol:Glu-DHSG:PEG-DSPE=5:5:5:0.045 (molar ratio)), a liposome of the example (L555Glu-DHSG) was obtained. In Example 3, using DPPC, cholesterol, AG-DHSG and PEG-DSPE (DPPC cholesterol:AG-DHSG: PEG-DSPE=5:5:5:0.045 (molar ratio)), a liposome of the example (L555AG-DHSG) was obtained. In Example 4, using cholesterol and Asp-DHSG (cholesterol:Asp-DHSG=5:5 (molar ratio)), a liposome of the example (L055 (Asp)) was obtained. In Example 5, using cholesterol and AG-DHSG (DPPC:cholesterol:AG-DHSG=5:10 (molar ratio)), a liposome of the example (L05[10](AG)) was obtained. In Comparative Example 1, using DPPC, cholesterol and PEG-DSPE (DPPC:cholesterol:PEG-DSPE=5:5:5: 0.045 (molar ratio)), a liposome of the comparative example not including a carboxylic acid-type lipid (L555DHSG) was obtained.

TABLE 1

| | DPPC | Chol | DHSG | Glu-DHSG | Asp-DHSG | AG-DHSG | DPPG | DPPS | PEG-DSPE |
|---|---|---|---|---|---|---|---|---|---|
| Example 1 (L555Asp-DHSG) | 5 | 5 | 0 | 0 | 5 | 0 | 0 | 0 | 0.045 |
| Example 2 (L555Glu-DHSG) | 5 | 5 | 0 | 5 | 0 | 0 | 0 | 0 | 0.045 |
| Example 3 (L555AG-DHSG) | 5 | 5 | 0 | 0 | 0 | 5 | 0 | 0 | 0.045 |
| Example 4 (L055(Asp)) | 0 | 5 | 0 | 0 | 5 | 0 | 0 | 0 | 0 |
| Example 5 (L05[10](AG)) | 0 | 5 | 0 | 0 | 0 | 10 | 0 | 0 | 0 |
| Comparative Example 1 (L555DHSG) | 5 | 5 | 5 | 0 | 0 | 0 | 0 | 0 | 0.045 |

(2) Measurement of Mean Particle Diameter of Liposome

In accordance with the following procedures, the mean particle diameter of a liposome was measured.

1 mL of a 0.1 mg/mL liposome dispersion liquid filtered through a 0.2 μm filter was put in a disposable cell in which dust and the like was removed by an air duster, and using Zetasizer nano (manufactured by Malvern Panalytical Ltd.), the mean particle diameter was measured (25° C., n=3). The mean particle diameter of a liposome is shown in Table 2.

(3) Measurement of Zeta Potential of Liposome

In accordance with the following procedures, the zeta potential of a liposome was measured.

In cells for zeta potential measurement (folded capillary cells) (DTS1061, manufactured by Malvern Panalytical Ltd.), 1 mL of a 0.1 mg/mL liposome dispersion liquid was put using a 2.5 mL syringe, and after bubbles in the cells were removed, using Zetasizer nano (manufactured by Malvern Panalytical Ltd.), the zeta potential was measured at pH 7.4 and 25° C. (n=3). The mean zeta potential of a liposome is shown in Table 2.

TABLE 2

|  | Particle diameter (nm) | Zeta potential (mV) |
|---|---|---|
| Example 1 (L555Asp-DHSG) | 247 ± 97 | −22.0 ± 0.2 |
| Example 2 (L555Glu-DHSG) | 261 ± 115 | −20.2 ± 1.0 |
| Example 3 (L555AG-DHSG) | 219 ± 86 | −35.9 ± 0.2 |
| Example 4 (L055(Asp)) | 316 ± 262 | −75.8 ± 2.9 |
| Example 5 (L05[10](AG)) | 211 ± 133 | −79.6 ± 8.5 |
| Comparative Example 1 (L555DHSG) | 226 ± 80 | −18.9 ± 1.3 |

(4) Evaluation of Activated Platelet Aggregation Capacity

In accordance with the following procedures, a platelet sample used for evaluation of the activated platelet aggregation capacity was prepared.

Using a 18 G winged needle and a 20 mL syringe, about 15 mL of blood was collected from a guinea pig (Hartley, male, 8 weeks old, body weight of 450 g, manufactured by Japan SLC, Inc.) by cardiopuncture, and was divided into two equal parts, which were contained in two 14 mL tubes, respectively. Then, 3.8% sodium citrate was added and mixed so that the volume thereof was 1/10 of the volume of whole blood, followed by slowly stirring twice using a polyethylene dropper to obtain a mixture. Then, the obtained mixture was centrifuged (600 rpm, room temperature, 15 minutes) to recover the platelet-rich plasma (PRP) of the supernatant. Then, the blood after recovery of PRP was centrifuged again (2000 rpm, room temperature, 10 minutes) to recover the platelet-poor plasma (PPP) of the supernatant. Using an automated hematology analyzer, the platelet count of the recovered PRP and PPP was measured, and PRP, PPP and an HEPES-Tyrode buffer were mixed so that the platelet concentration was $2.0 \times 10^5/\mu L$ to obtain a platelet sample.

Using the obtained platelet sample and a liposome dispersion liquid, observation and fluorescence quantitative determination of a fluorescently labeled liposome in a platelet aggregate were performed in accordance with the following procedures.

Figure 2:
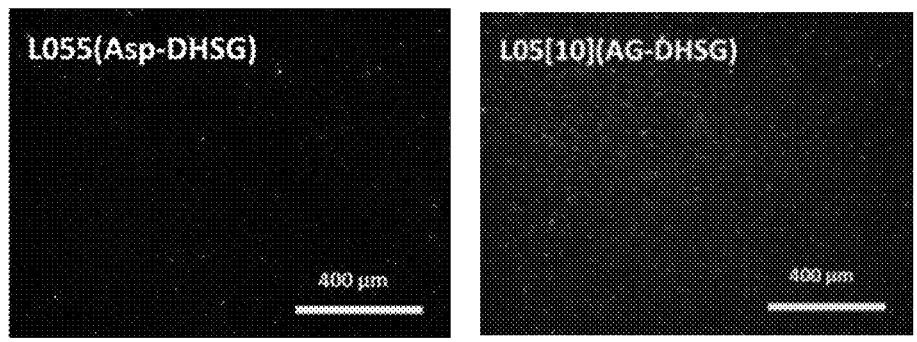
FIG. 2 shows observation results of fluorescently labeled liposomes in platelet aggregates (fluorescence micrographs of platelet aggregates obtained by using a DiD-labeled liposome dispersion liquid).

In a 96-well glass bottom plate, 50 μL of a guinea pig-derived platelet sample (platelet concentration: $2.0 \times 10^5/\mu L$) prepared by the abovementioned method and a liposome dispersion liquid (200 μM, 5 μL) containing a liposome labeled with a fluorescence substance DiO (3,3'-dioctadecyloxacarbocyanine perchlorate) or DiD (1,1'-dioctadecyl-3,3,3',3'-tetramethylindodicarbocyanine perchlorate) were mixed, followed by allowing to stand at room temperature for 2 minutes. If necessary, ADP (1 μM, 5 μL) that activates platelets was added, followed by allowing to stand at room temperature for 4 minutes, and then, using 8% formalin (60 L, final concentration of 4%), the mixture was fixed at room temperature for 30 minutes, and after completion of fixation, the fixed mixture was washed with an HEPES-Tyrode buffer (100 L) three times to obtain a platelet aggregate. The results of observation (fluorescence micrographs) of the platelet aggregate obtained by using the liposome dispersion liquid are shown in FIGS. 1 and 2. In Example 1 (L555Asp-DHSG), using a liposome dispersion liquid containing a liposome labeled with DiO, a platelet aggregate was obtained (top of FIG. 1). In Example 2 (L555Glu-DHSG), Example 3 (L555AG-DHSG), Example 4 (L055(Asp)) and Example 5 (L05[10](AG)), using a liposome dispersion liquid containing a liposome labeled with DiD, a platelet aggregate was obtained (bottom of FIG. 1 and FIG. 2). In Comparative Example 1 (L555DHSG), two liposome dispersion liquids labeled with DiO or DiD were provided, and using each liposome dispersion liquid, a platelet aggregate was obtained (top and bottom of FIG. 1). Using a fluorescence microscope (20-fold or 60-fold), the fluorescently labeled liposome in the obtained platelet aggregate was observed. Using ImageJ, the fluorescence intensity of the fluorescently labeled liposome in each of platelet aggregates shown in FIGS. 1 and 2 was measured. The results of measurement of the fluorescence intensity are shown in Table 3. The value of the fluorescence intensity in Table 3 is a relative value when the fluorescence intensity when using Comparative Example 1 (L555DHSG) is regarded as 1.

TABLE 3

|  | Fluorescence intensity (mean ± standard deviation) (relative value when the value of Comparative Example 1 is regarded as 1) |
|---|---|
| Example 1 (L555Asp-DHSG) (n = 15) | 2.11 ± 0.63** |
| Example 2 (L555Glu-DHSG) (n = 15) | 1.81 ± 0.31** |
| Example 3 (L555AG-DHSG) (n = 15) | 2.95 ± 0.60** |
| Example 4 (L055(Asp)) (n = 1) | 1.48 ± 0.06 [a] |
| Example 5 (L05[10](AG)) (n = 1) | 19.91 ± 2.54 [a] |

**represents the fact that the fluorescence intensity is statistically significantly higher than that of Comparative Example 1 (L555DHSG) (P < 0.01, t-test).
[a] represents the mean ± standard deviation when one sample was measured three times.

As shown in Table 3, the liposomes of Examples 1 to 5 had higher fluorescence intensity in the platelet aggregate than that of the liposome of Comparative Example 1. This represents the fact that the liposomes of Examples 1 to 5 have superior platelet aggregation accelerating capacity to that of the liposome of Comparative Example 1. Particularly, the liposome of Example 1 had significantly higher fluorescence intensity in the platelet aggregate than that of the liposome of Comparative Example 1. This represents the fact that the liposome of Example 1 has significantly superior platelet aggregation accelerating capacity to that of the liposome of Comparative Example 1.

(5) Fabrication of Hemostatic Material and Evaluation of Hemostatic Capacity of the Hemostatic Material In accordance with the following procedures, a hemostatic material was fabricated using a liposome, and the hemostatic capacity of the hemostatic material was evaluated.

Fabrication of Base

A base for supporting a liposome was fabricated in accordance with the following procedures.

A thermoplastic resin composition including 80% by mass of a poly-L-lactic acid resin (PLLA resin, weight average molecular weight (Mw): 80,000, melting point (Tm): 169° C., melt flow rate (MFR): 78 g/10 minutes) vacuum-dried at 80° C. for 24 hours and 20% by mass of polyethylene glycol (manufactured by Wako Pure Chemical Industries, Ltd., weight average molecular weight (Mw): 6,000) was supplied to an electrically grounded extruder, melt-kneaded at a spinning temperature of 300° C., and extruded from a spinning nozzle. At this time, assist air at 380° C. was blown toward the resin fluid ejected from the spinning nozzle, and a voltage of 10 kV was applied by an electrode independent from the side of the nozzle, followed by blowing a molten product of the thermoplastic resin composition mentioned above on a cellulose sponge (manufactured by Toray Fine Chemicals Co., Ltd., thickness of 0.5 mm) for 10 seconds, thus obtaining a base having the cellulose sponge and a fiber sheet formed on the cellulose sponge. Fabrication of Hemostatic Material The base complex fabricated in accordance with the abovementioned procedures was die-cut with a metal punch to obtain a cylindrical base complex with a diameter of 13 mm. On the base part (fiber sheet part) of the obtained cylindrical base complex, 66.7 µL each of the tert-butyl alcohol solutions with a concentration 30 mg/mL of Examples 1 to 4 and 7 to 8 was sprayed, followed by freeze-drying at −40° C. for 12 hours, thus fabricating a hemostatic material. The hemostatic materials fabricated using the tert-butyl alcohol solutions of Examples 1 to 4 and 7 to 8 are hereinafter referred to as hemostatic materials A1 to A4, A7 and A8 of the example, respectively. A hemostatic material fabricated in the same manner as mentioned above except that 66.7 µL of tert-butyl alcohol is sprayed in place of the tert-butyl alcohol solution is referred to as control hemostatic material.

Evaluation of Hemostatic Capacity

A guinea pig (Slc:Hartley, 8 weeks old, male, manufactured by Japan SLC, Inc.) under 3% isoflurane anesthesia was fixed in a supine position, and the abdominal wall was incised at the midline to expose the left lobe of liver. A part of the incised marginal region was removed with scissors so that the width of the section was 10 mm, thus making bleeding from the entire wound surface. A hemostatic material was attached to cover the wound surface, and astriction was performed with fingers. The hemostatic material was detached every 2 minutes, and the condition of an issue of blood from the wound surface was confirmed. When an issue of blood was observed within 5 seconds after detachment, the detached hemostatic material was attached to the wound surface again. At the time point at which no issue of blood was observed during 5 seconds after detachment, hemostasis was regarded as successful, and the time from attachment of the hemostatic material to hemostasis (hemostasis time) was measured. A nonwoven fabric was laid around the liver before removal of the liver to absorb blood issued during hemostasis, and the amount of bleeding was calculated from the difference in weight of the hemostatic material and the nonwoven fabric that absorbed blood between before and after surgery. The hemostasis time (min) is shown in Table 4, and the amount of bleeding (mg) is shown in Table 5. Hemostasis was performed three times for each of hemostatic materials, and the mean of the hemostasis time and the amount of bleeding for three times was regarded as the hemostasis time and the amount of bleeding of each hemostatic material.

TABLE 4

|  | Hemostasis time (min) (mean ± standard deviation) |
|---|---|
| Control hemostatic material (Dulbecco's PBS) | 10.7 ± 0.94 |
| Hemostatic material of the example (L555Asp-DHSG) | 7.3 ± 0.94 |
| Hemostatic material of the comparative example (L555DHSG) | 8.0 |

As shown in Table 4, when the hemostatic material of the example was used, the hemostasis time was significantly shortened compared to when the control hemostatic material was used ($p<0.01$, t-test). This represents the fact that the hemostatic material of the example has superior hemostatic capacity to that of the control hemostatic material.

TABLE 5

|  | Amount of bleeding (mg) (mean ± standard deviation) |
|---|---|
| Control hemostatic material (Dulbecco's PBS) | 196.16 ± 54.45 |
| Hemostatic material of the example (L555Asp-DHSG) | 100.93 ± 25.18 |
| Hemostatic material of the comparative example (L555DHSG) | 137.21 ± 31.36 |

As shown in Table 5, when the hemostatic material of the example was used, the amount of bleeding was significantly suppressed compared to when the control hemostatic material was used ($p<0.05$, t-test). On the other hand, when the hemostatic material of the comparative example was used, there was no significant difference in the amount of bleeding compared to when the control hemostatic material was used. This represents the fact that the hemostatic material of the example has superior hemostatic capacity to that of the control hemostatic material and of the hemostatic material of the comparative example.

Examples 6 to 9

(1) Synthesis of Lipid

DHSG was synthesized in the same manner as mentioned above, and using the synthesized DHSG, Asp-DHSG, Glu-DHSG and AG-DHSG were synthesized in the same manner as mentioned above.

(2) Fabrication of Hemostatic Material

DHSG, Asp-DHSG, Glu-DHSG and AG-DHSG were fabricated in the same manner as mentioned above. In the same manner as mentioned above, a base complex having a cellulose sponge and a fiber sheet made of a poly-L-lactic acid resin formed on the cellulose sponge was fabricated, and the fabricated base complex was die-cut with a metal punch to obtain a cylindrical base complex with a diameter of 13 mm. On the base part (fiber sheet part) of the obtained cylindrical base complex, 66.7 µL each of tert-butyl alcohol solutions with a concentration 30 mg/mL of DHSG, Asp-DHSG, Glu-DHSG and AG-DHSG was sprayed, followed by drying, thus fabricating a hemostatic material. In Example 6, using a tert-butyl alcohol solution of DHSG, a hemostatic material (hereinafter referred to as "hemostatic material D1") was fabricated; in Example 7, using a tert-butyl alcohol solution of Asp-DHSG, a hemostatic material (hereinafter referred to as "hemostatic material D2") was fabricated; in Example 8, using a tert-butyl alcohol solution of Glu-DHSG, a hemostatic material (hereinafter referred to as "hemostatic material D3") was fabricated; and in Example 9, using a tert-butyl alcohol solution of AG-DHSG, a hemostatic material (hereinafter referred to as "hemostatic material D4") was fabricated.

(3) Evaluation of Platelet Aggregation Capacity of Hemostatic Material (In Vitro)

Figure 3:
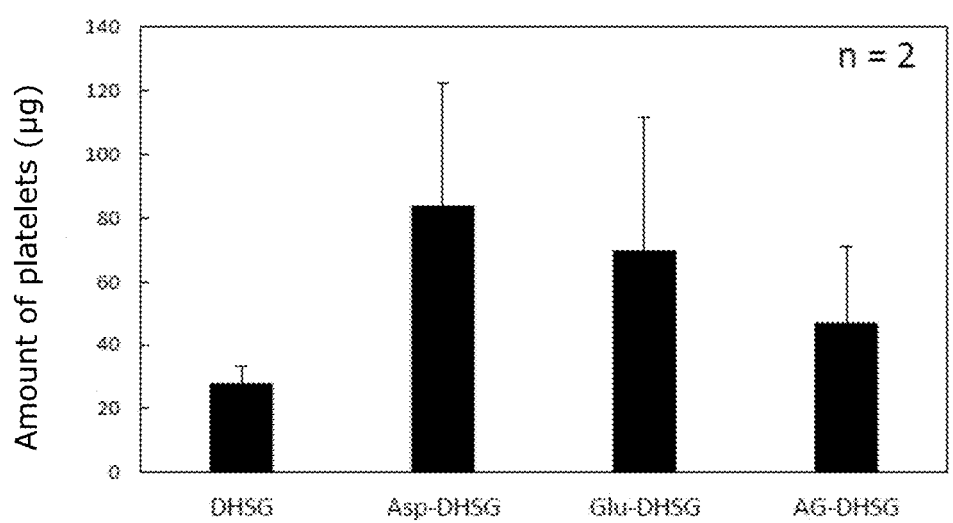
FIG. 3 shows results on evaluation of the platelet aggregation capacity of a hemostatic material (in vitro).
Figure 4:
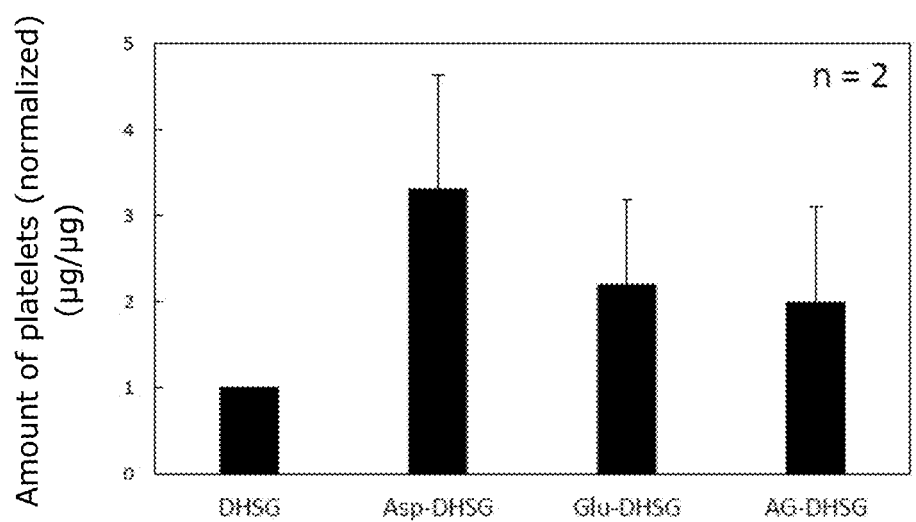
FIG. 4 shows results on evaluation of the platelet aggregation capacity of a hemostatic material (in vitro).

From the hemostatic materials D1, D2, D3 and D4, a base part (fiber sheet part) supporting DHSG, Asp-DHSG, Glu-DHSG and AG-DHSG, respectively, was taken out. To a 12-well plate, the base part (fiber sheet part) that was taken out and 1 mL of guinea pig-derived PRP ($2.0 \times 10^5/\mu L$) prepared by the abovementioned method were added. Thereafter, ADP (1 M, 100 μL) that activates platelets was added, and after allowing to stand at room temperature for 5 minutes, the mixture was washed with 1 mL of DPBS twice. Thereafter, to dissolve platelets attached to the base part (fiber sheet part), 500 μL of 0.5% Triton X was added, followed by allowing to stand at room temperature for 1 hour to obtain a platelet lysate. To a 96-well plate, L of the platelet lysate prepared by the abovementioned method and 150 μL of PIERCE (trademark) 660 nm Protein Assay Kit were added, followed by allowing to stand for 5 minutes. By measuring absorbance at 660 nm using a microplate reader, proteins were quantitatively determined, and the determination results were used as an index of the count of platelets which were not washed away and were attached to the fiber sheet. The results are shown in FIGS. 3 and 4. The results in FIG. 4 are relative values when the platelet count in using the hemostatic material D1 is regarded as 1. In FIGS. 3 and 4, "DHSG" represents results on the hemostatic material D1, "Asp-DHSG" represents results on the hemostatic material D2, "Glu-DHSG" represents results on the hemostatic material D3, and "AG-DHSG" represents results on the hemostatic material D4.

As shown in FIGS. 3 and 4, it was shown that each of the hemostatic material D2 supporting Asp-DHSG, the hemostatic material D3 supporting Glu-DHSG, and the hemostatic material D4 supporting AG-DHSG has a higher count of tightly attached platelets than that of the hemostatic material D1 supporting DHSG.

In both instances when guinea pig-derived PRP was added to the base part (fiber sheet part) before supporting a lipid and when guinea pig-derived PRP was not added to the base part (fiber sheet part) before supporting a lipid, no proteins were detected, and as a result of washing, no platelets were detected. When DPPC in place of DHSG, Asp-DHSG, Glu-DHSG and AG-DHSG was supported on the base part (fiber sheet part), as a result of washing, no platelets were detected. This is considered to be due to the fact that DPPC does not show a negative charge in vivo.

(4) In Vivo Hemostasis Study using Guinea Pigs

In the same manner as mentioned above, an in vivo hemostasis study using guinea pigs was performed, and by quantitatively determining the hemostasis time and the amount of bleeding, the hemostatic capacity of the hemostatic materials D2, D3 and D4 were evaluated. As a control, the hemostasis time and the amount of bleeding of a base complex before supporting a lipid were also quantitatively determined. The results are shown in Tables 6 and 7. As shown in Tables 6 and 7, the hemostasis time of the hemostatic materials D2, D3 and D4 was significantly shorter than the hemostasis time of the base complex before supporting a lipid, and the amount of bleeding of the hemostatic materials D2, D3 and D4 was lower than the amount of bleeding of the base complex before supporting a lipid.

TABLE 6

| Hemostasis time (min) | Base complex before supporting a lipid | Hemostatic material D2 (Asp-DHSG) | Hemostatic material D3 (Glu-DHSG) | Hemostatic material D4 (AG-DHSG) |
| --- | --- | --- | --- | --- |
| Mean | 10.7 | 6.8 | 6.0 | 4.8 |
| SD | 0.9 | 2.7 | 2.2 | 1.0 |

TABLE 7

| Amount of bleeding (mg) | Base complex before supporting a lipid | Hemostatic material D2 (Asp-DHSG) | Hemostatic material D3 (Glu-DHSG) | Hemostatic material D4 (AG-DHSG) |
| --- | --- | --- | --- | --- |
| Mean | 196.2 | 92.7 | 63.7 | 39.3 |
| SD | 54.5 | 52.7 | 26.7 | 23.3 |

Examples 10 to 12

In the same manner as mentioned above, a base complex having a cellulose sponge and a fiber sheet made of a poly-L-lactic acid resin formed on the cellulose sponge was fabricated, and the fabricated base complex was die-cut with a metal punch to obtain a cylindrical base complex with a diameter of 13 mm. On the base part (fiber sheet part) of the obtained cylindrical base complex, 66.7 μL of a lipid solution with a concentration 30 mg/mL was sprayed, followed by drying, thus fabricating a hemostatic material. As the lipid solution, a tert-butyl alcohol solution of Asp-DHSG (Example 10), a tert-butyl alcohol solution of Glu-DHSG (Example 11) and a tert-butyl alcohol solution of AG-DHSG (Example 12) were used. As a control, a tert-butyl alcohol solution of DHSG was used. DHSG, Asp-DHSG, Glu-DHSG and AG-DHSG were prepared in the same manner as mentioned above. A hemostatic material fabricated using the tert-butyl alcohol solution of Asp-DHSG is hereinafter referred to as "hemostatic material E1," a hemostatic material fabricated using the tert-butyl alcohol solution of Glu-DHSG is hereinafter referred to as "hemostatic material E2," a hemostatic material fabricated using the tert-butyl alcohol solution of AG-DHSG is hereinafter referred to as "hemostatic material E3," and a hemostatic material fabricated using the tert-butyl alcohol solution of DHSG is hereinafter referred to as "hemostatic material E4."

Figure 5:
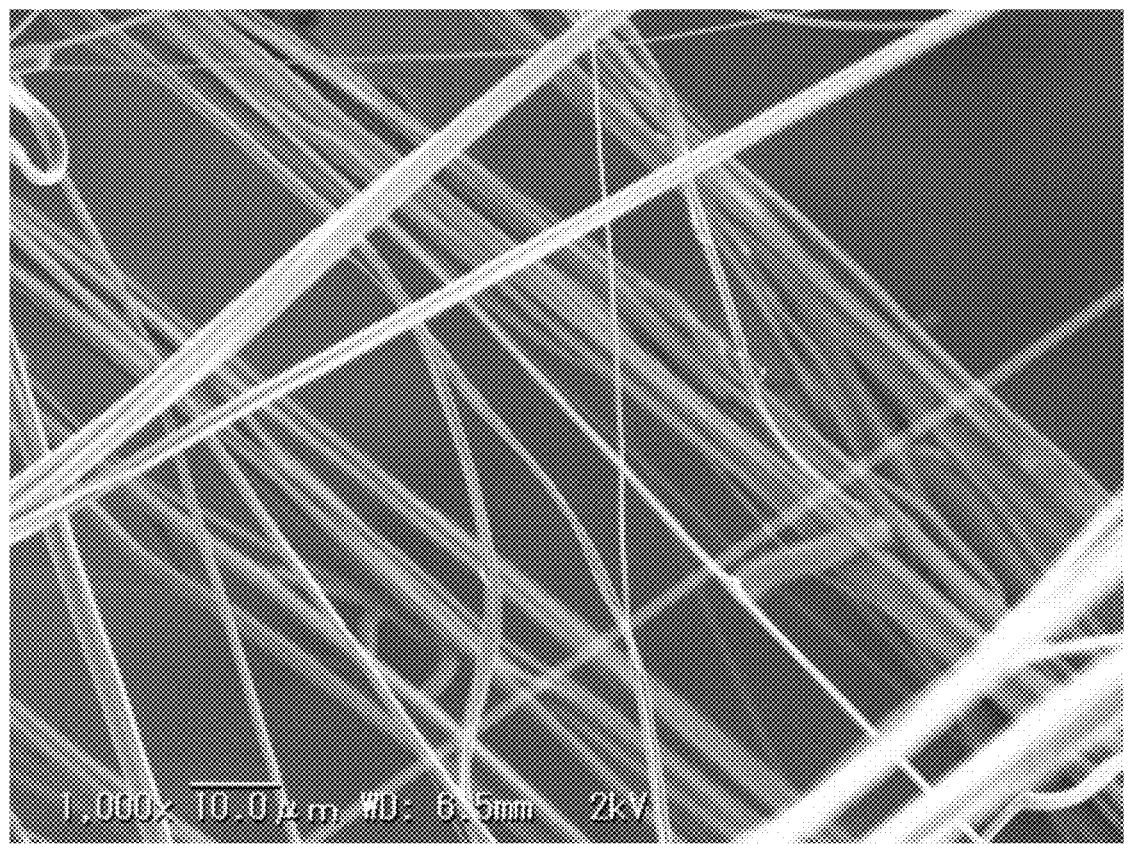
FIG. 5 shows an SEM observation image of a base.
Figure 6:
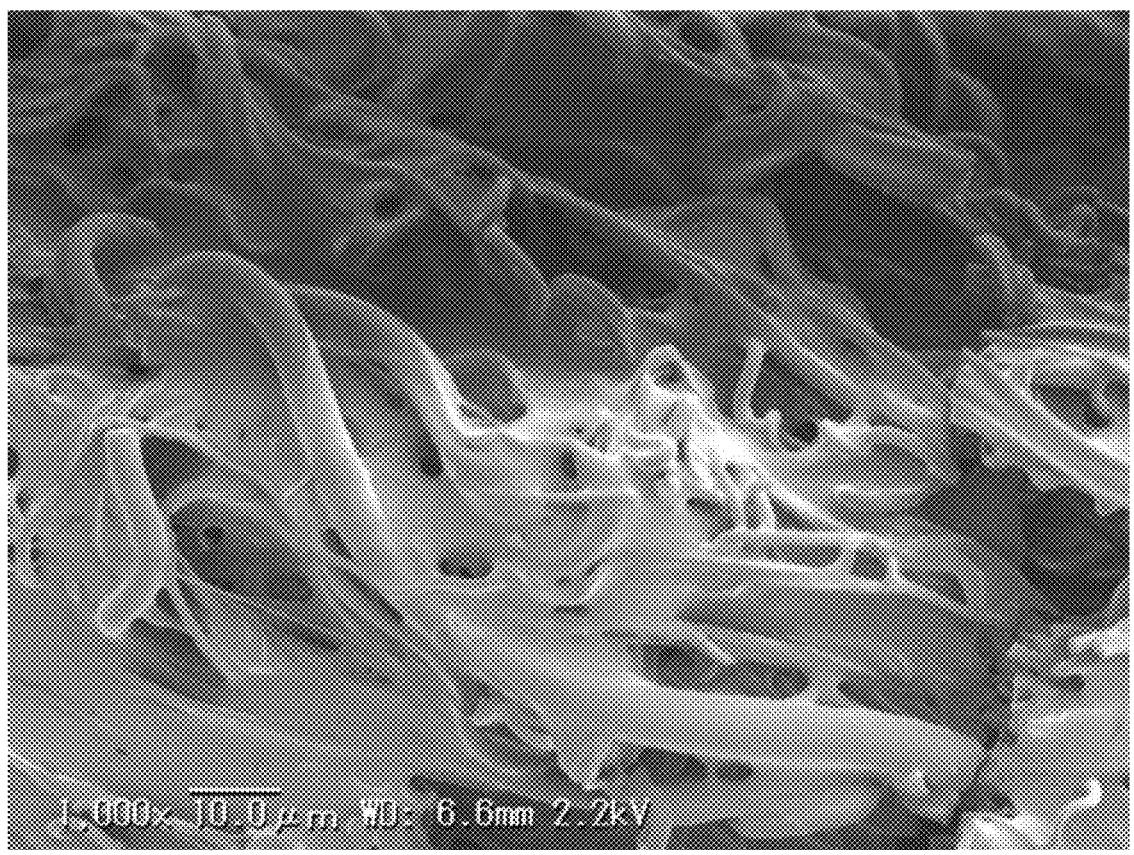
FIG. 6 shows an SEM observation image of Asp-DHSG supported on a base.
Figure 7:
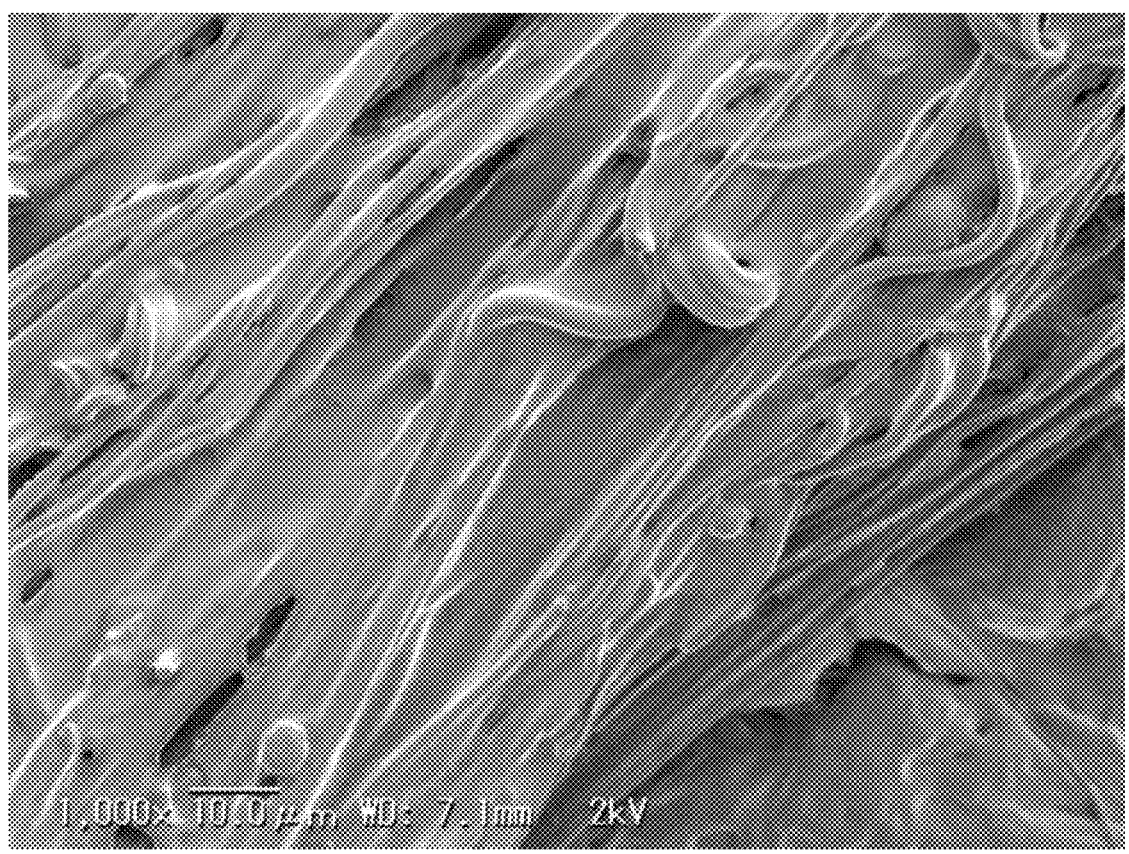
FIG. 7 shows an SEM observation image of Glu-DHSG supported on a base.
Figure 8:
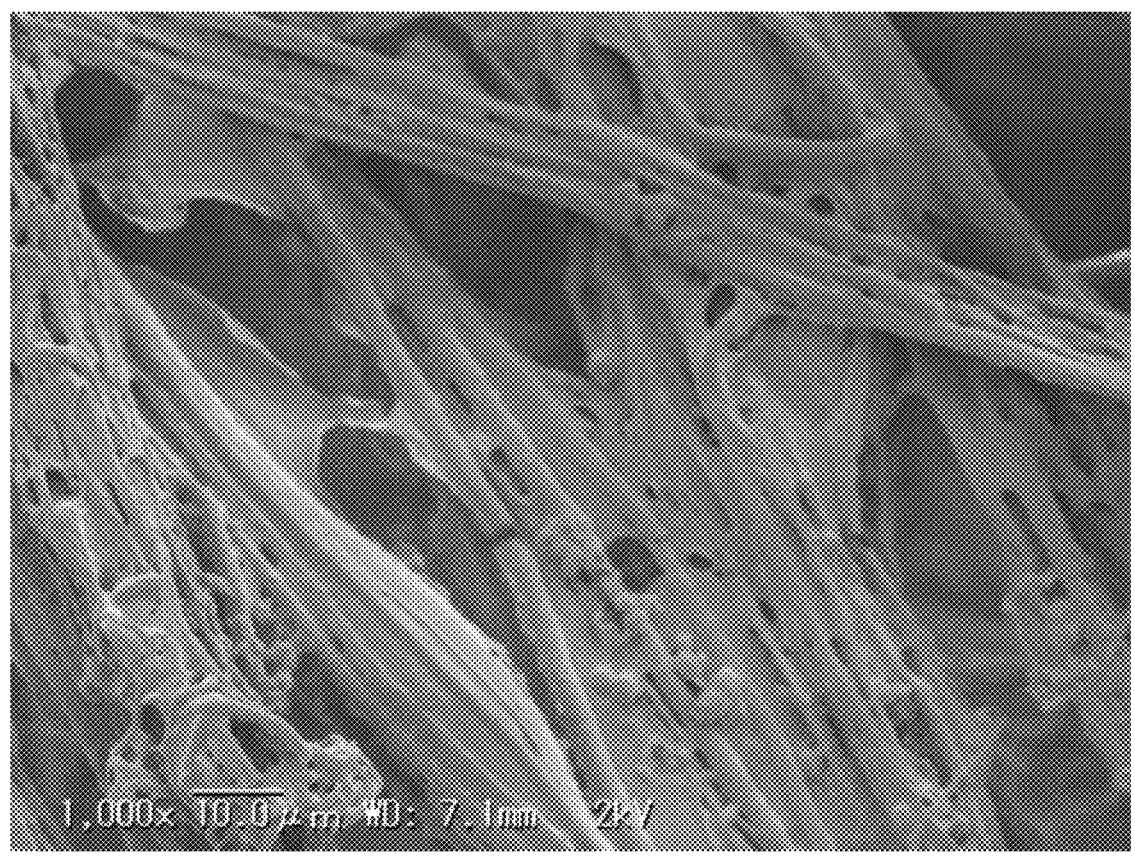
FIG. 8 shows an SEM observation image of AG-DHSG supported on a base.
Figure 9:
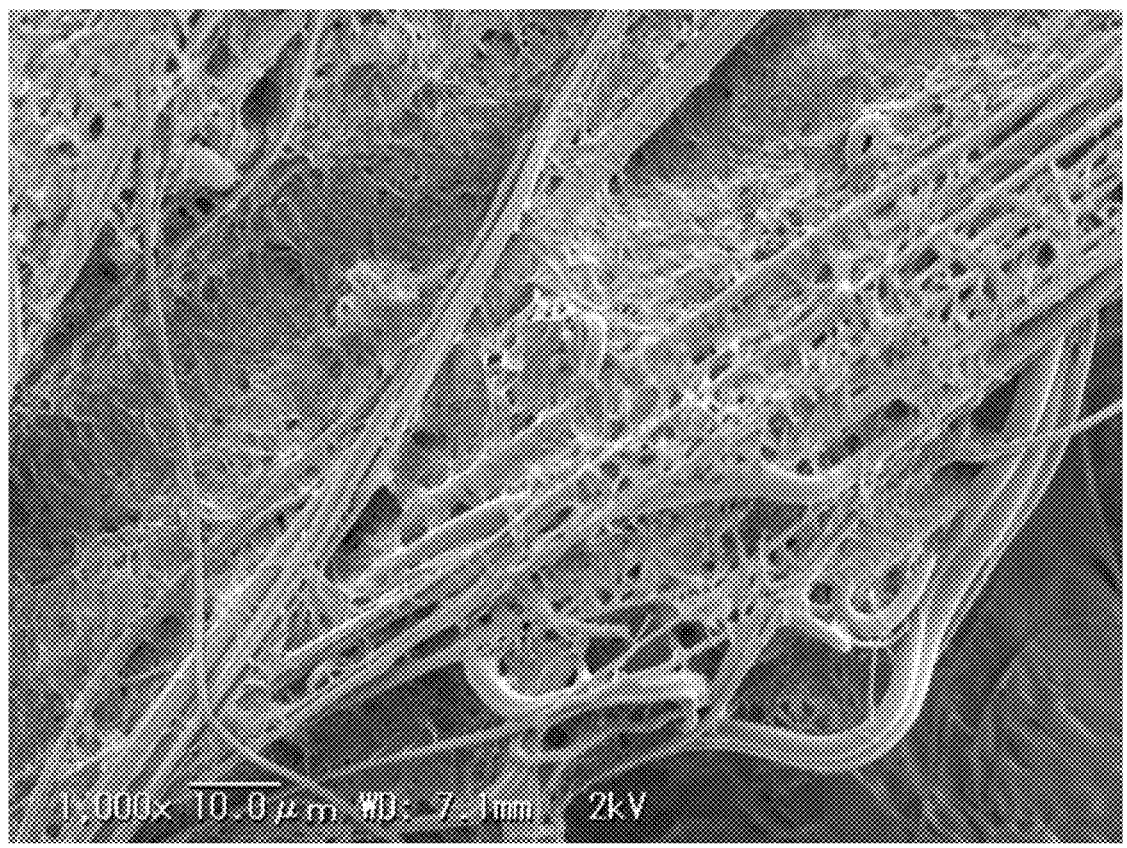
FIG. 9 shows an SEM observation image of DHSG supported on a base.
Figure 10:
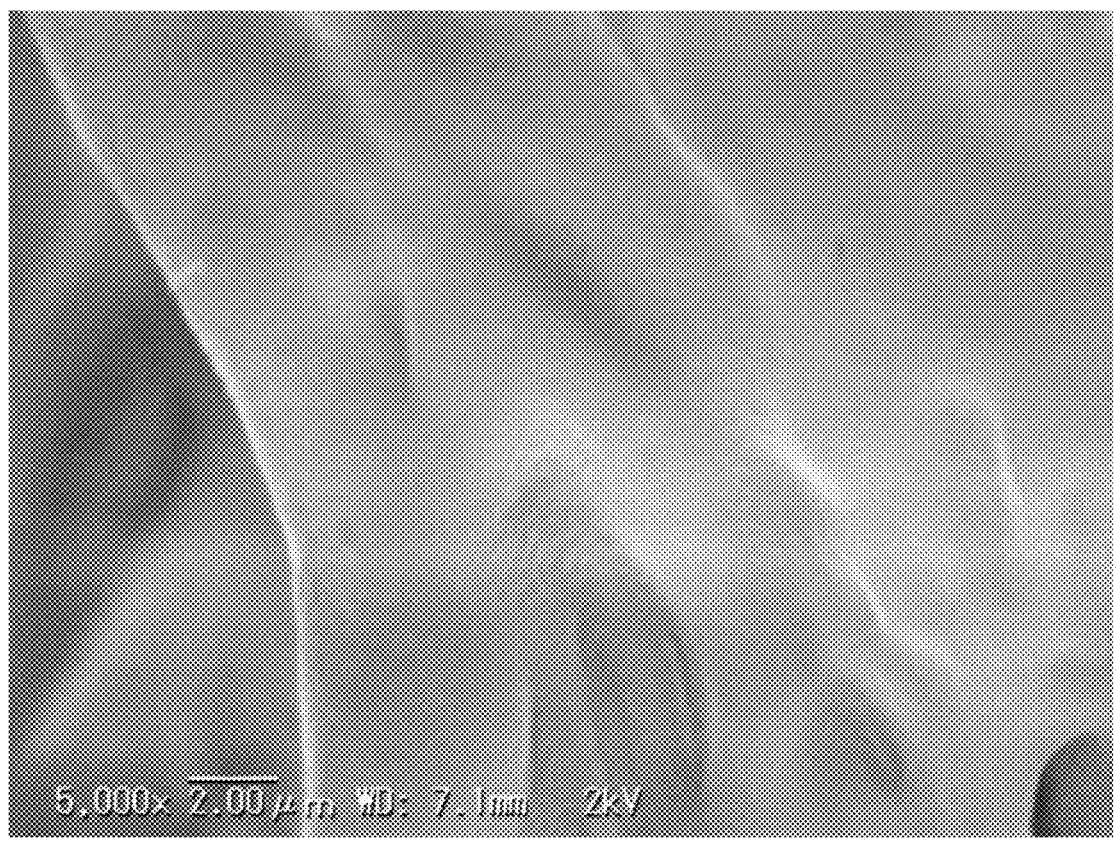
FIG. 10 shows an SEM observation image of Asp-DHSG supported on a base (an enlarged view of FIG. 6).
Figure 11:
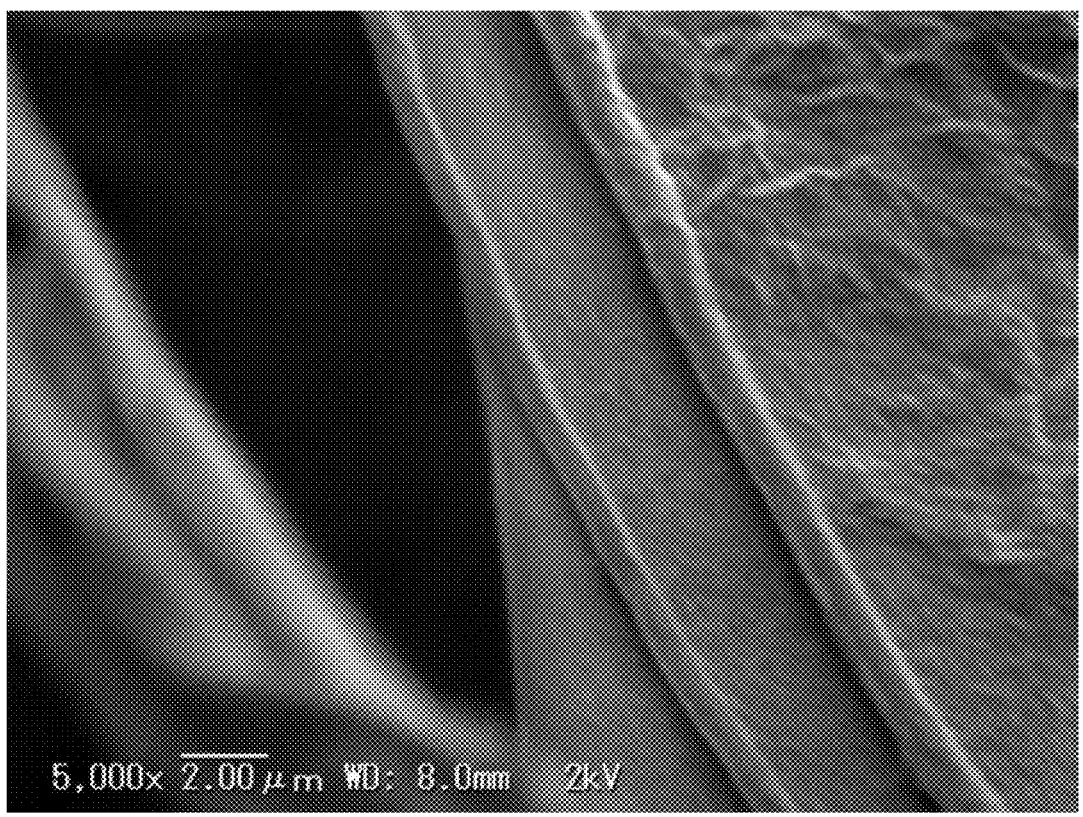
FIG. 11 shows an SEM observation image of Glu-DHSG supported on a base (an enlarged view of FIG. 7).
Figure 12:
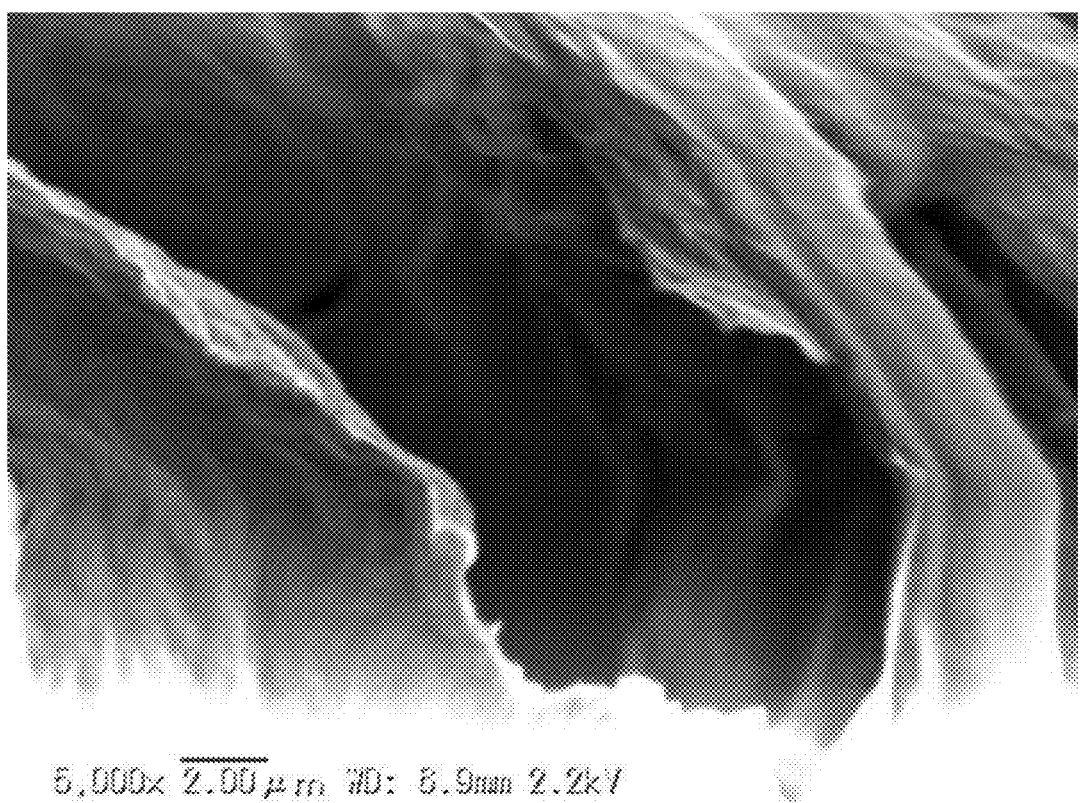
FIG. 12 shows an SEM observation image of AG-DHSG supported on a base (an enlarged view of FIG. 8).
Figure 13:
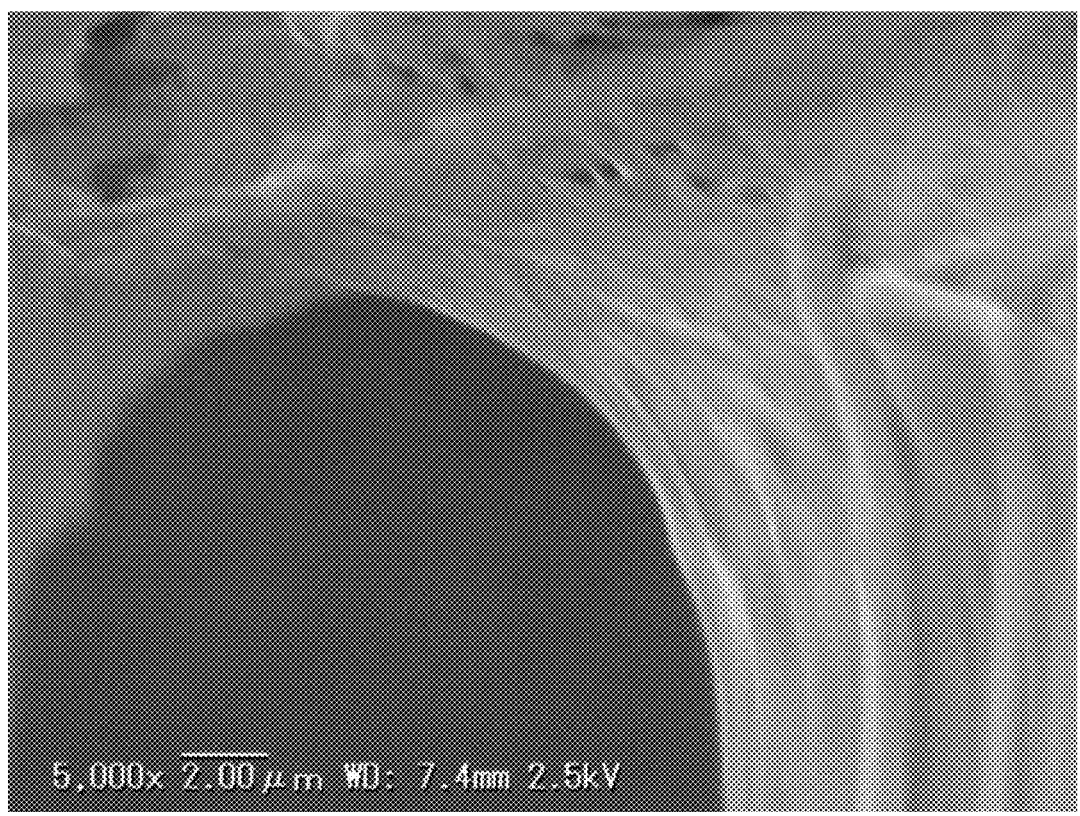
FIG. 13 shows an SEM observation image of DHSG supported on a base (an enlarged view of FIG. 9).

When a base complex before supporting a lipid and the base parts (fiber sheet parts) of the hemostatic materials E1 to E4 were subjected to ion sputtering treatment (target: Au) and observed with a scanning electron microscope (SEM), in the hemostatic materials E1 to E4, the majority of lipids had a membranous form spreading between fibers. An SEM observation image (×1,000) of the base complex before supporting a lipid is shown in FIG. 5, and SEM observation images (×1,000) of the hemostatic materials E1 to E4 are shown in FIGS. 6 to 9, respectively. SEM observation images (×5,000) of the hemostatic materials E1 to E4 are shown in FIGS. 10 to 13, respectively. The SEM observation images shown in FIGS. 10 to 13 are enlarged views of parts of the SEM observation images shown in FIGS. 6 to 9, respectively. The thickness of the lipid membrane (Asp-DHSG) calculated from the SEM observation image shown in FIG. 10 was 153 nm. The thickness of the lipid membrane (Glu-DHSG) calculated from the SEM observation image shown in FIG. 11 was 187 nm. The thickness of the lipid membrane (AG-DHSG) calculated from the SEM observation image shown in FIG. 12 was 124 nm. The thickness of the lipid membrane (DHSG) calculated from the SEM observation image shown in FIG. 13 was 131 nm.

The invention claimed is:
1. A compound having a structure represented by one of formulas (I) to (VI):

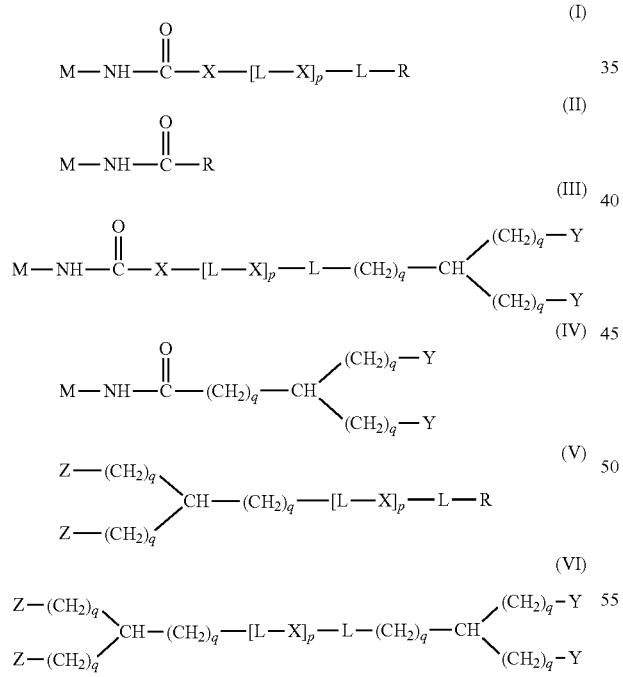

wherein, in formulas (I) to (VI),
M represents an amino acid residue, an amino acid derivative residue, a peptide residue or a salt thereof, wherein the amino acid residue, the amino acid derivative residue, the peptide residue and the salt thereof can be negatively charged at physiological pH,
the amino acid residue represented by M is an acidic amino acid residue or a neutral amino acid residue,
the amino acid derivative represented by M is a residue of a basic amino acid derivative, and an introduced derivatization that the basic amino acid derivative comprises is amidation of an amino group of a side chain of a basic amino acid to a group represented by a formula: —NH—CO—R1 wherein —NH— is derived from the amino group of the side chain of the basic amino acid, and R1 represents a hydrocarbon group,
the peptide residue represented by M is a peptide residue comprising one or more acidic amino acid residues,
R represents a hydrocarbon group,
L represents —CO—O—, —O—CO—, —CO—NH—, —NH—CO—, —CO—S—, —S—CO— or —S—S—,
X represents a hydrocarbon group, a neutral amino acid residue or a polyalkylene glycol residue,
p represents an integer of 0 or more,
q represents an integer of 0 or more,
Y represents a branched chain composed of a branched chain body and one or more groups Y2 that are bonded to the branched chain body, or represents a straight chain composed of one group Y2, wherein the branched chain body is composed of one or more units Y1, wherein each unit Y1 is represented by formula (VII):

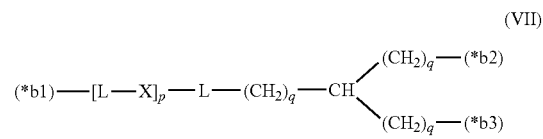

and wherein each group Y2 is represented by formula (VIII):

wherein, in formulas (VII) and (VIII),
R, L, X, p and q are the same as defined above,
(*b1), (*b2) and (*b3) represent a bond of each unit Y1,
(*b4) represents a bond of each group Y2,
the bond (*b1) of each unit Y1 is bonded to $(CH_2)_q$ in formula (III), (IV) or (VI), or is bonded to a bond (*b2) or (*b3) of another unit Y1 constituting the branched chain body, and
the bond (*b4) of each group Y2 is bonded to $(CH_2)_q$ in formula (III), (IV) or (VI), or is bonded to a bond (*b2) or (*b3) of any unit Y1 constituting the branched chain body,
Z represents a branched chain composed of a branched chain body and one or more groups Z2 that are bonded to the branched chain body, or represents a straight chain composed of one group Z2, wherein the branched chain body is composed of one or more units Z1, wherein each unit Z1 is represented by formula (IX):

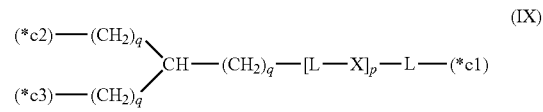

and wherein each group Z2 is selected from groups represented by formulas (X) and (XI):

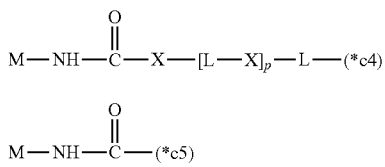

(X)

(XI)

wherein, in formulas (IX), (X) and (XI),

M, L, X, p and q are the same as defined above, (*c1), (*c2) and (*c3) represent a bond of each unit Z1, (*c4) and (*c5) represent a bond of each group Z2, the bond (*c1) of each unit Z1 is bonded to $(CH_2)_q$ in formula (V) or (VI), or is bonded to a bond (*c2) or (*c3) of another unit Z1 constituting the branched chain body, and the bond (*c4) or (*c5) of each group Z2 is bonded to $(CH_2)_q$ in formula (V) or (VI), or is bonded to a bond (*c2) or (*c3) of any unit Z1 constituting the branched chain body.

2. The compound according to claim 1, wherein the acidic amino acid residue is an aspartic acid residue or a glutamic acid residue.

3. The compound according to claim 1, wherein the peptide residue represented by M is a peptide residue comprising two or more acidic amino acid residues selected from an aspartic acid residue and a glutamic acid residue.

4. The compound according to claim 3, wherein the peptide residue represented by M is a peptide residue represented by formula (XII):

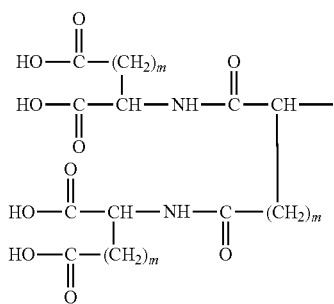

(XII)

wherein m is the same or different and represents 1 or 2.

5. The compound according to claim 1, wherein L is the same or different and represents —CO—O—, —O—CO—, —CO—NH— or —NH—CO—.

6. The compound according to claim 1, wherein Y is selected from straight and branched chains represented by formulas (XIII), (XIV), (XV) and (XVI):

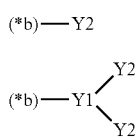

(XIII)

(XIV)

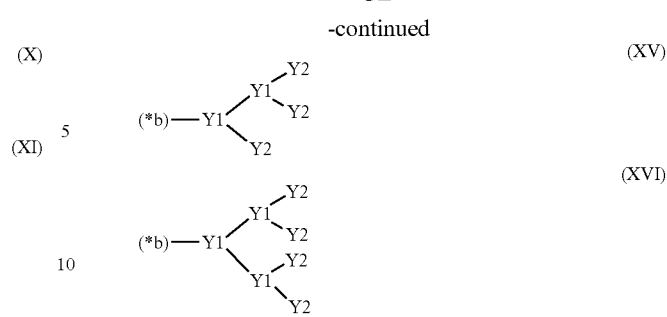

(XV)

(XVI)

wherein, in formulas (XIII) to (XVI),

Y1 represents one unit Y1,

Y2 represents one group Y2, and (*b) represents a bond of the unit Y1 bonded to $(CH_2)_q$ in formula (III), (IV) or (VI).

7. The compound according to claim 1, wherein Z is selected from straight and branched chains represented by formulas (XVII), (XVIII), (XIX) and (XX):

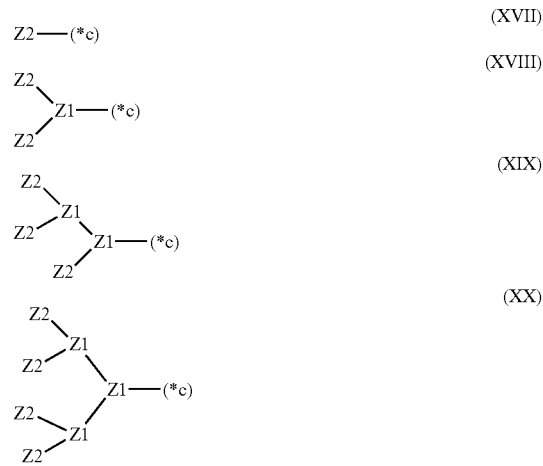

(XVII)

(XVIII)

(XIX)

(XX)

wherein, in formulas (XVII) to (XX),

Z1 represents one unit Z1,

Z2 represents one group Z2, and (*c) represents a bond of the unit Z1 bonded to $(CH_2)_q$ in formula (V) or (VI).

8. A lipid, comprising the compound according to claim 1 and one or more lipids selected from a phospholipid, a glycolipid, a sterol and a fatty acid.

9. A method for affecting hemostasis, comprising administering the compound according to claim 1 to a bleeding site of a subject.

10. A composition, comprising the compound according to claim 1 and a pharmaceutically acceptable carrier or additive.

11. A method for affecting hemostasis, comprising administering the lipid according to claim 8 to a bleeding site of a subject.

12. A composition, comprising the lipid according to claim 8 and a pharmaceutically acceptable carrier or additive.

* * * * *